United States Patent
Bossard et al.

(10) Patent No.: US 12,247,059 B2
(45) Date of Patent: *Mar. 11, 2025

(54) CONJUGATES OF AN IL-2 MOIETY AND A POLYMER

(71) Applicant: Nektar Therapeutics, San Francisco, CA (US)

(72) Inventors: Mary J. Bossard, Madison, AL (US); Cherie F. Ali, Burlingame, CA (US); Xiaofeng Liu, Belmont, CA (US); Deborah H. Charych, Albany, CA (US); Yujun Wang, Fremont, CA (US)

(73) Assignee: Nektar Therapeutics, San Francisco, CA (US)

( * ) Notice: Subject to any disclaimer, the term of this patent is extended or adjusted under 35 U.S.C. 154(b) by 149 days.

This patent is subject to a terminal disclaimer.

(21) Appl. No.: 17/373,665

(22) Filed: Jul. 12, 2021

(65) Prior Publication Data
US 2021/0340210 A1    Nov. 4, 2021

Related U.S. Application Data

(60) Continuation of application No. 16/139,957, filed on Sep. 24, 2018, now Pat. No. 11,091,525, which is a (Continued)

(51) Int. Cl.
*C07K 14/55* (2006.01)
*A61K 38/20* (2006.01)
*A61K 47/60* (2017.01)

(52) U.S. Cl.
CPC .......... *C07K 14/55* (2013.01); *A61K 38/2013* (2013.01); *A61K 47/60* (2017.08)

(58) Field of Classification Search
None
See application file for complete search history.

(56) References Cited

U.S. PATENT DOCUMENTS

| 4,401,756 A | 8/1983 | Gillis |
| 4,705,848 A | 11/1987 | Yang et al. |

(Continued)

FOREIGN PATENT DOCUMENTS

| CN | 101104077 A | 1/2008 |
| EP | 0 473 268 | 3/1992 |

(Continued)

OTHER PUBLICATIONS

Greenwald et al (Bioconjugate Chem. 2003, 14, 395-403) (Year: 2003).*

(Continued)

*Primary Examiner* — Brian Gangle
*Assistant Examiner* — Andrea K McCollum
(74) *Attorney, Agent, or Firm* — Susan T. Evans; Jacqueline F. Mahoney

(57) ABSTRACT

Conjugates of an interleukin-2 ("IL-2") moiety and one or more nonpeptidic, water-soluble polymers are provided. Typically, the non-peptidic, water-soluble polymer is poly (ethylene glycol) or a derivative thereof. Also provided, among other things, are compositions comprising conjugates, methods of making conjugates, methods of administering compositions to an individual, nucleic acid sequences, expression systems, host cells, and methods for preparing IL-moieties.

15 Claims, 16 Drawing Sheets

Specification includes a Sequence Listing.

```
  1    CATATGCCGACCAGCAGCAGCACCAAAAAAACCCAGCTGCAGCTGGAACATCTGCTGCTG
  1        M  P  T  S  S  S  T  K  K  T  Q  L  Q  L  E  H  L  L  L

61    GATCTGCAGATGATCCTGAACGGTATCAACAACTACAAAAACCCGAAACTGACCCGTATG
 22        D  L  Q  M  I  L  N  G  I  N  N  Y  K  N  P  K  L  T  R  M

121    CTGACCTTCAAATTCTACATGCCGAAAAAAGCAACCGAACTGAAACATCTGCAGTGCCTG
 40        L  T  F  K  F  Y  M  P  K  K  A  T  E  L  K  H  L  Q  C  L

181    GAAGAAGAACTGAAACCGCTGGAAGAAGTGCTGAACCTGGCACAGAGCAAAAACTTCCAT
 60        E  E  E  L  K  P  L  E  E  V  L  N  L  A  Q  S  K  N  F  H

241    CTGCGTCCGCGTGATCTGATCAGCAACATCAACGTGATCGTGCTGGAACTGAAAGGTAGC
 80        L  R  P  R  D  L  I  S  N  I  N  V  I  V  L  E  L  K  G  S

301    GAAACCACCTTCATGTGCGAATACGCAGATGAAACCGCAACCATCGTGGAATTTCTGAAC
100        E  T  T  F  M  C  E  Y  A  D  E  T  A  T  I  V  E  F  L  N

361    CGTTGGATCACCTTCAGCCAGAGCATCATCAGCACCCTGACCTAAGAATTC
120        R  W  I  T  F  S  Q  S  I  I  S  T  L  T  *
```

Related U.S. Application Data division of application No. 15/835,125, filed on Dec. 7, 2017, now Pat. No. 10,960,079, which is a division of application No. 13/884,901, filed as application No. PCT/US2011/060408 on Nov. 11, 2011, now Pat. No. 9,861,705.

(60) Provisional application No. 61/413,236, filed on Nov. 12, 2010.

(56) References Cited

U.S. PATENT DOCUMENTS

| | | | |
|---|---|---|---|
| 4,766,106 | A | 8/1988 | Katre et al. |
| 4,902,502 | A | 2/1990 | Nitecki et al. |
| 5,078,997 | A | 1/1992 | Hora et al. |
| 5,089,261 | A | 2/1992 | Niteck et al. |
| 5,116,943 | A | 5/1992 | Koth et al. |
| 5,153,310 | A | 10/1992 | Mitchell et al. |
| 5,206,344 | A | 4/1993 | Katre et al. |
| 5,419,899 | A | 5/1995 | Koths et al. |
| 5,614,185 | A | 3/1997 | Koths et al. |
| 5,635,597 | A | 6/1997 | Barrett et al. |
| 5,739,208 | A | 4/1998 | Harris |
| 5,932,462 | A | 8/1999 | Harris et al. |
| 6,034,072 | A | 3/2000 | Ralston et al. |
| 6,180,095 | B1 | 1/2001 | Greenwald et al. |
| 6,706,289 | B2 | 3/2004 | Lewis et al. |
| 7,101,965 | B2 | 9/2006 | Theze et al. |
| 7,511,094 | B2 * | 3/2009 | Kozlowski ......... C08G 65/2603 525/50 |
| 7,585,837 | B2 | 9/2009 | Shechter et al. |
| 9,861,705 | B2 * | 1/2018 | Bossard .................. A61P 37/08 |
| 10,960,079 | B2 * | 3/2021 | Bossard .................. A61P 29/00 |
| 2004/0136952 | A1 | 7/2004 | Bhaskaran et al. |
| 2004/0175337 | A1 | 9/2004 | Richard et al. |
| 2005/0014903 | A1 | 1/2005 | Kozlowksi et al. |
| 2005/0186174 | A1 | 8/2005 | Bossard |
| 2006/0293499 | A1 | 12/2006 | Bentley et al. |
| 2009/0263382 | A1 | 10/2009 | Ewert et al. |
| 2010/0036097 | A1 | 2/2010 | Wittrup et al. |
| 2011/0190209 | A1 * | 8/2011 | Culbertson ............ A61K 47/60 530/383 |
| 2014/0328791 | A1 | 11/2014 | Bossard et al. |
| 2018/0085468 | A1 | 3/2018 | Bossard et al. |
| 2019/0008978 | A1 | 1/2019 | Huang et al. |

FOREIGN PATENT DOCUMENTS

| | | |
|---|---|---|
| EP | 0 510 356 A1 | 10/1992 |
| EP | 1 688 146 | 8/2006 |
| KR | 10-2009-0103209 | 10/2009 |
| WO | WO 87/00056 A1 | 1/1987 |
| WO | WO 90/12874 | 11/1990 |
| WO | WO 99/45964 | 9/1999 |
| WO | WO 99/60128 | 11/1999 |
| WO | WO 01/62827 | 8/2001 |
| WO | WO 02/00243 | 1/2002 |
| WO | WO 2004/060300 | 7/2004 |
| WO | WO 2004/089280 | 10/2004 |
| WO | WO 2005/000360 A2 | 1/2005 |
| WO | WO 2006/138572 A2 | 12/2006 |
| WO | WO 2007/075534 A2 | 7/2007 |
| WO | WO 2007/117685 A2 | 10/2007 |
| WO | WO 2008/082669 A2 | 7/2008 |
| WO | WO 2008/106186 A2 | 9/2008 |
| WO | WO 2009/139905 A2 | 11/2009 |
| WO | WO 2010/033207 A1 | 3/2010 |

OTHER PUBLICATIONS

Katre et al (Proc Natl Acad Sci U S A. Mar. 1987;84(6):1487-91) (Year: 1987).*

Kegg data sheet for Aldesleukin (downloaded Jan. 13, 2024 from https://www.genome.jp/dbget-bin/www_bget?dr:D00748) (Year: 2024).*

Knauf et al (J Biol Chem. Oct. 15, 1988;263(29):15064-70) (Year: 1988).*

Abuchowski, et al., "Cancer Therapy with Chemically Modified Enzymes. I. Antitumor Properties of Polyethylene Glycol-Asparaginase Conjugates", Cancer Biochem. Biophys., vol. 7, pp. 175-186, (1984).

Arakawa, et al., "Structure and solubility of interleukin-2 in sodium dodecyl sulfate," International Journal of Peptide & Protein Research, vol. 43, pp. 583-587, (1994).

Bork, "Powers and Pitfalls in Sequence Analysis: The 70% Hurdle", Genome Res., vol. 10, pp. 398-400, (2000).

Bowie, et al., "Deciphering the Message in Protein Sequences: Tolerance to Amino Acid Substitutions", Science, vol. 247, No. 4948, pp. 1306-1310, (1990).

Burgess, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Biol., vol. 111, pp. 2129-2138, (1990).

Chen, et al., "Plasma and Lymph Pharmacokinetics of Recombinant Human Interleukin-2 and Polyethylene Glycol-Modified Interleukin-2 in Pigs," The Journal of Pharmacology and Experimental Therapeutics, vol. 293, No. 1, pp. 248-259, (2000).

Devlin, et al., "Alteration of amino-terminal codons of human granulocyte-colony-stimulating factor increases expression levels and allows efficient processing by methionine aminopeptidase in Escherichia coli," Gene, vol. 65, pp. 13-22, (1988).

Goodson, et al., "Site-Directed Pegylation of Recombinant Interleukin-2 at its Glycosylation Site," Bio/Technology, vol. 8, pp. 343-346, (1990).

Greenwald, et al., "Controlled Release of Proteins from Their Poly(Ethylene Glycol) Conjugates: Drug Delivery Systems Employing 1,6-Elimination," Bioconjugate Chem., vol. 14, pp. 395-403, (2003).

Harris, et al., "Effect of Pegylation on Pharmaceuticals", Nat. Rev. Drug Discov., vol. 2, No. 3, pp. 214-221, (2003).

Heldt, et al., "The Use of Glycidol to Introduce Aldehyde Functions Into Proteins—Application to the Fluorescent Labelling of Bovine Serum Albumin and Avidin," Eur. J. Org. Chem., vol. 32, pp. 5429-5433, (2007).

Hora, et al., "Controlled Release of Interleukin-2 From Biodegradable Microspheres," Bio/Technology, vol. 8, pp. 755-758, (1990).

Katre, et al., "Chemical modification of recombinant interleukin 2 by polyethylene glycol increases its potency in the murine Meth A sarcoma model," Proc. Natl. Acad. Sci. USA, vol. 84, pp. 1487-1491, (1987).

Knauf, et al., "Relationship of Effective Molecular Size to Systemic Clearance in Rats of Recombinant Interleukin-2 Chemically Modified with Water-soluble Polymers," The Journal of Biological Chemistry, vol. 263, No. 29, pp. 15064-15070, (1988).

Lazar, et al., "Transforming Growth Factor α: Mutation of Aspartic Acid 47 and Leucine 48 Results in Different Biological Activities", Mol. Cell Biol., vol. 8, No. 3, pp. 1247-1252, (1988).

Luchansky, et al., "Metabolic Functionalization of Recombinant Glycoproteins," vol. 43, No. 38, pp. 12358-12366, (2004).

Moreau, et al., Characterization of a Monoclonal Antibody Directed Against the NH2 Terminal Area of Interleukin-2 (IL-2) and Inhibiting Specifically the Binding of IL-2 to IL-2 Receptor β Chain (IL-2Rβ), Molecular Immunology, vol. 32, No. 14/15, pp. 1047-1056, (1995).

Ouchi, et al., "Design of Antitumor Agent-Terminated Poly(Ethylene Glycol) Conjugate as Macromolecular Prodrug," Polymer Preprints, vol. 38, No. 1, pp. 582-583, (1997).

Pauly, et al., "Isolation of Interleukin 2 (IL-2) from Human and Mouse Lymphocyte Culture Supernatants by Batch Adsorption onto Silicic Acid," Journal of Immunological Methods, vol. 75, pp. 73-84, (1984).

Samlowski, et al., "ReGel® Polymer-based Delivery of Interleukin-2 as a Cancer Treatment," J. Immunother., vol. 29, No. 5, pp. 524-535, (2006).

(56) References Cited

OTHER PUBLICATIONS

Shechter, et al., "Prolonging the half-life of human interferon-α2 in circulation: Design, preparation, and analysis of (2-sulfo-9-fluorenylmethoxycarbonyl)$_7$-interferon-α2," PNAS, vol. 98, No. 3, pp. 1212-1217, (2001).
Shechter, et al., "Suspensions of pro-drug insulin greatly prolong normoglycemic patterns in diabetic rats," Biochemical and Biophysical Research Communications, vol. 307, pp. 315-321, (2003).
Shechter, et al., "Reversible PEGylation of peptide YY$_{3-36}$ prolongs its inhibition of food intake in mice," FEBS Letters, vol. 579, pp. 2439-2444, (2005).
Shechter, et al., "Reversible pegylation of insulin facilitates its prolonged action in vivo," European Journal of Pharmaceutics and Biopharmaceutics, vol. 70, pp. 19-28, (2008).
Sims, et al., "A Method for the Estimation of Polyethylene Glycol in Plasma Protein Fractions," Analytical Biochemistry, vol. 107, pp. 60-63, (1980).
Teppler, et al., "Prolonged Immunostimulatory Effect of Low-Dose Polyethylene Glycol Interleukin 2 in Patients with Human Immunodeficiency Virus Type 1 Infection," J. Exp. Med., vol. 177, pp. 483-492, (1993).
Tsubery, et al., "Prolonging the Action of Protein and Peptide Drugs by a Novel Approach of Reversible Polyethylene Glycol Modification," The Journal of Biological Chemistry, vol. 279, No. 37, pp. 38118-38124, (2004).
Yang, et al., "Murine Studies Using Polyethylene Glycol-Modified Recombinant Human Interleukin 2 (PEG-IL-2): Antitumor Effects of PEG-IL2 Alone and in Combination with Adoptive Cellular Transfer," Lymphokine and Cytokine Research, vol. 10, No. 6, pp. 475-480, (1991).
Yang, et al., "The Use of Polyethylene Glycol-Modified Interleukin-2 (PEG-IL-2) in the Treatment of Patients with Metastatic Renal Cell Carcinoma and Melanoma," Cancer, vol. 76, No. 4, pp. 687-694, (1995).
Young, et al., "Two-step total gene synthesis method," Nucleic Acids Research, vol. 32, No. 7, e59, pp. 1-6, (2004).
Zalipsky, et al., "Attachment of Drugs to Polyethylene Glycols", Eur. Polym. J., vol. 19, No. 12, pp. 1177-1183, (1983).
Zalipsky, et al., "Chemistry of polyethylene glycol conjugates with biologically active molecules", Advanced Drug Delivery Reviews, vol. 16, pp. 157-182, (1995).
Zalipsky, et al., "Use of Functionalized Poly(Ethylene Glycol)s for Modification of Polypeptides", in Poly(Ethylene Glycol) Chemistry: Biotechnical and Biomedical Applications, edited by J. Milton Harris, Plenum Press, New York, pp. 347-370 (1992).
Zimmerman, et al., "Schedule Dependency of the Antitumor Activity and Toxicity of Polyethylene Glycol-modified Interleukin 2 in Murine Tumor Models," Cancer Research, vol. 49, pp. 6521-6528, (1989).
PCT International Search Report and Written Opinion corresponding to PCT International Application No. PCT/US2011/060408 date of mailing Mar. 26, 2012.
PCT International Preliminary Report on Patentability corresponding to PCT International Application No. PCT/US2011/060408 date of mailing May 23, 2013.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
Nektar™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, 46 pages, Catalogue 2003—1$^{st}$, (Jan. 2003).

NOF Corporation, PEG Derivatives, Phospholipid and Drug Delivery Materials for Pharmaceuticals, 27 pages, Catalogue 2003—2$^{nd}$, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Australian Patent Examination Report No. 1 corresponding to Australian Patent No. 2011325990 date of issue Feb. 15, 2016.
Canadian Office Communication corresponding to Canadian Patent Application No. 2,816,722 dated Sep. 8, 2017.
First Office Action corresponding to Chinese Patent Application No. 201180064511.4, date of notification Sep. 10, 2014.
Chinese Notification of the Second Office Action corresponding to Chinese Patent Application No. 201180064511.4 dated Jul. 15, 2015.
English Translation of Notification of the Third Office Action corresponding to Chinese Patent Application No. 201180064511.4 date of notification Mar. 22, 2016.
English Translation of Notification of the Fourth Office Action corresponding to Chinese Patent Application No. 201180064511.4 date of notification Dec. 12, 2016.
Official Action in Eurasian Patent Application No. 201390697, 3 pages, (Jan. 2015).
Eurasian Official Action corresponding to Eurasian Patent Application No. 201390697 dated Aug. 15, 2015.
English Translation of Official Action corresponding to Eurasian Patent Application No. 201390697 dated Apr. 18, 2016.
European Communication corresponding to European Patent Application No. 11840401.1 dated May 25, 2016.
European Communication corresponding to European Patent Application No. 11840401.1 dated Nov. 7, 2017.
English Translation of an Office Communication corresponding to Israeli Patent Application No. 226267 dated Jul. 3, 2016.
English Translation of an Office Communication corresponding to Israeli Patent Application No. 226267 dated Oct. 31, 2017.
Japanese Notice of Reasons for Rejection corresponding to Japanese Patent Application No. 2013-538940 mailing date Sep. 2, 2015.
English Translation of Notice of Reasons for Rejection corresponding to Japanese Patent Application No. 2013-538940 mailing date May 18, 2017.
English Translation of Examination Report corresponding to Mexican Patent Application No. MX/a/2013/005363 dated Oct. 13, 2017.
Arakawa et al., "Structure of Unfolded and Refolded Recombinant Derived [Ala$^{125}$]Interleukin 2", Biochemistry, vol. 25, pp. 8274-8277, (1986).
Pettit et al., "Structure-Function Studies of Interleukin 15 using Site-specific Mutagenesis, Polyethylene Glycol Conjugation, and

(56) References Cited

OTHER PUBLICATIONS

Homology Modeling", The Journal of Biological Chemistry, vol. 272, No. 4, Issue of Jan. 24, pp. 2312-2318, (1997).
English Translation of Official Action corresponding to Eurasian Patent Application No. 201390697 dated Apr. 28, 2017.
English Translation of Notice of Final Rejection corresponding to Japanese Patent Application No. 2013-538940 mailing date May 2, 2016.
English Translation of Pre-Approval Examination Report corresponding to Japanese Patent Application No. 2013-538940 mailing date Dec. 12, 2016.
English Translation of Notice of Reasons for Rejection corresponding to Japanese Patent Application No. 2013-538940 mailing date Dec. 1, 2017.
English Translation of Notice of Grounds for Rejection corresponding to Korean Patent Application No. 10-2013-7014802 issuance date Aug. 17, 2018.

* cited by examiner

```
  1  CATATGCCGACCAGCAGCAGCACCAAAAAAACCCAGCTGCAGCTGGAACATCTGCTGCTG
  1   M  P  T  S  S  S  T  K  K  T  Q  L  Q  L  E  H  L  L  L

61  GATCTGCAGATGATCCTGAACGGTATCAACAACTACAAAAACCCGAAACTGACCCGTATG
 22   D  L  Q  M  I  L  N  G  I  N  N  Y  K  N  P  K  L  T  R  M

121  CTGACCTTCAAATTCTACATGCCGAAAAAGCAACTGAACTGAAACATCTGCAGTGCCTG
 40   L  T  F  K  F  Y  M  P  K  K  A  T  E  L  K  H  L  Q  C  L

181  GAAGAAGAACTGAAACCGCTGGAAGAAGTGCTGAACCTGGCACAGAGCAAAAACTTCCAT
 60   E  E  E  L  K  P  L  E  E  V  L  N  L  A  Q  S  K  N  F  H

241  CTGCGTCCGCGTGATCTGATCAGCAACATCAACGTGATCGTGCTGGAACTGAAAGGTAGC
 80   L  R  P  R  D  L  I  S  N  I  N  V  I  V  L  E  L  K  G  S

301  GAAACCACCTTCATGTGCGAATACGCAGATGAAACCGCAACCATCGTGGAATTTCTGAAC
100   E  T  T  F  M  C  E  Y  A  D  E  T  A  T  I  V  E  F  L  N

361  CGTTGGATCACCTTCAGCCAGAGCATCATCAGCACCCTGACCTAAGAATTC
120   R  W  I  T  F  S  Q  S  I  I  S  T  L  T  *
```

FIG. 1

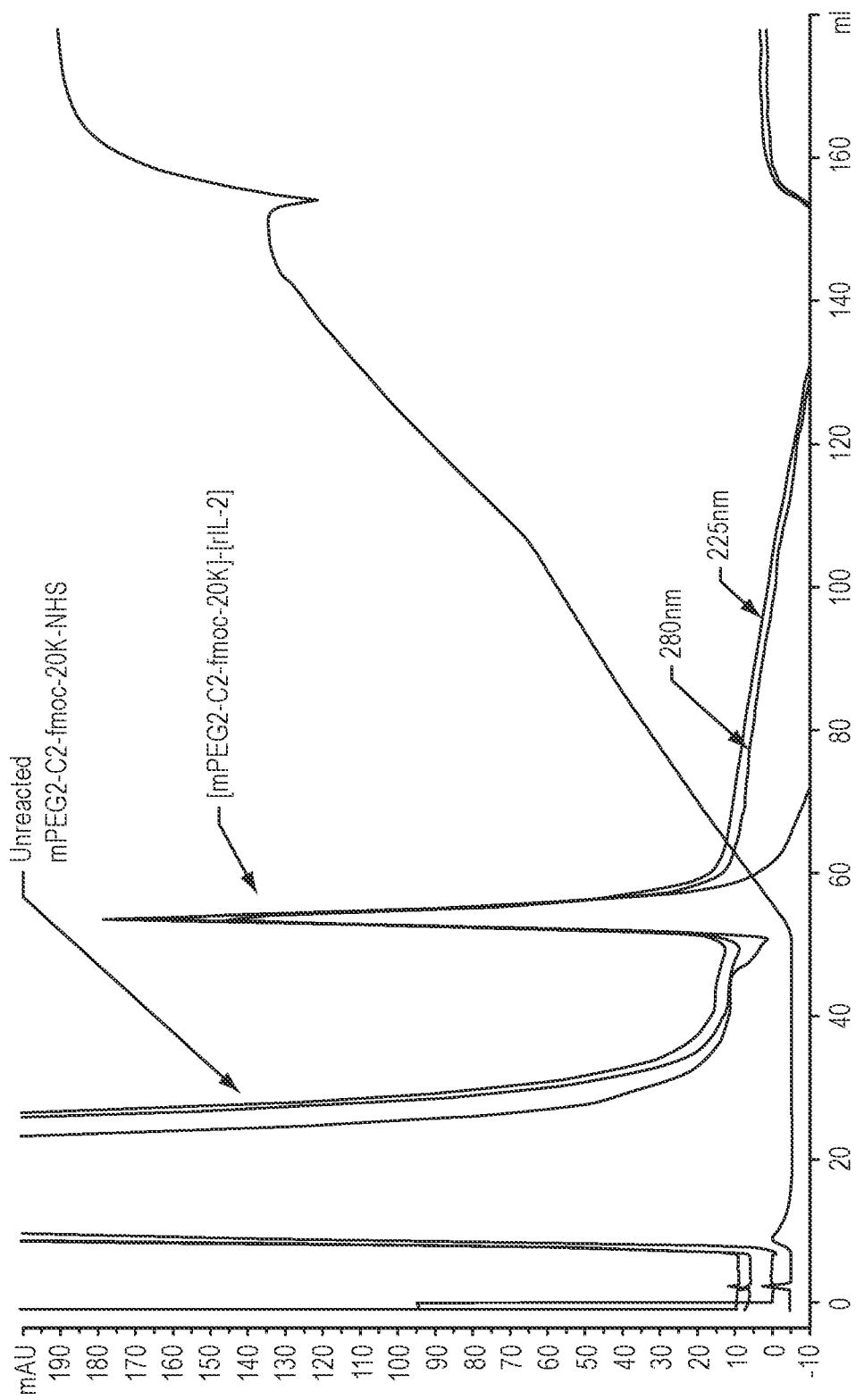
FIG. 2.1

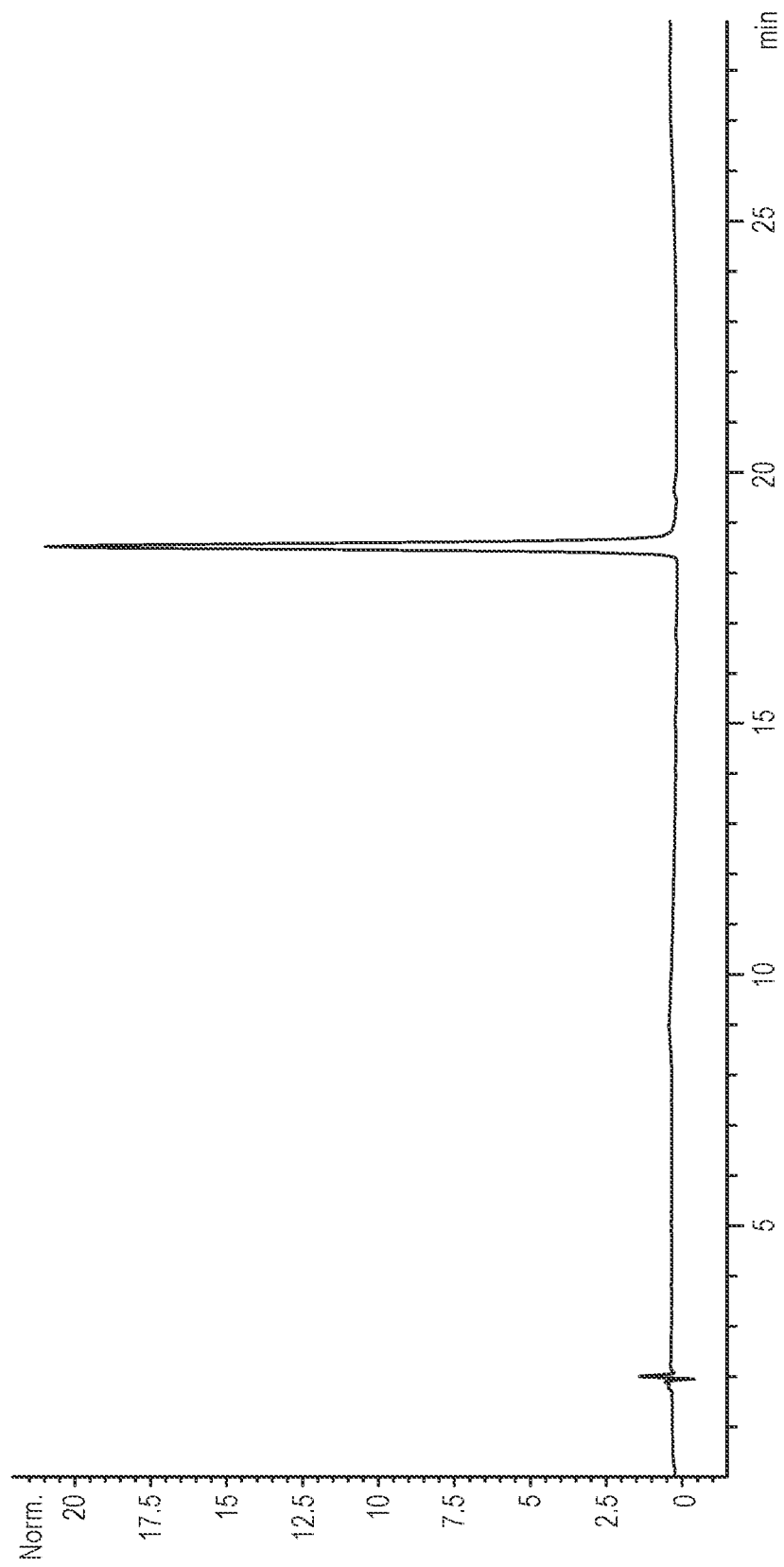
FIG. 2.2

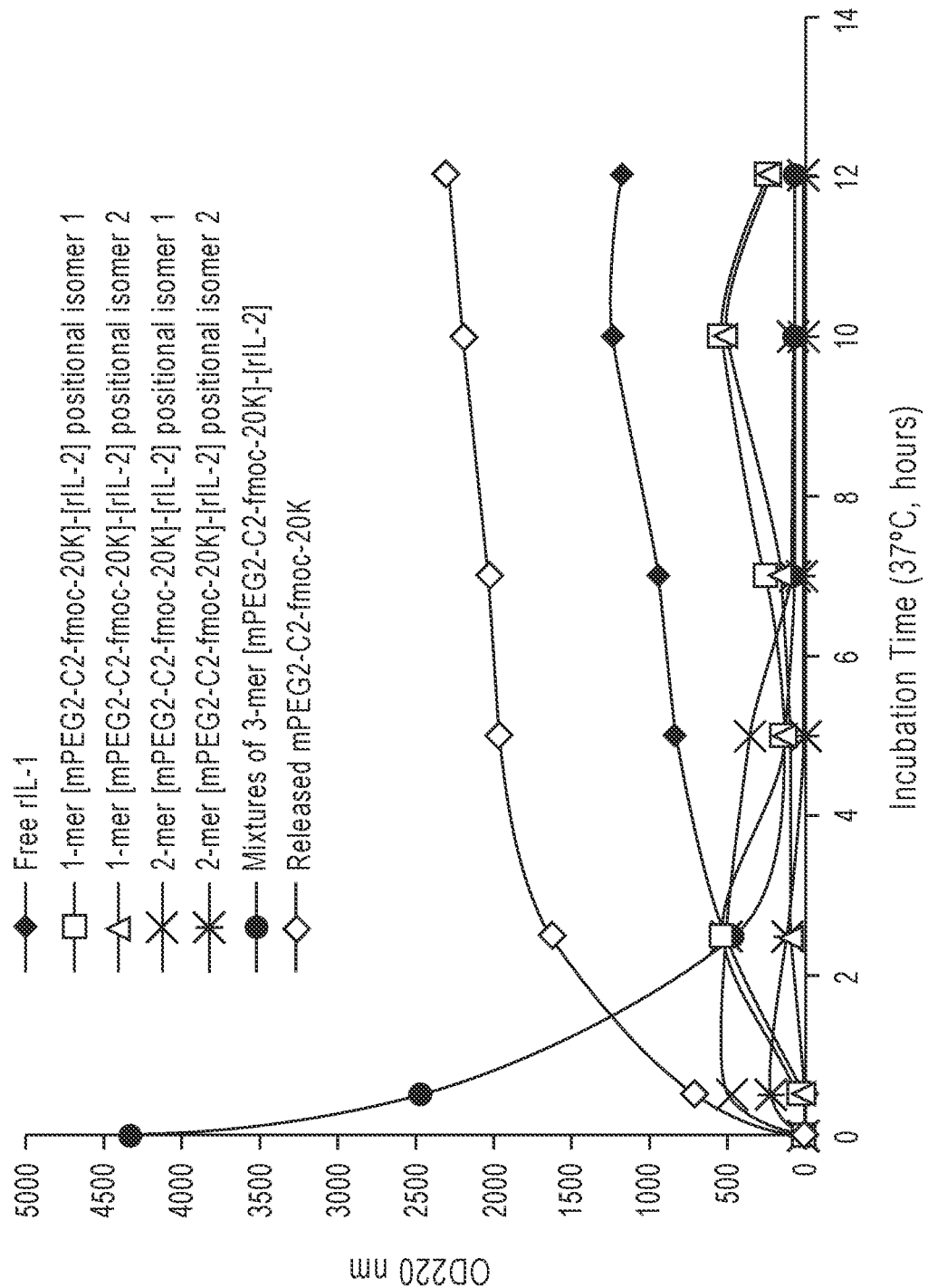
FIG. 2.3

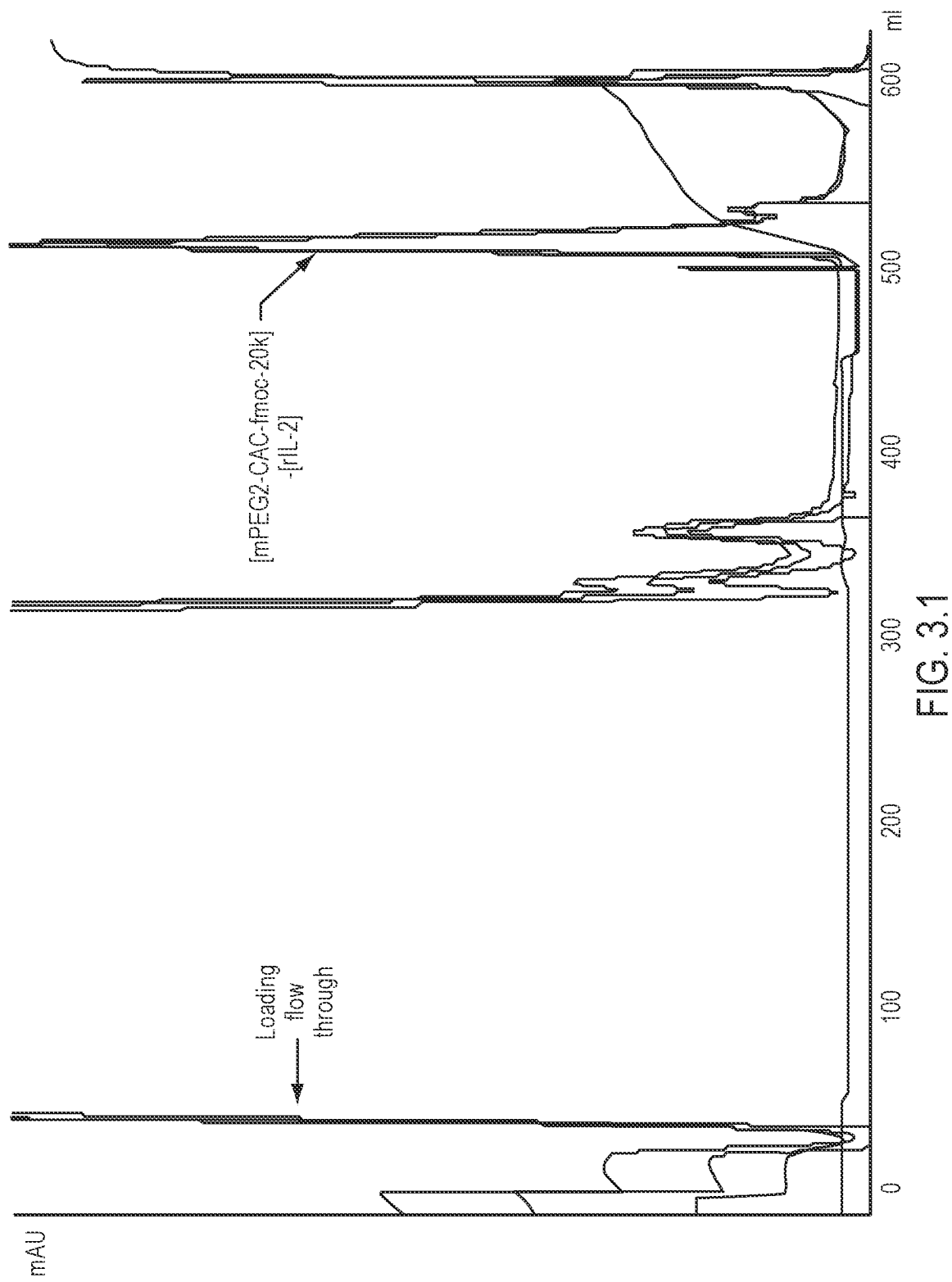
FIG. 3.1

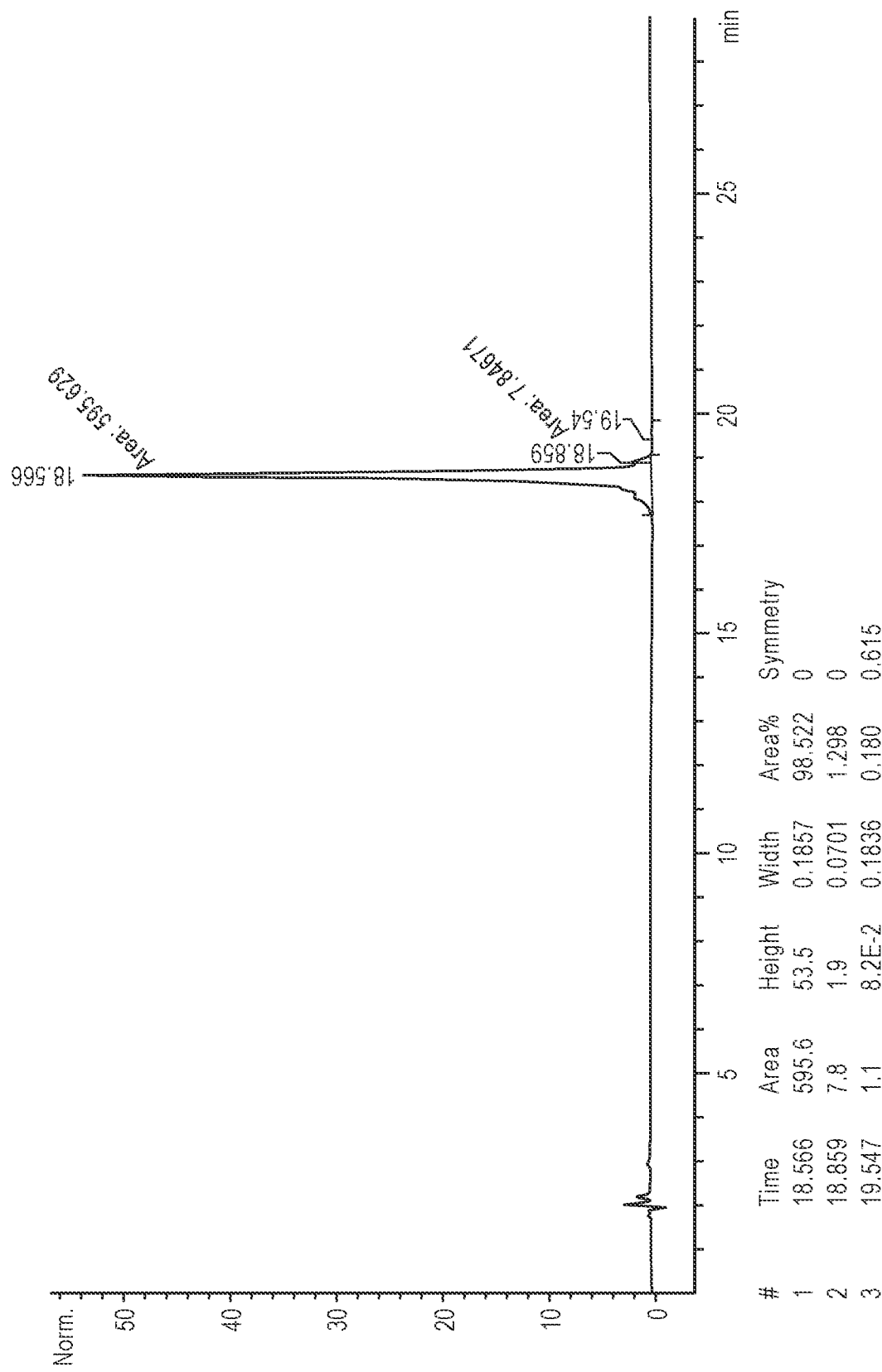
FIG. 3.2

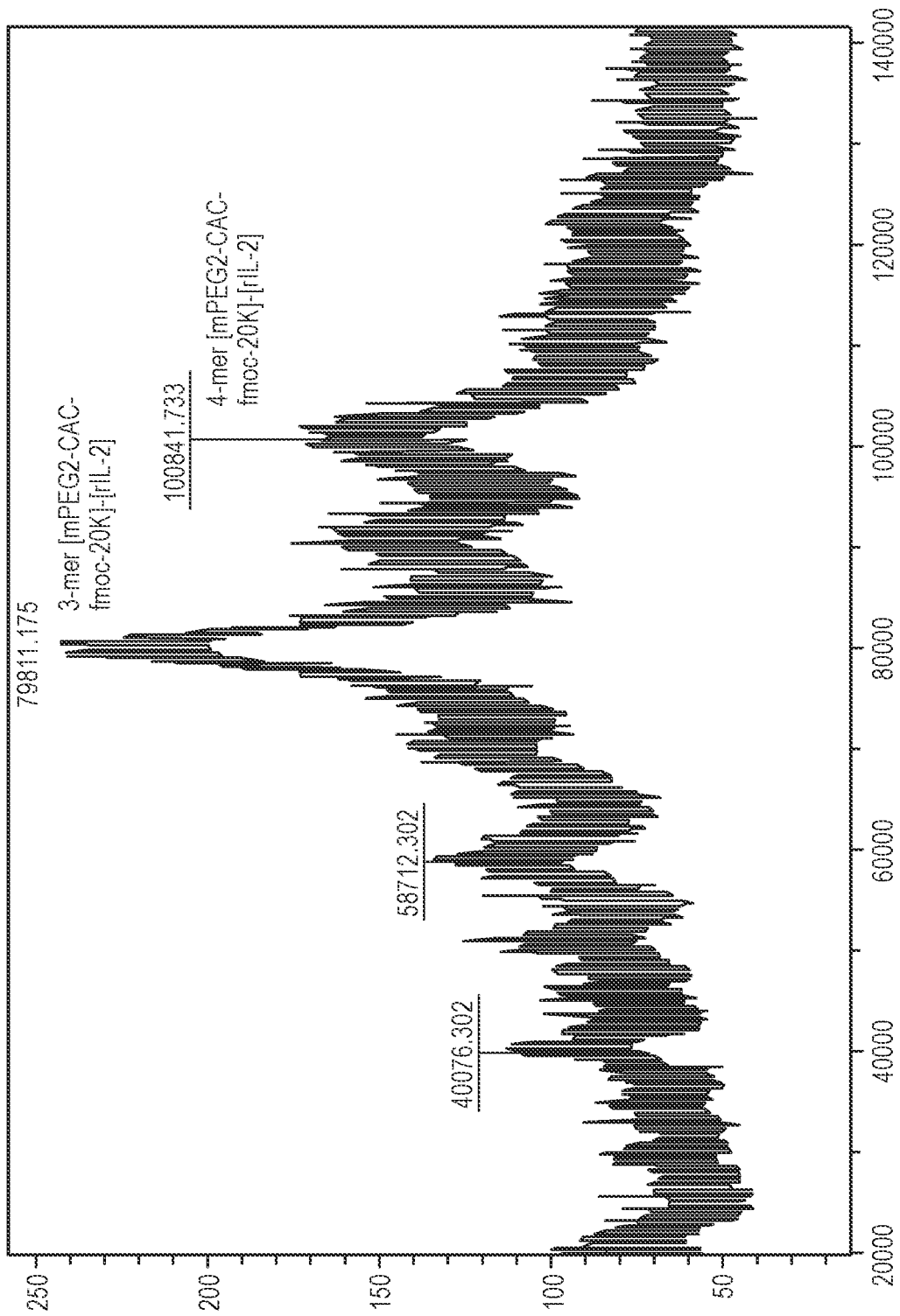
FIG. 3.3

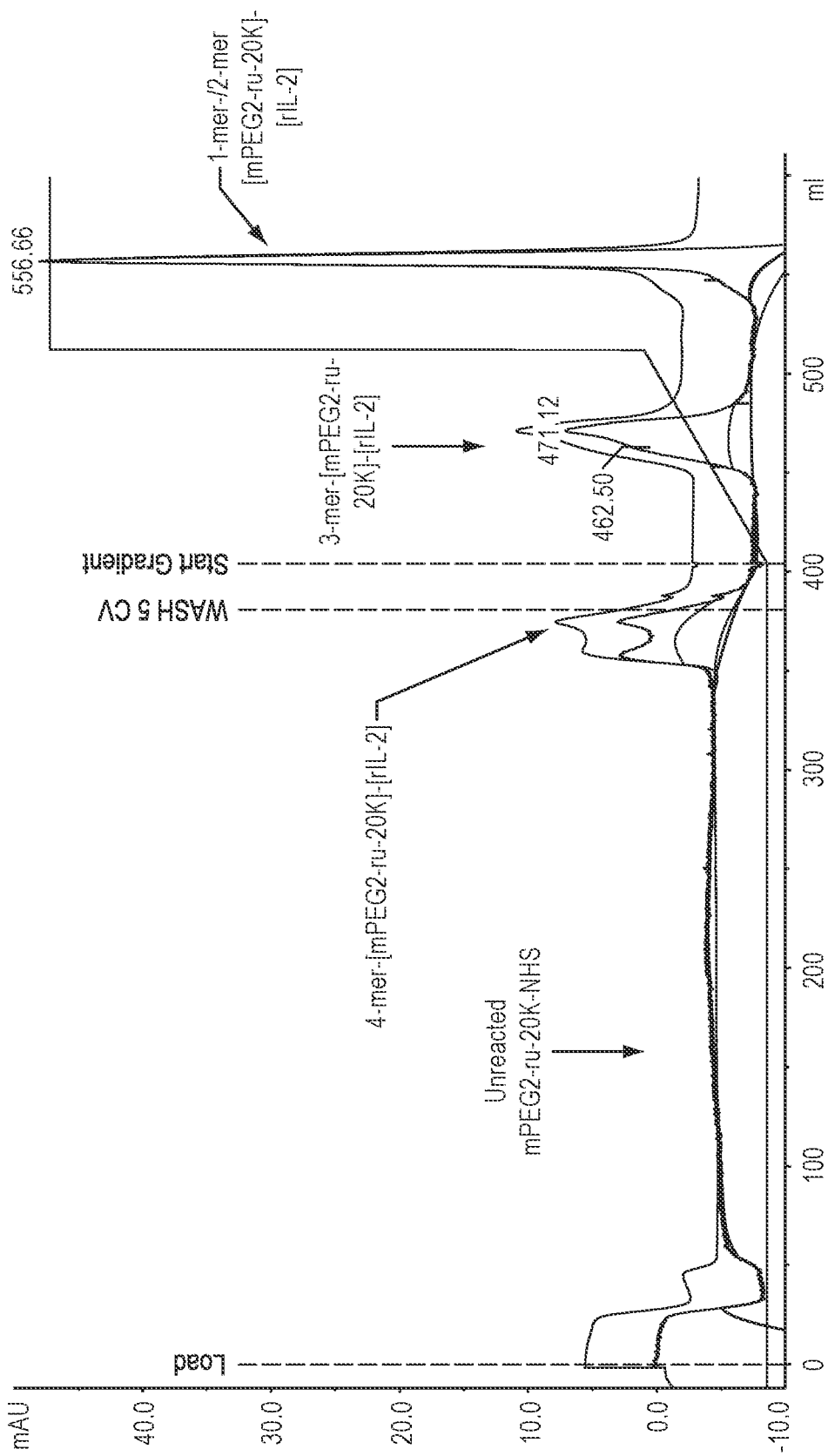
FIG. 4.1

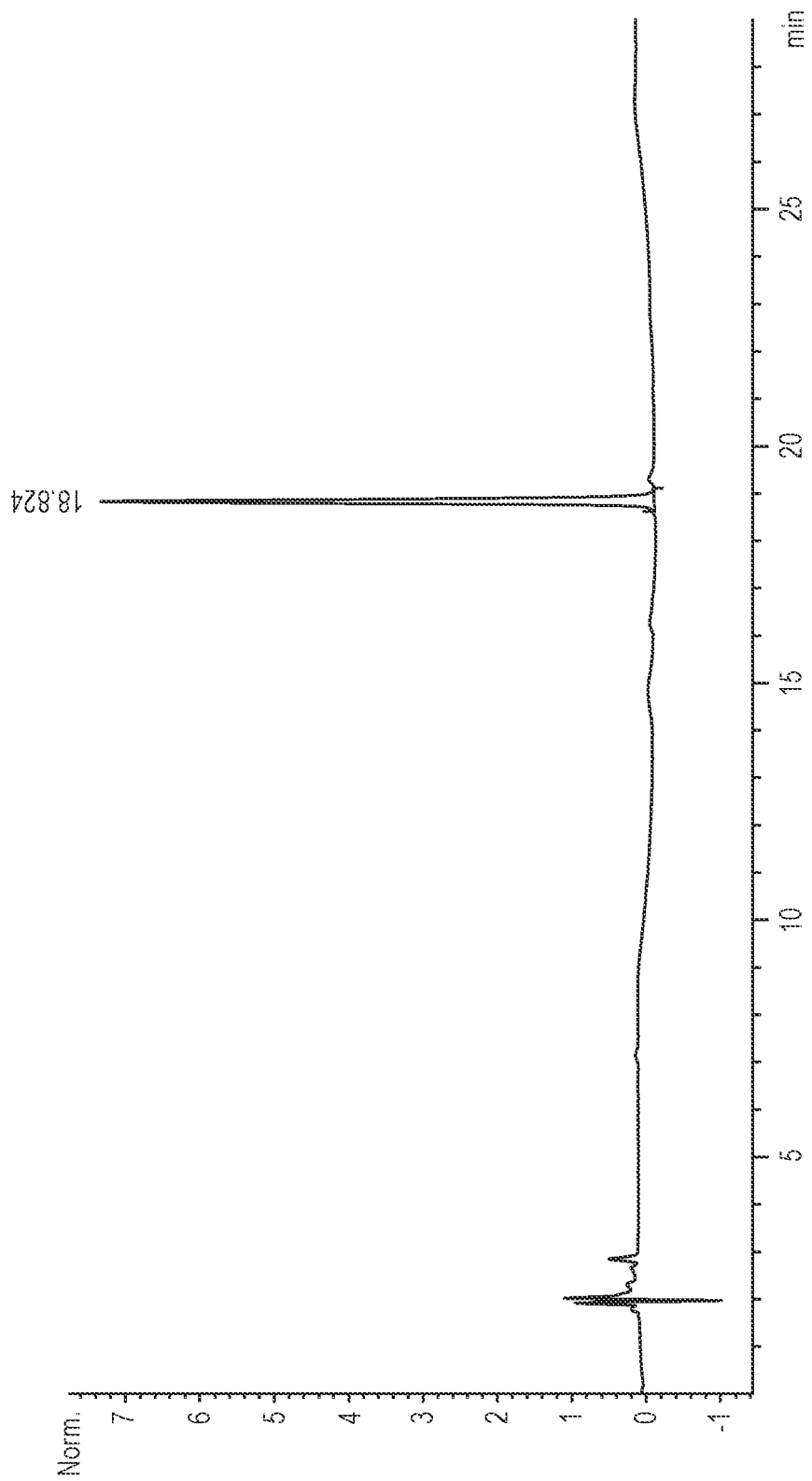
FIG. 4.2

SEQUENCE LISTING

```
<160> NUMBER OF SEQ ID NOS: 6

<210> SEQ ID NO 1
<211> LENGTH: 153
<212> TYPE: PRT
<213> ORGANISM: Homo sapiens
<220> FEATURE:
<221> NAME/KEY: SIGNAL
<222> LOCATION: (1)..(20)
<220> FEATURE:
<221> NAME/KEY: mat_peptide
<222> LOCATION: (21)..(153)

<400> SEQUENCE: 1

Met Tyr Arg Met Gln Leu Leu Ser Cys Ile Ala Leu Ser Leu Ala Leu
-20                 -15                 -10                  -5

Val Thr Asn Ser Ala Pro Thr Ser Ser Ser Thr Lys Lys Thr Gln Leu
            -1   1               5                   10

Gln Leu Glu His Leu Leu Leu Asp Leu Gln Met Ile Leu Asn Gly Ile
             15                  20                  25

Asn Asn Tyr Lys Asn Pro Lys Leu Thr Arg Met Leu Thr Phe Lys Phe
        30                  35                  40

Tyr Met Pro Lys Lys Ala Thr Glu Leu Lys His Leu Gln Cys Leu Glu
45                  50                  55                  60

Glu Glu Leu Lys Pro Leu Glu Glu Val Leu Asn Leu Ala Gln Ser Lys
                65                  70                  75
```

Asn Phe His Leu Arg Pro Arg Asp Leu Ile Ser Asn Ile Asn Val Ile
                80                  85                  90

Val Leu Glu Leu Lys Gly Ser Glu Thr Thr Phe Met Cys Glu Tyr Ala
         95                 100                 105

Asp Glu Thr Ala Thr Ile Val Glu Phe Leu Asn Arg Trp Ile Thr Phe
    110                 115                 120

Cys Gln Ser Ile Ile Ser Thr Leu Thr
125             130

<210> SEQ ID NO 2
<211> LENGTH: 133
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 3
<211> LENGTH: 132
<212> TYPE: PRT
<213> ORGANISM: Homo sapiens

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

```
Ser Thr Leu Thr
    130
```

<210> SEQ ID NO 4
<211> LENGTH: 133
<212> TYPE: PRT
<213> ORGANISM: Homo sapiens

<400> SEQUENCE: 4

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 5
<211> LENGTH: 411
<212> TYPE: DNA
<213> ORGANISM: Homo sapiens
<220> FEATURE:
<221> NAME/KEY: CDS
<222> LOCATION: (4)..(402)

<400> SEQUENCE: 5

```
cat atg ccg acc agc agc agc acc aaa aaa acc cag ctg cag ctg gaa       48
    Met Pro Thr Ser Ser Ser Thr Lys Lys Thr Gln Leu Gln Leu Glu
    1               5                   10                  15 cat ctg ctg ctg gat ctg cag atg atc ctg aac ggt atc aac aac tac       96
His Leu Leu Leu Asp Leu Gln Met Ile Leu Asn Gly Ile Asn Asn Tyr
            20                  25                  30 aaa aac ccg aaa ctg acc cgt atg ctg acc ttc aaa ttc tac atg ccg      144
Lys Asn Pro Lys Leu Thr Arg Met Leu Thr Phe Lys Phe Tyr Met Pro
        35                  40                  45 aaa aaa gca acc gaa ctg aaa cat ctg cag tgc ctg gaa gaa gaa ctg      192
Lys Lys Ala Thr Glu Leu Lys His Leu Gln Cys Leu Glu Glu Glu Leu
    50                  55                  60 aaa ccg ctg gaa gaa gtg ctg aac ctg gca cag agc aaa aac ttc cat      240
Lys Pro Leu Glu Glu Val Leu Asn Leu Ala Gln Ser Lys Asn Phe His
65                  70                  75 ctg cgt ccg cgt gat ctg atc agc aac atc aac gtg atc gtg ctg gaa      288
Leu Arg Pro Arg Asp Leu Ile Ser Asn Ile Asn Val Ile Val Leu Glu
80                  85                  90                  95 ctg aaa ggt agc gaa acc acc ttc atg tgc gaa tac gca gat gaa acc      336
Leu Lys Gly Ser Glu Thr Thr Phe Met Cys Glu Tyr Ala Asp Glu Thr
            100                 105                 110 gca acc atc gtg gaa ttt ctg aac cgt tgg atc acc ttc agc cag agc      384
Ala Thr Ile Val Glu Phe Leu Asn Arg Trp Ile Thr Phe Ser Gln Ser
```

```
                  115                 120                 125
atc atc agc acc ctg acc taagaattc                                         411
Ile Ile Ser Thr Leu Thr
            130

<210> SEQ ID NO 6
<211> LENGTH: 133
<212> TYPE: PRT
<213> ORGANISM: Homo sapiens

<400> SEQUENCE: 6

Met Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
            130
```

CONJUGATES OF AN IL-2 MOIETY AND A POLYMER

CROSS REFERENCE TO RELATED APPLICATIONS

This application is a continuation of U.S. patent application Ser. No. 16/139,957, filed Sep. 24, 2018, now U.S. Pat. No. 11,091,525, which is a divisional of U.S. patent application Ser. No. 15/835,125, filed Dec. 7, 2017, now U.S. Pat. No. 10,960,079, which is a divisional of U.S. patent application Ser. No. 13/884,901, filed Aug. 27, 2013, now U.S. Pat. No. 9,861,705, which is a 35 U.S.C. § 371 application of International Application No. PCT/US2011/060408, filed Nov. 11, 2011, designating the United States, which claims the benefit of priority under 35 U.S.C. § 119 (e) to U.S. Provisional Patent Application No. 61/413,236, filed Nov. 12, 2010, the disclosures of which are incorporated herein by reference in their entireties.

FIELD OF THE INVENTION

Among other things, one or more embodiments of the present invention relate generally to conjugates comprising an IL-2 moiety (i.e., a moiety having at least some activity similar to human IL-2) and a polymer. In addition, the invention relates to (among other things) compositions comprising conjugates, methods for synthesizing conjugates, and methods of administering a composition.

BACKGROUND OF THE INVENTION

In healthy humans, the immune system can differentiate between healthy cells and cancerous cells. Upon identifying a given cell as cancerous, the immune system typically eliminates it. Thus, when the immune system breaks down or is overwhelmed, cancers can develop resulting from a compromised immune system's inability to differentiate, and then eliminate, cancer cells. In a patient suffering from cancer, administration of an immunomodulatory protein to the patient may help return (at least in part) that patient's immune system back to normal so that her immune system's ability to eliminate cancer cells returns. In this way, the cancer may be slowed or even eliminated.

One such immunomodulatory protein used in the treatment of patients suffering from certain cancers is interleukin-2. Interleukin-2 (IL-2) is a naturally occurring cytokine that has activity as both a stimulator of natural killer cells (NK cells) and as an inducer of T-cell proliferation. In unglycosylated form, IL-2 has a molecular weight of about 15,300 Daltons (although IL-2 is found in vivo in variably glycosylated forms).

A commercially available unglycosylated human recombinant IL-2 product, aldesleukin (available as the PROLEUKIN® brand of des-alanyl-1, serine-125 human interleukin-2 from Prometheus Laboratories Inc., San Diego CA), has been approved for administration to patients suffering from metastatic renal cell carcinoma and metastatic melanoma. IL-2 has also been suggested for administration in patients suffering from or infected with hepatitis C virus (HCV), human immunodeficiency virus (HIV), acute myeloid leukemia, non-Hodgkin's lymphoma, cutaneous T-cell lymphoma, juvenile rheumatoid arthritis, atopic dermatitis, breast cancer and bladder cancer.

Even recommended doses of aldesleukin, however, can cause severe side effects, including capillary leak syndrome (CLS) and impaired neutrophil function. In view of the potential for these severe side effects, and because the recommended treatment cycle involves intravenous infusion over fifteen minutes every eight hours for fourteen doses, administration of aldesleukin occurs within a clinical setting. Moreover, the commercial formulation of aldesleukin includes the presence of sodium dodecyl sulfate, a substance that appears to be required to maintain optimal activity through conformational stability. See Arakawa et al. (1994) *Int. J. Peptide Protein Res.* 43:583-587.

Attempts at addressing the toxicity concerns of IL-2 have been tried. In one approach, formulation approaches have been attempted. See, for example, U.S. Pat. No. 6,706,289 and international patent application publication WO 02/00243 and WO 99/60128. In other approaches, certain conjugates of IL-2 have been suggested. See, for example, U.S. Pat. Nos. 4,766,106, 5,206,344, 5,089,261 and 4,902,502.

Notwithstanding these approaches, however, there remains a need for conjugates of IL-2. Among other things, one or more embodiments of the present invention is therefore directed to such conjugates as well as compositions comprising the conjugates and related methods as described herein, which are believed to be new and completely unsuggested by the art.

SUMMARY OF THE INVENTION

Accordingly, in one or more embodiments of the invention, a conjugate is provided, the conjugate comprising a residue of an IL-2 moiety covalently attached to a water-soluble polymer.

In one or more embodiments of the invention, a conjugate is provided, the conjugate comprising a residue of an IL-2 moiety covalently attached to a water-soluble polymer, wherein the residue of the IL-2 moiety is covalently attached to the water-soluble polymer via a releasable linkage.

In one or more embodiments of the invention, a conjugate is provided, the conjugate comprising a residue of an IL-2 moiety covalently attached to a water-soluble polymer, wherein the IL-2 moiety is a precursor IL-2 moiety.

In one or more embodiments of the invention, a conjugate is provided, the conjugate comprising a residue of an IL-2 moiety covalently attached to a water-soluble polymer, wherein the IL-2 moiety is a non-precursor IL-2 moiety.

In one or more embodiments of the invention, a method for delivering a conjugate is provided, the method comprising the step of subcutaneously administering to a patient a composition comprised of a conjugate of a residue of an IL-2 and a water-soluble polymer.

In one or more embodiments of the invention, an isolated nucleic acid molecule is provided, the isolated nucleic acid molecule encoding an IL-2 moiety, wherein said nucleic acid molecule includes a sequence having substantial (e.g., at least 80%) sequence identify to the sequence set forth in SEQ ID NO: 5.

In one or more embodiments of the invention, an expression vector is provided, the expression vector (e.g., an in vitro expression vector) comprising a nucleic acid molecule provided herein.

In one or more embodiments of the invention, a host cell is provided, the host cell (e.g., an in vitro host cell) comprising an expression vector as provided herein.

BRIEF DESCRIPTION OF THE DRAWINGS

FIG. 1 provides the DNA sequence and resulting amino acid sequence (SEQ ID NO:5) of a gene whose synthesis is further described in Example 1.

FIG. 2.1 is a representation of a typical chromatogram following cation exchange chromatography of [mPEG2-C2-fmoc-20K]-[rIL-2] prepared following the procedure set forth in Example 2.

FIG. 2.2 is a representation of a chromatogram following reverse phase HPLC analysis of [mPEG2-C2-fmoc-20K]-[rIL-2], as further described in Example 2.

FIG. 2.3 is a plot of the release profile of various conjugates prepared in accordance with the procedure set forth in Example 2.

FIG. 3.1 is a representation of a typical chromatogram following cation exchange chromatography of [mPEG2-CAC-fmoc-20K]-[rIL-2] prepared following the procedures set forth in Example 3.

FIG. 3.2 is a representation of a chromatogram following reverse phase HPLC analysis of [mPEG2-CAC-fmoc-20K]-[rIL-2], as further described in Example 3.

FIG. 3.3 is a representation of the results following MALDI-TOF analysis of the various conjugates prepared in accordance with the procedures set forth in Example 3.

FIG. 4.1 is a representation of a typical chromatogram following cation exchange chromatography of [mPEG2-ru-20K]-[rIL-2] prepared following the procedures set forth in Example 4.

FIG. 4.2 is a representation of a chromatogram following reverse phase HPLC analysis of [mPEG2-ru-20K]-[rIL-2], as further described in Example 4.

DETAILED DESCRIPTION OF THE INVENTION

Figure 5:
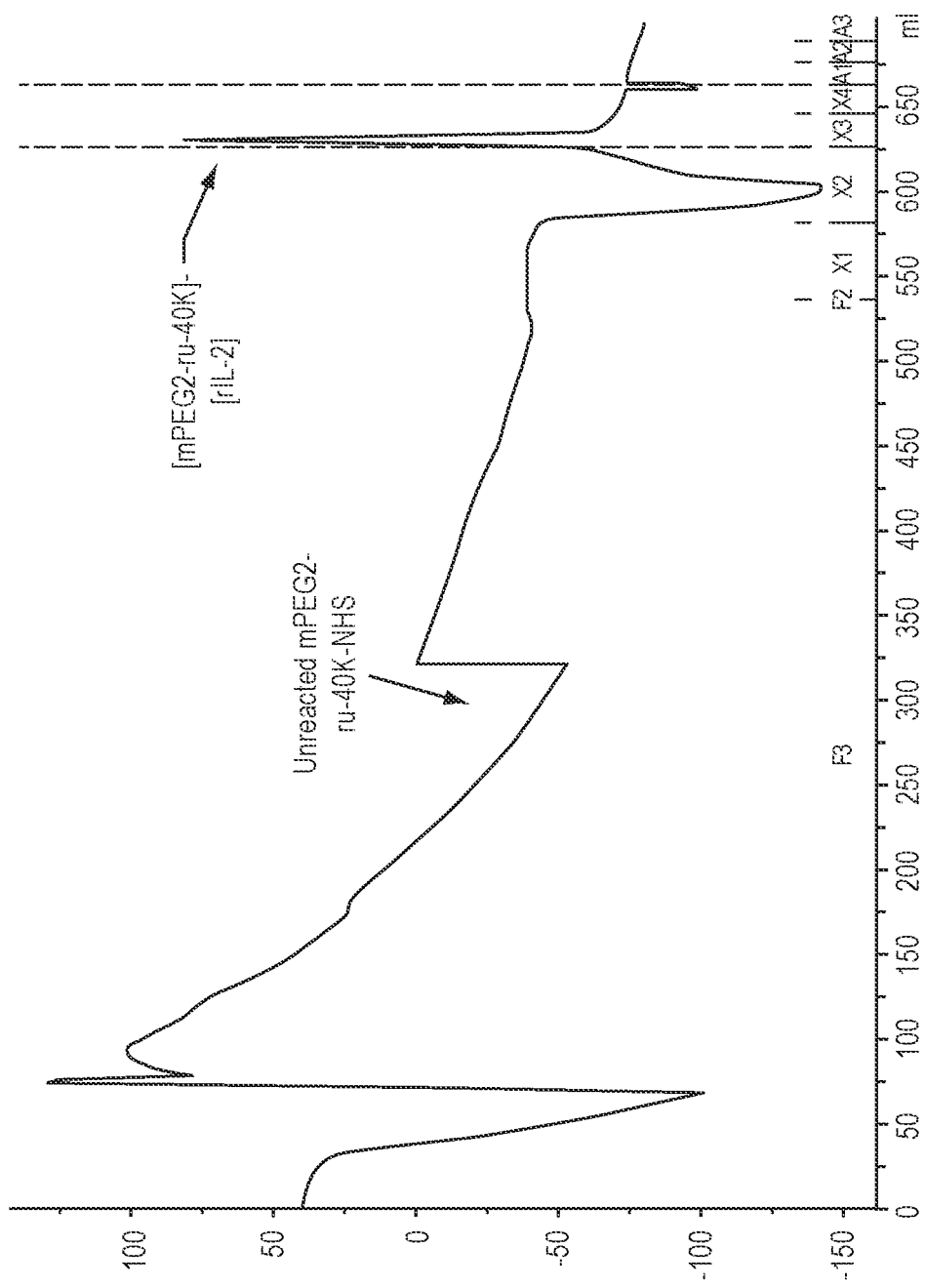
FIG. 5 is a representation of a chromatogram following cation exchange chromatography of [mPEG2-ru-40K]-[rIL-2], as further described in Example 5.

Before describing one or more embodiments of the present invention in detail, it is to be understood that this invention is not limited to the particular polymers, synthetic techniques, IL-2 moieties, and the like, as such may vary.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to "an optional excipient" refers to a single optional excipient as well as two or more of the same or different optional excipients, and the like.

In describing and claiming one or more embodiments of the present invention, the following terminology will be used in accordance with the definitions described below.

"PEG," "polyethylene glycol" and "poly(ethylene glycol)" as used herein, are interchangeable and encompass any nonpeptidic water-soluble poly(ethylene oxide). Typically, PEGs for use in accordance with the invention comprise the following structure "—$(OCH_2CH_2)_n$—" where (n) is 2 to 4000. As used herein, PEG also includes "—$CH_2CH_2$—O$(CH_2CH_2O)_n$—$CH_2CH_2$—" and "—$(OCH_2CH_2)_nO$—," depending upon whether or not the terminal oxygens have been displaced, e.g., during a synthetic transformation. Throughout the specification and claims, it should be remembered that the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin. The end-capping group may also include a targeting moiety, such that the polymer—as well as anything, e.g., an IL-2 moiety, attached thereto—can preferentially localize in an area of interest.

"Non-naturally occurring" with respect to a polymer as described herein, means a polymer that in its entirety is not found in nature. A non-naturally occurring polymer may, however, contain one or more monomers or segments of monomers that are naturally occurring, so long as the overall polymer structure is not found in nature.

The term "water soluble" as in a "water-soluble polymer" polymer is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The terms "active," "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to a bond or an atom or a collection of atoms optionally used to link interconnecting moieties such as a terminus of a polymer segment and an IL-2 moiety or an electrophile or nucleophile of an IL-2 moiety. The spacer moiety may be hydrolytically stable or may include a physiologically hydrolyzable or enzymatically degradable linkage. Unless the context clearly dictates otherwise, a spacer moiety optionally exists between any two elements of a compound (e.g., the provided conjugates comprising a residue of IL-2 moiety and water-soluble polymer can be attached directly or indirectly through a spacer moiety).

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —OR group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include akyl, substituted alkyl, aryl, and substituted aryl.

"Electrophile" and "electrophilic group" refer to an ion or atom or collection of atoms, which may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, which is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a polymer-(IL-2) moiety conjugate that is needed to provide a desired level of the conjugate (or corresponding unconjugated IL-2 moiety) in the bloodstream or in the target tissue. The precise amount will depend upon numerous factors, e.g., the particular IL-2 moiety, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

The term "IL-2 moiety," as used herein, refers to a moiety having human IL-2 activity. The IL-2 moiety will also have at least one electrophilic group or nucleophilic group suitable for reaction with a polymeric reagent. In addition, the term "IL-2 moiety" encompasses both the IL-2 moiety prior to conjugation as well as the IL-2 moiety residue following conjugation. As will be explained in further detail below, one of ordinary skill in the art can determine whether any given moiety has IL-2 activity. Proteins comprising an amino acid sequence corresponding to any one of SEQ ID NOs: 1 through 4 is an IL-2 moiety, as well as any protein or polypeptide substantially homologous thereto. As used herein, the term "IL-2 moiety" includes such proteins modified deliberately, as for example, by site directed mutagenesis or accidentally through mutations. These terms also include analogs having from 1 to 6 additional glycosylation sites, analogs having at least one additional amino acid at the carboxy terminal end of the protein wherein the additional amino acid(s) includes at least one glycosylation site, and analogs having an amino acid sequence which includes at least one glycosylation site. The term includes both natural and recombinantly produced moieties.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 80 percent (more preferably greater than 85 percent, still more preferably greater than 90 percent, with greater than 95 percent being most preferred) homology, equivalent biological activity (although not necessarily equivalent strength of biological activity), and equivalent expression characteristics are considered substantially homologous. For purposes of determining homology, truncation of the mature sequence should be disregarded. Exemplary IL-2 moieties for use herein include those sequences that are substantially homologous SEQ ID NO:2.

The term "fragment" means any protein or polypeptide having the amino acid sequence of a portion or fragment of an IL-2 moiety, and which has the biological activity of IL-2. Fragments include proteins or polypeptides produced by proteolytic degradation of an IL-2 moiety as well as proteins or polypeptides produced by chemical synthesis by methods routine in the art.

The term "patient," refers to a living organism suffering from or prone to a condition that can be prevented or treated by administration of an active agent (e.g., conjugate), and includes both humans and animals.

"Optional" or "optionally" means that the subsequently described circumstance may or may not occur, so that the description includes instances where the circumstance occurs and instances where it does not.

"Substantially" means nearly totally or completely, for instance, satisfying one or more of the following: greater than 50%, 51% or greater, 75% or greater, 80% or greater, 90% or greater, and 95% or greater of the condition.

As used herein, "sequence identity" is determined by comparing the sequence of the reference DNA sequence to that portion of another DNA sequence so aligned so as to maximize overlap between the two sequences while minimizing sequence gaps, wherein any overhanging sequences between the two sequences are ignored. With respect to any sequence identity described herein, it is preferred that at least 80%, more preferred, 85%, yet more preferred 90%, still yet more preferred 95% sequence identity, with 96%, 97%, 98%, and 99% sequence identities being most preferred.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Turning to one or more embodiments of the invention, a conjugate is provided, the conjugate comprising a residue of an IL-2 moiety covalently attached (either directly or through a spacer moiety) to a water-soluble polymer. The conjugates of the invention will have one or more of the following features.

The IL-2 Moiety

As previously stated, the conjugate generically comprises a residue of an IL-2 moiety covalently attached, either directly or through a spacer moiety, to a water-soluble polymer. As used herein, the term "IL-2 moiety" shall refer to the IL-2 moiety prior to conjugation as well as to the IL-2 moiety following attachment to a nonpeptidic, water-soluble polymer. It will be understood, however, that when the original IL-2 moiety is attached to a nonpeptidic, water-soluble polymer, the IL-2 moiety is slightly altered due to the presence of one or more covalent bonds associated with linkage to the polymer(s). Often, this slightly altered form of the IL-2 moiety attached to another molecule is referred to a "residue" of the IL-2 moiety.

The IL-2 moiety can be derived from non-recombinant methods and from recombinant methods and the invention is not limited in this regard. In addition, the IL-2 moiety can be derived from human sources, animal sources, and plant sources.

The IL-2 moiety can be derived non-recombinantly. For example, it is possible to isolate IL-2 from biological systems and otherwise obtain IL-2 from cultured media. See, for example, the procedures described in U.S. Pat. No. 4,401,756 and in Pauly et al. (1984) *J. Immunol Methods* 75(1):73-84.

The IL-2 moiety can be derived from recombinant methods. See, for example, U.S. Pat. No. 5,614,185, the disclosure and the Experimental provided herein.

Any IL-2 moiety obtained non-recombinant and recombinant approaches can be used as an IL-2 moiety in preparing the conjugates described herein.

The IL-2 moiety can be expressed in bacterial [e.g., *E. coli*, see, for example, Fischer et al. (1995) *Biotechnol. Appl. Biochem.* 21(3):295-311], mammalian [see, for example, Kronman et al. (1992) *Gene* 121:295-304], yeast [e.g., *Pichia pastoris*, see, for example, Morel et al. (1997) *Biochem. J.* 328(1):121-129], and plant [see, for example, Mor et al. (2001) *Biotechnol. Bioeng.* 75(3):259-266] expression systems. The expression can occur via exogenous expression (when the host cell naturally contains the desired genetic coding) or via endogenous expression.

Although recombinant-based methods for preparing proteins can differ, recombinant methods typically involve constructing the nucleic acid encoding the desired polypeptide or fragment, cloning the nucleic acid into an expression vector, transforming a host cell (e.g., plant, bacteria, yeast, transgenic animal cell, or mammalian cell such as Chinese hamster ovary cell or baby hamster kidney cell), and expressing the nucleic acid to produce the desired polypeptide or fragment. Methods for producing and expressing recombinant polypeptides in vitro and in prokaryotic and eukaryotic host cells are known to those of ordinary skill in the art.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be purified by lysing the host cells, separating the polypeptide, e.g., by ion-exchange chromatography, affinity binding approaches, hydrophobic interaction approaches, and thereafter identify by MALDI or western blot, and collecting the polypeptide. These and other methods for identifying and purifying recombinant polypeptides are known to those of ordinary skill in the art. In one or more embodiments of the invention, however, the IL-2 moiety is not in the form of a fusion protein.

Depending on the system used to express proteins having IL-2 activity, the IL-2 moiety can be unglycosylated or glycosylated and either may be used. That is, the IL-2 moiety can be unglycosylated or the IL-2 moiety can be glycosylated. In one or more embodiments of the invention, the IL-2 moiety is unglycosylated.

The IL-2 moiety can advantageously be modified to include and/or substitute one or more amino acid residues such as, for example, lysine, cysteine and/or arginine, in order to provide facile attachment of the polymer to an atom within the side chain of the amino acid. An example of substitution of an IL-2 moiety is described in U.S. Pat. No. 5,206,344. In addition, the IL-2 moiety can be modified to include a non-naturally occurring amino acid residue. Techniques for adding amino acid residues and non-naturally occurring amino acid residues are well known to those of ordinary skill in the art. Reference is made to J. March, Advanced Organic Chemistry: Reactions Mechanisms and Structure, 4th Ed. (New York: Wiley-Interscience, 1992).

In addition, the IL-2 moiety can advantageously be modified to include attachment of a functional group (other than through addition of a functional group-containing amino acid residue). For example, the IL-2 moiety can be modified to include a thiol group. In addition, the IL-2 moiety can be modified to include an N-terminal alpha carbon. In addition, the IL-2 moiety can be modified to include one or more carbohydrate moieties. In addition, the IL-2 moiety can be modified to include an aldehyde group. In addition, the IL-2 moiety can be modified to include a ketone group. In some embodiments of the invention, it is preferred that the IL-2 moiety is not modified to include one or more of a thiol group, an N-terminal alpha carbon, carbohydrate, adehyde group and ketone group.

Exemplary IL-2 moieties are described in the literature and in, for example, U.S. Pat. Nos. 5,116,943, 5,153,310, 5,635,597, 7,101,965 and 7,567,215 and U.S. Patent Application Publication Nos. 2010/0036097 and 2004/0175337. Preferred IL-2 moieties include those having an amino acid sequence comprising sequences selected from the group consisting of SEQ ID NOs: 1 through 4, and sequences substantially homologous thereto. A preferred IL-2 moiety has the amino acid sequence corresponding to SEQ ID NO:3.

In some instances, the IL-2 moiety will be in a "monomer" form, wherein a single expression of the corresponding peptide is organized into a discrete unit. In other instances, the IL-2 moiety will be in the form of a "dimer" (e.g., a dimer of recombinant IL-2) wherein two monomer forms of the protein are associated (e.g., by disulfide bonding) to each other. For example, in the context of a dimer of recombinant human IL-2, the dimer may be in the form of two monomers associated to each other by a disulfide bond formed from each monomer's Cys125 residue.

In addition, precursor forms IL-2 can be used as the IL-2 moiety. An exemplary precursor form of IL-2 has the sequence of SEQ ID NO:1.

Truncated versions, hybrid variants, and peptide mimetics of any of the foregoing sequences can also serve as the IL-2 moiety. Biologically active fragments, deletion variants, substitution variants or addition variants of any of the foregoing that maintain at least some degree of IL-2 activity can also serve as an IL-2 moiety.

For any given peptide or protein moiety, it is possible to determine whether that moiety has IL-2 activity. Various methods for determining the in vitro IL-2 activity are described in the art. An exemplary approach is the CTTL-2 cell proliferation assay described in the experimental below. An exemplary approach is described in Moreau et al. (1995) *Mol. Immunol.* 32:1047-1056). Briefly, in a non-specific binding assay, a proposed IL-2 moiety is allowed to preincubate for one hour at 4° C. in the presence of a cell line bearing a receptor of IL-2. Thereafter, $^{125}$I-labelled IL-2 is allowed to incubate in the system for three hours at 4° C. Data is expressed as % inhibitory capacity of the proposed IL-2 moiety activity versus wild-type IL-2. Other methodologies known in the art can also be used to assess IL-2 function, including electrometry, spectrophotometry, chromatography, and radiometric methodologies.

The Water-Soluble Polymer

As previously discussed, each conjugate comprises an IL-2 moiety attached to a water-soluble polymer. With respect to the water-soluble polymer, the water-soluble polymer is nonpeptidic, nontoxic, non-naturally occurring and biocompatible. With respect to biocompatibility, a substance is considered biocompatible if the beneficial effects associated with use of the substance alone or with another substance (e.g., an active agent such as an IL-2 moiety) in connection with living tissues (e.g., administration to a patient) outweighs any deleterious effects as evaluated by a clinician, e.g., a physician. With respect to non-immunogenicity, a substance is considered non-immunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the nonpeptidic water-soluble polymer is biocompatible and non-immunogenic.

Further, the polymer is typically characterized as having from 2 to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines ("POZ") (which are described in WO 2008/106186), poly(N-acryloylmorpholine), and combinations of any of the foregoing.

The water-soluble polymer is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the IL-2 moiety. Thus, a polymeric reagent will possess a reactive group for reaction with the IL-2 moiety. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16:157-182. Exemplary activating groups suitable for coupling to an IL-2 moiety include hydroxyl, maleimide, ester, acetal, ketal, amine, carboxyl, aldehyde, aldehyde hydrate, ketone, vinyl ketone, thione, thiol, vinyl sulfone, hydrazine, among others.

Preferably, the polymeric reagent used to prepare the conjugates described herein is prepared without the use of phosgene. Such an approach stands in contrast to, for example, the disclosure set forth in U.S. Pat. No. 4,902,502, which specifically describes forming a chloroformate and subsequent used to form a PEG active ester, which is then reacted with IL-2. Use of phosgene leads to the formation of hydrogen chloride, which can lead to chain cleavage in the polymer, thereby increasing impurities, which may not be able to be removed using conventional techniques. Thus, without wishing to be bound by theory, IL-2 moiety conjugates prepared from polymeric reagents formed without the use of phosgene provides higher quality compositions that are substantially absent polymer chain degradation products. Also, in one or more embodiments, the spacer moiety between the water-soluble polymer and the IL-2 moiety is not a carbamate-containing spacer moiety.

Typically, the weight-average molecular weight of the water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

When used as the polymer, PEGS will typically comprise a number of (OCH$_2$CH$_2$) monomers [or (CH$_2$CH$_2$O) monomers, depending on how the PEG is defined]. As used throughout the description, the number of repeating units is identified by the subscript "n" in "(OCH$_2$CH$_2$)$_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

One particularly preferred polymer for use in the invention is an end-capped polymer, that is, a polymer having at least one terminus capped with a relatively inert group, such as a lower C$_{1-6}$ alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy (—OCH$_3$) group, while the other terminus is a hydroxyl or other functional group that can be optionally chemically modified.

In one form useful in one or more embodiments of the present invention, free or unbound PEG is a linear polymer terminated at each end with hydroxyl groups:

HO—CH$_2$CH$_2$O—(CH$_2$CH$_2$O)$_n$—CH$_2$CH$_2$—OH, wherein (n) typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

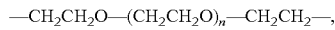
—CH$_2$CH$_2$O—(CH$_2$CH$_2$O)$_n$—CH$_2$CH$_2$—, wherein (n) is as defined as above.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below.

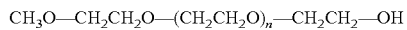
CH$_3$O—CH$_2$CH$_2$O—(CH$_2$CH$_2$O)$_n$—CH$_2$CH$_2$—OH wherein (n) is as described above.

Multi-armed or branched PEG molecules, such as those described in U.S. Pat. No. 5,932,462, can also be used as the PEG polymer. For example, PEG can have the structure:

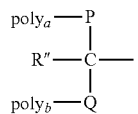

wherein:
poly$_a$ and poly$_b$ are PEG backbones (either the same or different), such as methoxy poly(ethylene glycol);
R″ is a nonreactive moiety, such as H, methyl or a PEG backbone; and
P and Q are nonreactive linkages. In a preferred embodiment, the branched PEG polymer is methoxy poly(ethylene glycol) disubstituted lysine. Depending on the specific IL-2 moiety used, the reactive ester functional group of the disubstituted lysine may be further modified to form a functional group suitable for reaction with the target group within the IL-2 moiety.

In addition, the PEG can comprise a forked PEG. An example of a forked PEG is represented by the following structure:

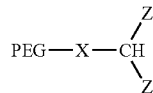

wherein: X is a spacer moiety of one or more atoms and each Z is an activated terminal group linked to CH by a chain of atoms of defined length. International Patent Application Publication WO 99/45964 discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above-described polymers. For example, PEG can be prepared with ester linkages in the polymer that are subject to hydrolysis. As shown below, this hydrolysis results in cleavage of the polymer into fragments of lower molecular weight:

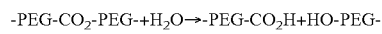
-PEG-CO$_2$-PEG-+H$_2$O→-PEG-CO$_2$H+HO-PEG-

Other hydrolytically degradable linkages, useful as a degradable linkage within a polymer backbone and/or as a degradable linkage to an IL-2 moiety, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Such optional features of the conjugate, i.e., the introduction of one or more degradable linkages into the polymer chain or to the IL-2 moiety, may provide for additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 10,000, wherein the conjugate possesses essentially no bioactivity) may be administered, which is released to generate a bioactive conjugate possessing a portion of the original PEG chain. In this way, the properties of the conjugate can be more effectively tailored to balance the bioactivity of the conjugate over time.

The water-soluble polymer associated with the conjugate can also be "releasable." That is, the water-soluble polymer releases (either through hydrolysis, enzymatic processes, catalytic processes or otherwise), thereby resulting in the unconjugated IL-2 moiety. In some instances, releasable polymers detach from the IL-2 moiety in vivo without leaving any fragment of the water-soluble polymer. In other instances, releasable polymers detach from the IL-2 moiety in vivo leaving a relatively small fragment (e.g., a succinate tag) from the water-soluble polymer. An exemplary cleavable polymer includes one that attaches to the IL-2 moiety via a carbonate linkage.

Those of ordinary skill in the art will recognize that the foregoing discussion concerning nonpeptidic and water-soluble polymer is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

As described above, a conjugate of the invention comprises a water-soluble polymer covalently attached to an IL-2 moiety. Typically, for any given conjugate, there will be one to three water-soluble polymers covalently attached to one or more moieties having IL-2 activity. In some instances, however, the conjugate may have 1, 2, 3, 4, 5, 6, 7, 8 or more water-soluble polymers individually attached to an IL-2 moiety. Any given water-soluble polymer may be covalently attached to either an amino acid of the IL-2 moiety, or, when the IL-2 moiety is (for example) a glycoprotein, to a carbohydrate of the IL-2 moiety. Attachment to a carbohydrate may be carried out, e.g., using metabolic functionalization employing sialic acid-azide chemistry [Luchansky et al. (2004) *Biochemistry* 43(38):12358-12366] or other suitable approaches such as the use of glycidol to facilitate the introduction of aldehyde groups [Heldt et al. (2007) *European Journal of Organic Chemistry* 32:5429-5433].

The particular linkage within the moiety having IL-2 activity and the polymer depends on a number of factors. Such factors include, for example, the particular linkage chemistry employed, the particular IL-2 moiety, the available functional groups within the IL-2 moiety (either for attachment to a polymer or conversion to a suitable attachment site), the presence of additional reactive functional groups within the IL-2 moiety, and the like.

The conjugates of the invention can be, although not necessarily, prodrugs, meaning that the linkage between the polymer and the IL-2 moiety is releasable to allow release of the parent moiety. Exemplary releasable linkages include carboxylate ester, phosphate ester, thiol ester, anhydrides, acetals, ketals, acyloxyalkyl ether, imines, orthoesters, peptides and oligonucleotides. Such linkages can be readily prepared by appropriate modification of either the IL-2 moiety (e.g., the carboxyl group C terminus of the protein, or a side chain hydroxyl group of an amino acid such as serine or threonine contained within the protein, or a similar functionality within the carbohydrate) and/or the polymeric reagent using coupling methods commonly employed in the art. Most preferred, however, are releaseable linkages that are readily formed by reaction of a suitably activated polymer with a non-modified functional group contained within the moiety having IL-2 activity.

Alternatively, a hydrolytically stable linkage, such as an amide, urethane (also known as carbamate), amine, thioether (also known as sulfide), or urea (also known as carbamide) linkage can also be employed as the linkage for coupling the IL-2 moiety. Again, a preferred hydrolytically stable linkage is an amide. In one approach, a water-soluble polymer bearing an activated ester can be reacted with an amine group on the IL-2 moiety to thereby result in an amide linkage.

The conjugates (as opposed to an unconjugated IL-2 moiety) may or may not possess a measurable degree of IL-2 activity. That is to say, a polymer-IL-2 moiety conjugate in accordance with the invention will possesses anywhere from about 0.1% to about 100% of the bioactivity of the unmodified parent IL-2 moiety. In some instances, the polymer-IL-2 moiety conjugates may have greater than 100% bioactivity of the unmodified parent IL-2 moiety. Preferably, conjugates possessing little or no IL-2 activity contain a hydrolyzable linkage connecting the polymer to the moiety, so that regardless of the lack (or relatively lack) of activity in the conjugate, the active parent molecule (or a derivative thereof) is released upon aqueous-induced cleavage of the hydrolyzable linkage. Such activity may be determined using a suitable in-vivo or in-vitro model, depending upon the known activity of the particular moiety having IL-2 activity employed.

For conjugates possessing a hydrolytically stable linkage that couples the moiety having IL-2 activity to the polymer, the conjugate will typically possess a measurable degree of bioactivity. For instance, such conjugates are typically characterized as having a bioactivity satisfying one or more of the following percentages relative to that of the unconjugated IL-2 moiety: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, at least about 97%, at least about 100%, and more than 105% (when measured in a suitable model, such as those well known in the art). Preferably, conjugates having a hydrolytically stable linkage (e.g., an amide linkage) will possess at least some degree of the bioactivity of the unmodified parent moiety having IL-2 activity.

Exemplary conjugates in accordance with the invention will now be described. Typically, such an IL-2 moiety is expected to share (at least in part) a similar amino acid sequence as the sequence provided in at least one of SEQ ID NOs: 1 through 4. Thus, while reference will be made to specific locations or atoms within SEQ ID NOs: 1 through 4, such a reference is for convenience only and one having ordinary skill in the art will be able to readily determine the corresponding location or atom in other moieties having IL-2 activity. In particular, the description provided herein for native human IL-2 is often applicable to fragments, deletion variants, substitution variants or addition variants of any of the foregoing.

Amino groups on IL-2 moieties provide a point of attachment between the IL-2 moiety and the water-soluble polymer. Using the amino acid sequence provided in SEQ ID NOs: 1 through 4, it is evident that there are several lysine residues in each having an ε-amino acid that may be available for conjugation. Further, the N-terminal amine of any protein can also serve as a point of attachment.

There are a number of examples of suitable polymeric reagents useful for forming covalent linkages with available amines of an IL-2 moiety. Specific examples, along with the corresponding conjugate, are provided in Table 1, below. In the table, the variable (n) represents the number of repeating monomeric units and "—NH-(IL-2)" represents the residue of the IL-2 moiety following conjugation to the polymeric reagent. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 1

Amine-Selective Polymeric Reagents and the IL-2 Moiety Conjugate Formed Therefrom

| Polymeric Reagent | Corresponding Conjugate |
|---|---|
| 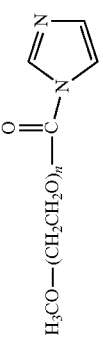<br>mPEG-Oxycarbonylimidazole Reagents | $H_3CO-(CH_2CH_2O)_n-\overset{\overset{O}{\|\|}}{C}-NH-(IL\text{-}2)$<br>Carbamate Linkage |
| 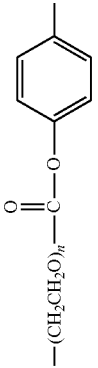<br>mPEG Nitrophenyl Reagents | $H_3CO-(CH_2CH_2O)_n-\overset{\overset{O}{\|\|}}{C}-NH-(IL\text{-}2)$<br>Carbamate Linkage |
| 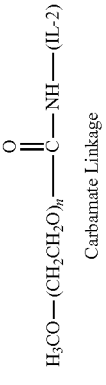<br>mPEG-Trichlorophenyl Carbonate Reagents | $H_3CO-(CH_2CH_2O)_n-\overset{\overset{O}{\|\|}}{C}-NH-(IL\text{-}2)$<br>Carbamate Linkage |
| <br>mPEG-Succinimidyl Reagents | $H_3C-(OCH_2CH_2)_n-O-CH_2-\overset{\overset{O}{\|\|}}{C}-\overset{H}{N}-(IL\text{-}2)$<br>Amide Linkage |
| 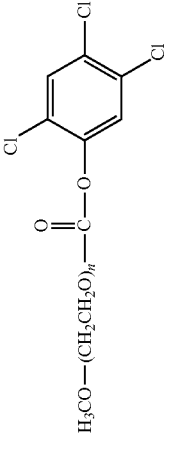<br>Homobifunctional PEG-Succinimidyl Reagents | $(IL\text{-}2)-\overset{H}{N}-\overset{\overset{O}{\|\|}}{C}-CH_2CH_2-(OCH_2CH_2)_n-O-CH_2CH_2-\overset{\overset{O}{\|\|}}{C}-NH-(IL\text{-}2)$<br>Amide Linkages |

TABLE 1-continued

Amine-Selective Polymeric Reagents and the IL-2 Moiety Conjugate Formed Therefrom

| Polymeric Reagent | Corresponding Conjugate |
| --- | --- |
| Biotin-(CH$_2$)$_4$-NH-CH$_2$CH$_2$-(OCH$_2$CH$_2$)$_n$-OCH$_2$C(O)-O-NHS<br><br>Heterobifunctional PEG-Succinimidyl Reagents | Biotin-(CH$_2$)$_4$-NH-CH$_2$CH$_2$-(OCH$_2$CH$_2$)$_n$-OCH$_2$CH$_2$CNH-(IL-2)<br><br>Amide Linkage |
| H$_3$C-(OCH$_2$CH$_2$)$_n$-O-CH$_2$CH$_2$-C(O)-O-NHS<br><br>mPEG-Succinimidyl Reagents | H$_3$C-(OCH$_2$CH$_2$)$_n$-O-CH$_2$CH$_2$-C(O)-NH-(IL-2)<br><br>Amide Linkage |
| H$_3$CO-(CH$_2$CH$_2$O)$_n$-CH$_2$CH$_2$NH-C(O)-CH$_2$-C(O)-O-NHS<br><br>mPEG-Succinimidyl Reagents | H$_3$CO-(OCH$_2$CH$_2$)$_n$-CH$_2$CH$_2$NH-C(O)-CH$_2$-C(O)-NH-(IL-2)<br><br>Amide Linkage |
| H$_3$CO-(CH$_2$CH$_2$O)$_n$-CH$_2$CH$_2$SH-CH$_2$CH$_2$-C(O)-O-NHS<br><br>mPEG Succinimidyl Reagents | H$_3$CO-(CH$_2$CH$_2$O)$_n$-CH$_2$CH$_2$SH-CH$_2$CH$_2$-C(O)-NH-(IL-2)<br><br>Amide Linkage |

TABLE 1-continued

Amine-Selective Polymeric Reagents and the IL-2 Moiety Conjugate Formed Therefrom

| Polymeric Reagent | Corresponding Conjugate |
|---|---|
| mPEG-Succinimidyl Reagents: $H_3C-(OCH_2CH_2)_n-O-CH_2CH_2-C(=O)-O-N(succinimidyl)$ | $H_3C-(OCH_2CH_2)_n-O-CH_2CH_2-C(=O)-NH-(IL-2)$<br>Amide Linkage |
| mPEG-Benzotriazole Carbonate Reagents: $H_3C-(OCH_2CH_2)_n-O-C(=O)-O-benzotriazole$ | $H_3C-(OCH_2CH_2)_n-O-C(=O)-NH-(IL-2)$<br>Carbamate Linkage |
| mPEG-Succinimidyl Reagents: $H_3C-(OCH_2CH_2)_n-NH-C(=O)-O-C_6H_4-C(=O)-O-N(succinimidyl)$ | $H_3C-(OCH_2CH_2)_n-NH-C(=O)-O-C_6H_4-C(=O)-NH-(IL-2)$<br>Carbamate Linkage |
| mPEG-Succinimidyl Reagents: $H_3CO-(CH_2CH_2O)_n-C_6H_4-C(=O)-O-N(succinimidyl)$ | $H_3CO-(CH_2CH_2O)_n-C_6H_4-C(=O)-NH-(IL-2)$<br>Amide Linkage |

TABLE 1-continued

Amine-Selective Polymeric Reagents and the IL-2 Moiety Conjugate Formed Therefrom

| Polymeric Reagent | Corresponding Conjugate |
|---|---|
| mPEG Succinimidyl Reagents | Amide Linkage |
| Branched mPEG2-N-Hydroxysuccinimide Reagents | Amide Linkage |
| Branched mPEG2-Aldehyde Reagents | Secondary Amine Linkage |

TABLE 1-continued

Amine-Selective Polymeric Reagents and the IL-2 Moiety Conjugate Formed Therefrom

| Polymeric Reagent | Corresponding Conjugate |

TABLE 1-continued

Amine-Selective Polymeric Reagents and the IL-2 Moiety Conjugate Formed Therefrom

| Polymeric Reagent | Corresponding Conjugate |
|---|---|
| Homobifunctional PEG-Succinimidyl Propionate Reagents | Amide Linkages |
| mPEG-Succinimidyl Reagents | Amide Linkage |
| Branched mPEG2-N-Hydroxysuccinimide Reagents | Amide Linkage |
| Branched mPEG2-N-Hydroxysuccinimide Reagents | Amide Linkage |

TABLE 1-continued

Amine-Selective Polymeric Reagents and the IL-2 Moiety Conjugate Formed Therefrom

| Polymeric Reagent | Corresponding Conjugate |
|---|---|
| mPEG-Thioester Reagents: $H_3C-(OCH_2CH_2)_n-O-CH_2-CH_2-C(=O)-S-\text{(2-pyridyl)}$ | $H_3C-(OCH_2CH_2)_n-O-CH_2CH_2C(=O)-NH-(IL\text{-}2)$ Amide Linkage (typically to IL-2 moiety having an N-terminal cysteine or histidine) |
| Homobifunctional PEG Propionaldehyde Reagents: $HC(=O)-CH_2CH_2-(OCH_2CH_2)_n-O-CH_2CH_2-CH(=O)$ | $\text{(IL-2)}-NH-CH_2CH_2CH_2-(OCH_2CH_2)_n-O-CH_2CH_2-CH_2-NH-(IL\text{-}2)$ Secondary Amine Linkages |
| mPEG Propionaldehyde Reagents: $H_3C-(OCH_2CH_2)_n-O-CH_2CH_2-CH(=O)$ | $H_3C-(OCH_2CH_2)_n-O-CH_2CH_2-CH_2-NH-(IL\text{-}2)$ Secondary Amine Linkage |
| Homobifunctional PEG Butyraldehyde Reagents: $HC(=O)CH_2CH_2CH_2-(OCH_2CH_2)_n-O-CH_2CH_2CH_2CH(=O)$ | $HN(IL\text{-}2)-CH_2CH_2CH_2CH_2-(OCH_2CH_2)_n-O-CH_2CH_2CH_2-CH_2-NH-(IL\text{-}2)$ Secondary Amine Linkages |
| mPEG Butyraldehyde Reagents: $H_3C-(OCH_2CH_2)_n-O-CH_2CH_2CH_2CH(=O)$ | $H_3C-(OCH_2CH_2)_n-O-C(=O)-NH-(CH_2CH_2O)_4-CH_2CH_2CH_2CH_2-NH-(IL\text{-}2)$ Secondary Amine Linkage |
| Homobifunctional PEG Butryaldehyde Reagents: $O=C(HN-(CH_2CH_2O)_4-CH_2CH_2CH(=O))-(OCH_2CH_2)_n-O-C(=O)-NH-(CH_2CH_2O)_4-CH_2CH_2CH$ | $O=C(HN-(CH_2CH_2O)_4-CH_2CH_2CH_2-NH-(IL\text{-}2))-(OCH_2CH_2)_n-O-C(=O)-NH-(CH_2CH_2O)_4-CH_2CH_2CH_2CH_2-NH-(IL\text{-}2)$ Secondary Amine Linkages |

TABLE 1-continued

Amine-Selective Polymeric Reagents and the IL-2 Moiety Conjugate Formed Therefrom

| Polymeric Reagent | Corresponding Conjugate |
|---|---|
| H₃C—(OCH₂CH₂)ₙ—O—C(=O)—NH—CH₂—CH₂—CH₂—CH₂—CH(C(=O)—NH—(CH₂CH₂O)₄—CH₂CH₂CH₂CH)—O—C(=O)—NH—(OCH₂CH₂)ₙ—CH₃ <br> Branched mPEG2 Butyraldehyde Reagents | H₃C—(OCH₂CH₂)ₙ—O—C(=O)—NH—CH₂—CH₂—CH₂—CH₂—CH₂—(C(=O)—NH—(CH₂CH₂O)₄—CH₂CH₂CH₂CH₂—NH—(IL-2))—O—C(=O)—NH—(OCH₂CH₂)ₙ—CH₃ <br> Secondary Amine Linkage |
| H₃C—(OCH₂CH₂)ₙ—NH—C(=O)—O—CH₂—CH(O—C(=O)—NH—(OCH₂CH₂)ₙ—CH₃)—CH₂—CH₂—C(=O)—NH—(CH₂CH₂O)₄—CH₂CH₂CH₂CH <br> Branched mPEG2 Butyraldehyde Reagents | H₃C—(OCH₂CH₂)ₙ—NH—C(=O)—O—CH₂—CH(O—C(=O)—NH—(OCH₂CH₂)ₙ—CH)—CH₂—C(=O)—NH—(CH₂CH₂O)₄—CH₂CH₂CH₂CH₂—NH—(IL-2) <br> Secondary Amine Linkage |
| H₃C—(OCH₂CH₂)ₙ—O—CH₂—CH(OCH₂CH₃)—OCH₂CH₃ <br> mPEG Acetal Reagents | H₃C—(OCH₂CH₂)ₙ—O—CH₂CH₂—NH—(IL-2) <br> Secondary Amine Linkage (to a secondary carbon) |
| mPEG Piperidone Reagents: <br> H₃C—(OCH₂CH₂)ₙ—O—CH₂CH₂—C(=O)—N(piperidone, C=O at 4-position) | H₃C—(OCH₂CH₂)ₙ—O—CH₂CH₂—C(=O)—N(piperidine-4-NH—(IL-2)) |
| H₃C—(OCH₂CH₂)ₙ—O—(CH₂)₂₋₅—C(=O)—CH₃ <br> mPEG Methylketone Reagents | H₃C—(OCH₂CH₂)ₙ—O—(CH₂)₂₋₅—CH(NH—(IL-2))—CH₃ <br> secondary amine linkage (to a secondary carbon) |
| H₃CO—(CH₂CH₂O)ₙ—S(=O)₂—CH₂—CF₃ <br> mPEG Tresylate Reagents | H₃CO—(CH₂CH₂O)ₙ—CH₂CH₂—NH—(IL-2) <br> Secondary Amine Linkage |

TABLE 1-continued

Amine-Selective Polymeric Reagents and the IL-2 Moiety Conjugate Formed Therefrom

| Polymeric Reagent | Corresponding Conjugate |
|---|---|
| 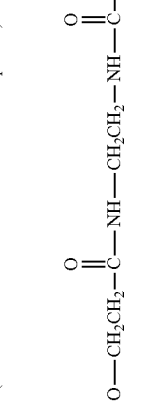<br>$H_3C-(OCH_2CH_2)_n-O-CH_2CH_2-$<br>mPEG Maleimide Reagents<br>(under certain reaction conditions such as pH >8) | 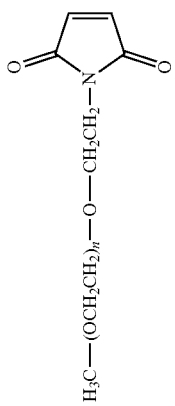<br>$H_3C-(OCH_2CH_2)_n-O-CH_2CH_2-$<br>Secondary Amine Linkage |
| 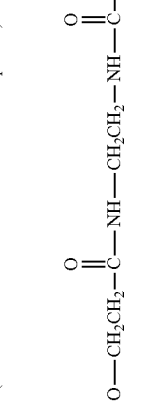<br>$H_3C-(OCH_2CH_2)_n-O-CH_2CH_2-NH-\underset{\underset{O}{\|}}{C}-CH_2CH_2-$<br>mPEG Maleimide Reagents<br>(under certain reaction conditions such as pH >8) | 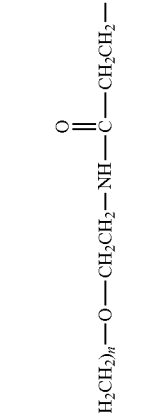<br>$H_3C-(OCH_2CH_2)_n-O-CH_2CH_2-NH-\underset{\underset{O}{\|}}{C}-CH_2CH_2-$<br>Secondary Amine Linkage |
| <br>$H_3C-(OCH_2CH_2)_n-O-CH_2CH_2-\underset{\underset{O}{\|}}{C}-NH-CH_2CH_2-NH-\underset{\underset{O}{\|}}{C}-CH_2CH_2-$<br>mPEG Maleimide Reagents<br>(under certain reaction conditions such as pH >8) | 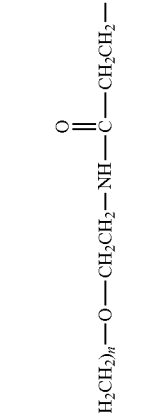<br>$H_3C-(OCH_2CH_2)_n-O-CH_2CH_2-\underset{\underset{O}{\|}}{C}-NH-CH_2CH_2-NH-\underset{\underset{O}{\|}}{C}-CH_2CH_2-$<br>Secondary Amine Linkage |

TABLE 1-continued

Amine-Selective Polymeric Reagents and the IL-2 Moiety Conjugate Formed Therefrom

| Polymeric Reagent | Corresponding Conjugate |
|---|---| mPEG Forked Maleimide Reagents (under certain reaction conditions such as pH >8) — Secondary Amine Linkages branched mPEG2 Maleimide Reagents (under certain reaction conditions such as pH >8) — Secondary Amine Linkage mPEG Epoxide Reagents (under certain reaction conditions such as pH >8) — Secondary Amine Linkage TABLE 1-continued Amine-Selective Polymeric Reagents and the IL-2 Moiety Conjugate Formed Therefrom TABLE 1-continued
Amine-Selective Polymeric Reagents and the IL-2 Moiety Conjugate Formed Therefrom
| Polymeric Reagent | Corresponding Conjugate |
|---|---|
|  Branched mPEG Derivative |  Resealable Linkage |
|  Branched mPEG Derivative |  Releasable Linkage |
|  Branched mPEG Derivative |  Releasable Linkage |

Conjugation of a polymeric reagent to an amino group of an IL-2 moiety can be accomplished by a variety of techniques. In one approach, an IL-2 moiety can be conjugated to a polymeric reagent functionalized with a succinimidyl derivative (or other activated ester group, wherein approaches similar to those described for these alternative activated ester group-containing polymeric reagents can be used). In this approach, the polymer bearing a succinimidyl derivative can be attached to the IL-2 moiety in an aqueous media at a pH of 7 to 9.0, although using different reaction conditions (e.g., a lower pH such as 6 to 7, or different temperatures and/or less than 15° C.) can result in the attachment of the polymer to a different location on the IL-2 moiety. In addition, an amide linkage can be formed by reacting an amine-terminated nonpeptidic, water-soluble polymer with an IL-2 moiety bearing an activating a carboxylic acid group.

Exemplary conjugates are encompassed within the following structure

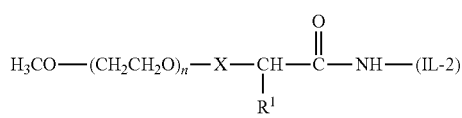

wherein:
(n) is an integer having a value of from 2 to 4000;
X is a spacer moiety;
$R^1$ is an organic radical; and
IL-2 is a residue of an IL-2 moiety.

Exemplary conjugates are encompassed by the following structure:

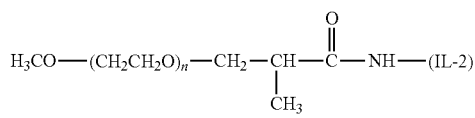

wherein (n) an integer having a value of from 2 to 4000 and IL-2 is a residue of an IL-2 moiety.

Typical of another approach useful for conjugating the IL-2 moiety to a polymeric reagent is use of reductive amination to conjugate a primary amine of an IL-2 moiety with a polymeric reagent functionalized with a ketone, aldehyde or a hydrated form thereof (e.g., ketone hydrate, aldehyde hydrate). In this approach, the primary amine from the IL-2 moiety reacts with the carbonyl group of the aldehyde or ketone (or the corresponding hydroxyl-containing group of a hydrated aldehyde or ketone), thereby forming a Schiff base. The Schiff base, in turn, can then be reductively converted to a stable conjugate through use of a reducing agent such as sodium borohydride. Selective reactions (e.g., at the N-terminus) are possible, particularly with a polymer functionalized with a ketone or an alpha-methyl branched aldehyde and/or under specific reaction conditions (e.g., reduced pH).

Exemplary conjugates of the invention wherein the water-soluble polymer is in a branched form include those wherein the water-soluble polymer is encompassed within the following structure:

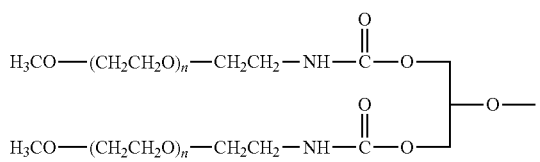

wherein each (n) is independently an integer having a value of from 2 to 4000.

Exemplary conjugates of the invention are encompassed within the following structure:

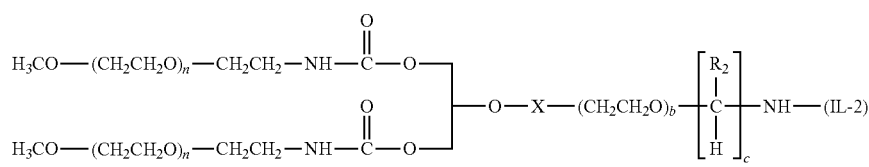

wherein:
  each (n) is independently an integer having a value of from 2 to 4000;
  X is spacer moiety;
  (b) is an integer having a value 2 through 6;
  (c) is an integer having a value 2 through 6;
  $R^2$, in each occurrence, is independently H or lower alkyl; and
  IL-2 is a residue of an IL-2 moiety.

Exemplary conjugates of the invention are encompassed within the following structure:

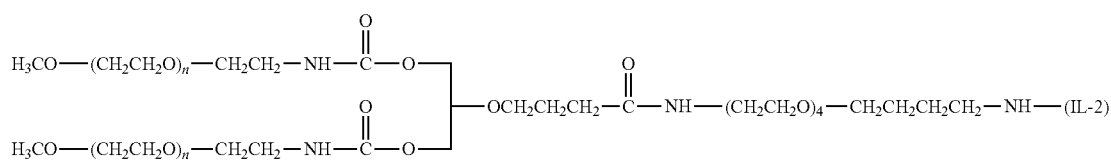

wherein:
  each (n) is independently an integer having a value of from 2 to 4000; and
  IL-2 is a residue of an IL-2 moiety.

Other exemplary conjugates of the invention are encompassed within following structure:

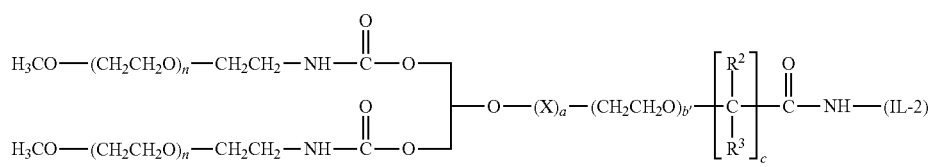

wherein:
  each (n) is independently an integer having a value of from 2 to 4000;
  (a) is either zero or one;
  X, when present, is a spacer moiety comprised of one or more atoms;
  (b') is zero or an integer having a value of one through ten;
  (c) is an integer having a value of one through ten;
  $R^2$, in each occurrence, is independently H or an organic radical;
  $R^3$, in each occurrence, is independently H or an organic radical; and
  IL-2 is a residue of an IL-2 moiety.

Still further exemplary conjugates of the invention are encompassed within the following structure:

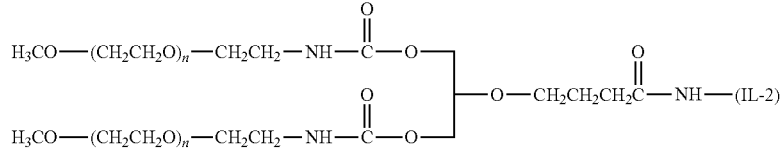

wherein:
each (n) is independently an integer having a value of from 2 to 4000; and
IL-2 is a residue of IL-2 moiety.

Exemplary conjugates that include a releasable linkage include those in which an IL-2 moiety are conjugated to a polymeric reagent encompassed within the following formula:

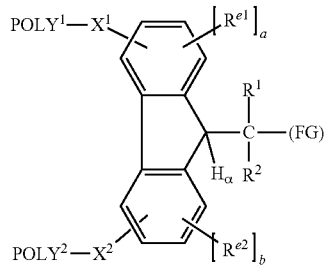

wherein:
POLY$^1$ is a first water-soluble polymer;
POLY$^2$ is a second water-soluble polymer;
X$^1$ is a first spacer moiety;
X$^2$ is a second spacer moiety;
H$_\alpha$ is an ionizable hydrogen atom;
R$^1$ is H or an organic radical;
R$^2$ is H or an organic radical;
(a) is either zero or one;
(b) is either zero or one;
R$^{e1}$, when present, is a first electron altering group;
R$^{e2}$, when present, is a second electron altering group; and
(FG) is a functional group capable of reacting with an amino group of an active agent to form a releasable linkage, such as a carbamate linkage. Within this formula, polymeric reagents having the more defined structure are contemplated:

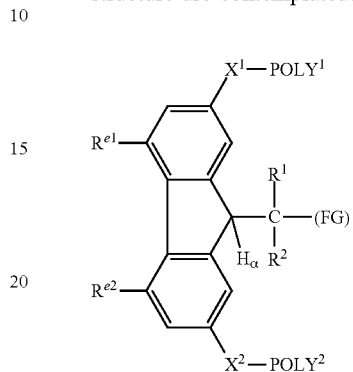

wherein each of POLY$^1$, POLY$^2$, X$^1$, X$^2$, R$^1$, R$^2$, H$_\alpha$ and (FG) is as previously defined, and R$^{e1}$ is a first electron altering group; and R$^{e2}$ is a second electron altering group.

Still further exemplary polymeric reagents fall within the following formulae:

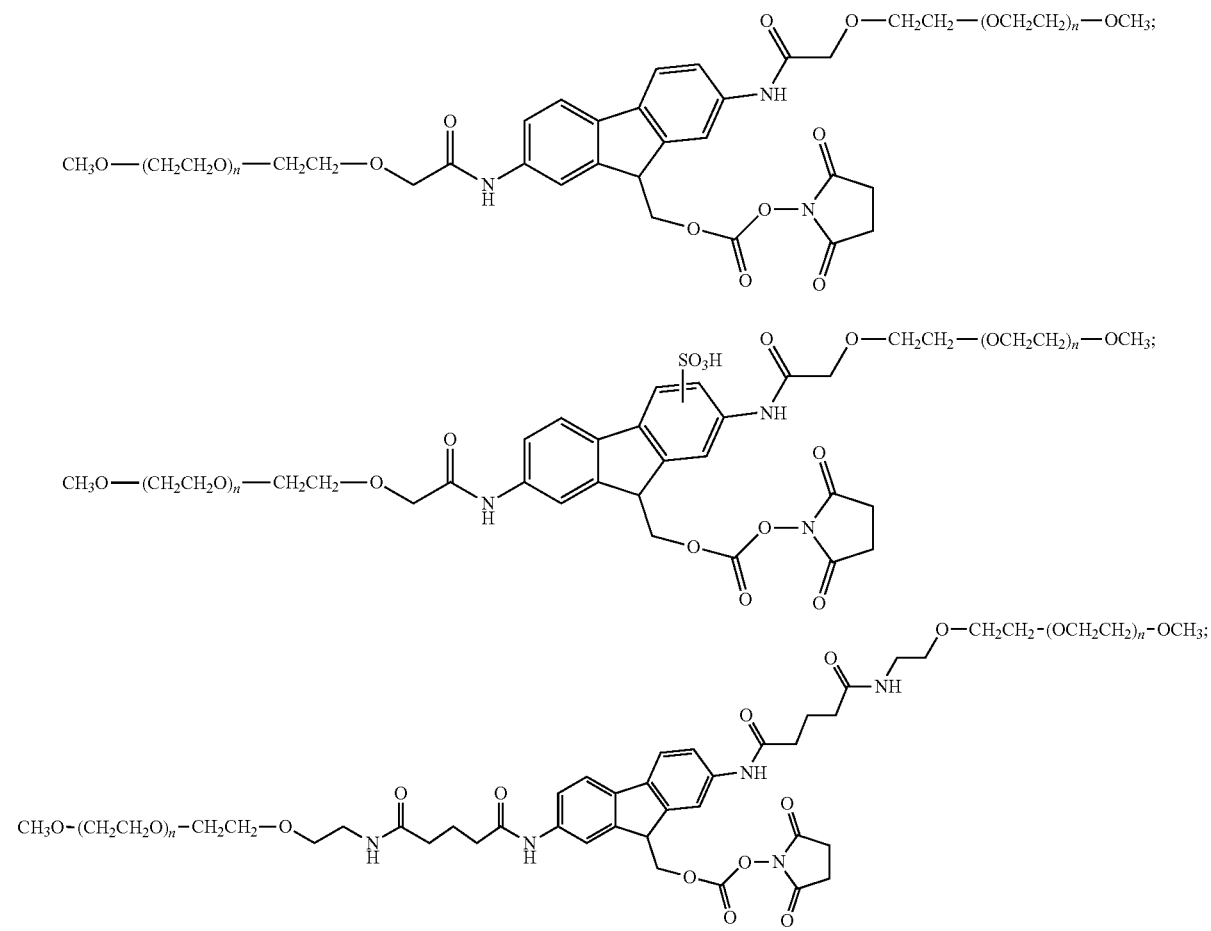

-continued
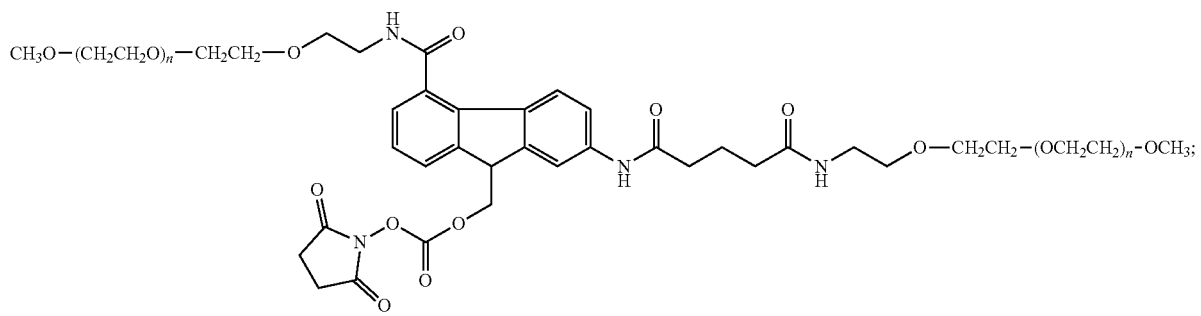
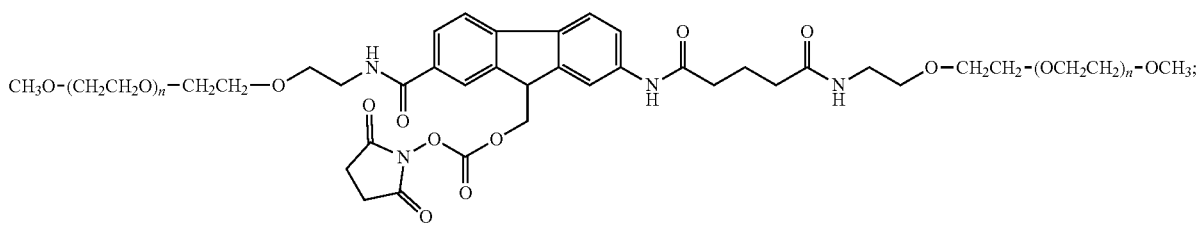
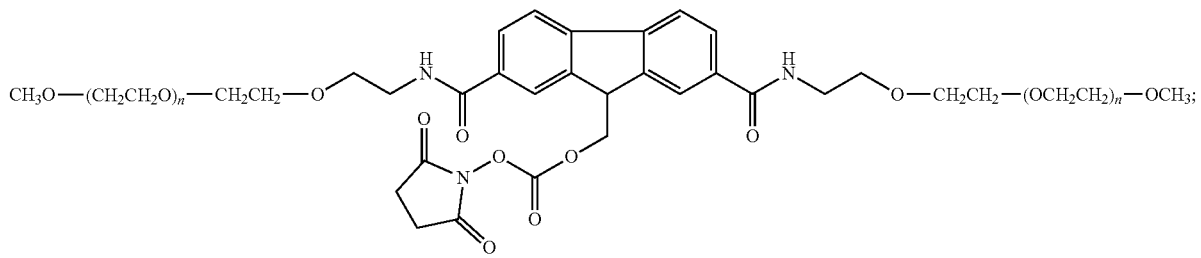
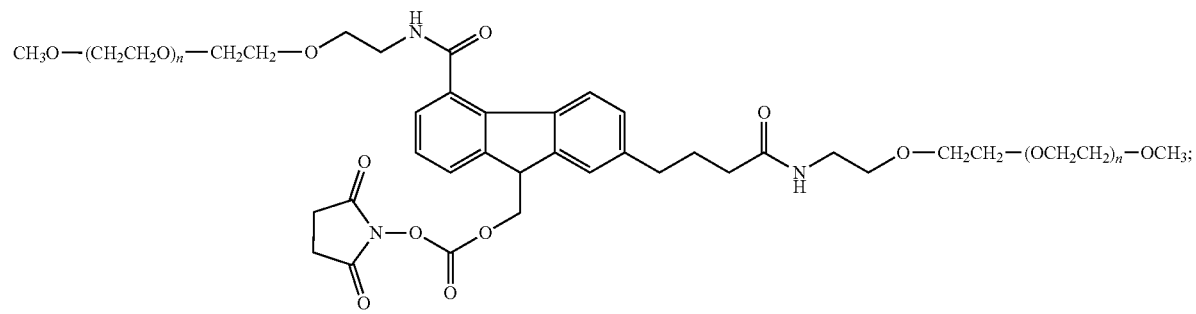
and
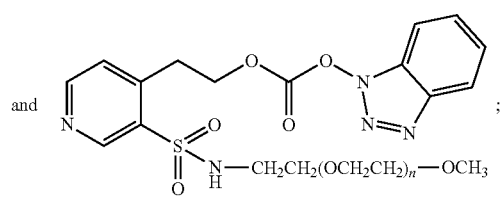

wherein, for each structure and in each instance, (n) is independently an integer from 4 to 1500.

These releasable linkage-providing polymeric reagents can be prepared in accordance with the procedures set forth in U.S. Patent Application Publication No. 2006/0293499.

Exemplary conjugates formed using releasable linkage-providing polymeric reagents include those of the following formulae:

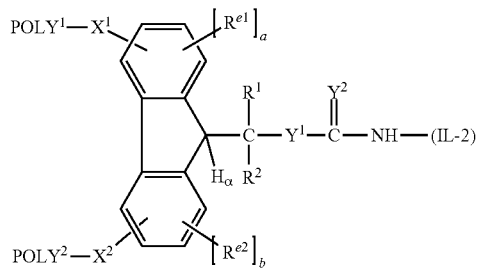

wherein:

POLY$^1$ is a first water-soluble polymer;

POLY$^2$ is a second water-soluble polymer;

X$^1$ is a first spacer moiety;

X$^2$ is a second spacer moiety;

H$_\alpha$ is an ionizable hydrogen atom;

R$^1$ is H or an organic radical;

R$^2$ is H or an organic radical;

(a) is either zero or one;

(b) is either zero or one;

R$^{e1}$, when present, is a first electron altering group;

R$^{e2}$, when present, is a second electron altering group;

Y$^1$ is O or S;

Y$^2$ is O or S; and (IL-2) is a residue of an IL-2 moiety.

Exemplary conjugates have the following structure:

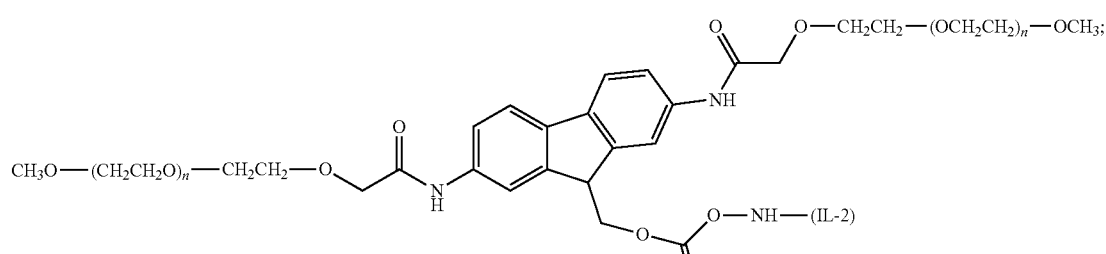

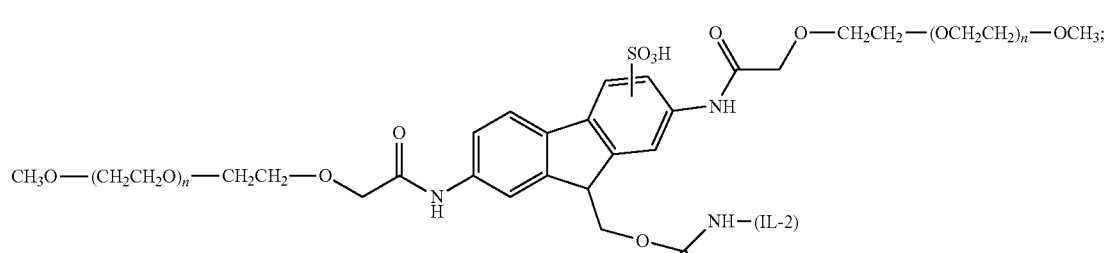

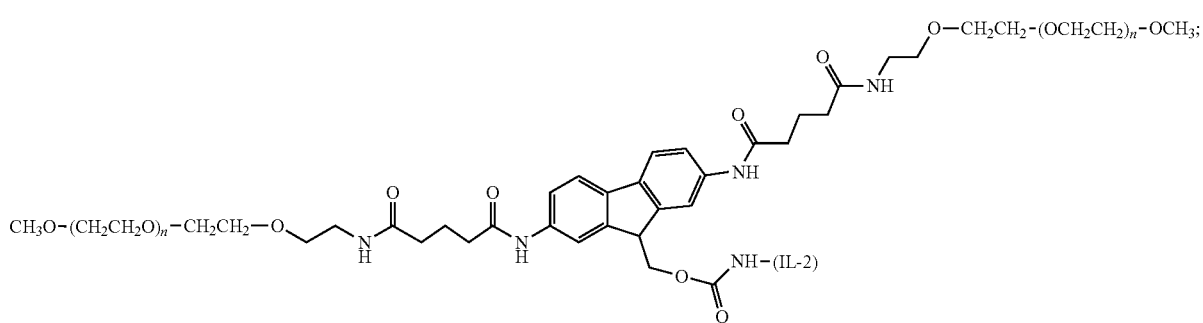

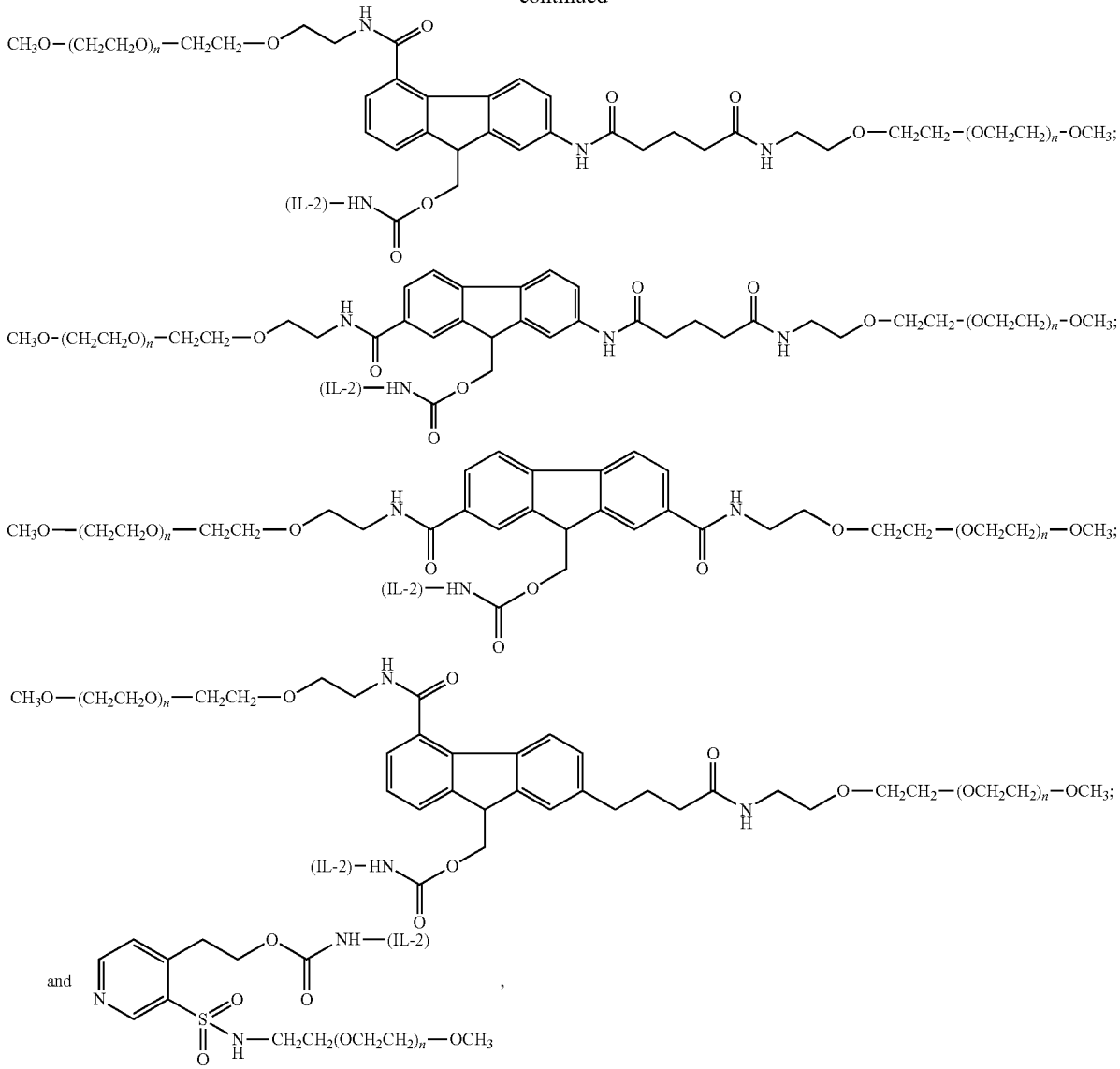

wherein, for each structure and in each instance, (n) is independently an integer from 4 to 1500, and (IL-2) is a residue of an IL-2 moiety.

Carboxyl groups represent another functional group that can serve as a point of attachment on the IL-2 moiety. Structurally, the conjugate will comprise the following:

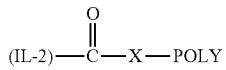

where (IL-2) and the adjacent carbonyl group corresponds to the carboxyl-containing IL-2 moiety, X is a linkage, preferably a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing IL-2 moiety. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Water-soluble derivatives containing a hydrazide moiety are also useful for conjugation at a carbonyl and carboxylic acid. To the extent that the IL-2 moiety does not contain a carbonyl moiety or a carboxylic acid, one can be added using techniques known to one of ordinary skill in the art. For example, a carbonyl moiety can be introduced by reducing a carboxylic acid (e.g., the C-terminal carboxylic acid) and/or by providing glycosylated or glycated (wherein the added sugars have a carbonyl moiety) versions of the IL-2 moiety. With respect to IL-2 moieties containing a carboxylic acid, a PEG-hydrazine reagent can, in the presence of a coupling agent (e.g., DCC), covalently attach to the IL-2 moiety [e.g., mPEG-OCH$_2$C(O)NHNH$_2$+HOC(O)-(IL-2) results in mPEG-OCH$_2$C(O)NHNHC(O)-IL-2]. Specific examples of water-soluble derivatives containing a hydrazide moiety, along with the corresponding conjugates, are provided in Table 2, below. In addition, any water-soluble derivative containing an activated ester (e.g., a succinimidyl group) can be converted to contain a hydrazide moiety by reacting the water-soluble polymer derivative containing the activated ester with hydrazine (NH$_2$—NH$_2$) or tert-butyl carbazate [NH$_2$NHCO$_2$C(CH$_3$)$_3$]. In the table, the variable (n) represents the number of repeating monomeric units and "—C(O)-(IL-2)" represents the residue of the IL-2 moiety following conjugation to the polymeric reagent. Optionally, the hydrazone linkage can be reduced using a suitable reducing agent. While each polymeric portion [e.g., (OCH$_2$CH$_2$)$_n$ or (CH$_2$CH$_2$O)$_n$] presented in Table 2 terminates in a "CH$_3$" group, other groups (such as H and benzyl) can be substituted therefor.

TABLE 2

Carboxyl-Specific Polymeric Reagents and the IL-2 Moiety Conjugate Formed Therefrom

| Polymeric Reagent | Corresponding Conjugate |
|---|---|
| H$_3$CO—(CH$_2$CH$_2$O)$_n$CH$_2$CH$_2$—C(O)—NH—NH$_2$<br>mPEG-Hydrazine Reagents | H$_3$CO—(CH$_2$CH$_2$O)$_n$CH$_2$CH$_2$—C(O)—NH—NH—C(O)—(IL-2)<br>Hydrazone Linkage |
| H$_3$CO—(CH$_2$CH$_2$O)$_n$CH$_2$CH$_2$—O—CH$_2$—C(O)—NH—NH$_2$<br>mPEG-Hydrazine Reagents | H$_3$CO—(CH$_2$CH$_2$O)$_n$CH$_2$CH$_2$—O—CH$_2$—C(O)—NH—NH—C(O)—(IL-2)<br>Hydrazone Linkage |
| H$_3$CO—(CH$_2$CH$_2$O)$_n$CH$_2$CH$_2$—NH—C(O)—NH—NH$_2$<br>mPEG-Hydrazine Reagents | H$_3$CO—(CH$_2$CH$_2$O)$_n$CH$_2$CH$_2$—NH—C(O)—NH—NH—C(O)—(IL-2)<br>Hydrazone Linkage |
| H$_3$CO—(CH$_2$CH$_2$O)$_n$CH$_2$CH$_2$—NH—NH—C(O)—NH—NH$_2$<br>mPEG-Hydrazine Reagents | H$_3$CO—(CH$_2$CH$_2$O)$_n$CH$_2$CH$_2$—N(H)—NH—C(O)—NH—NH—C(O)—(IL-2)<br>Hydrazone Linkage |
| H$_3$CO—(CH$_2$CH$_2$O)$_n$CH$_2$CH$_2$—NH—C(S)—NH—NH$_2$<br>mPEG-Hydrazine Reagents | H$_3$CO—(CH$_2$CH$_2$O)$_n$CH$_2$CH$_2$—NH—C(S)—NH—NH—C(O)—(IL-2)<br>Hydrazone Linkage |
| H$_3$CO—(CH$_2$CH$_2$O)$_n$CH$_2$CH$_2$—NH—NH—C(S)—NH—NH$_2$<br>mPEG-Hydrazine Reagents | H$_3$CO—(CH$_2$CH$_2$O)$_n$CH$_2$CH$_2$—N(H)—NH—C(S)—NH—NH—C(O)—(IL-2)<br>Hydrazone Linkage |
| H$_3$CO-(CH$_2$CH$_2$O)$_n$CH$_2$CH$_2$-NH-C(O)-NH-NH-C(O)-NH-NH$_2$<br>mPEG-Hydrazine Reagents | H$_3$CO—(CH$_2$CH$_2$O)$_n$CH$_2$CH$_2$—NH-C(O)-NH-NH-C(O)-NH-NH-C(O)-(IL-2)<br>Hydrazone Linkage |
| H$_3$CO—(CH$_2$CH$_2$O)$_n$CH$_2$CH$_2$—O—C(O)—NH—NH$_2$<br>mPEG-Hydrazine Reagents | H$_3$CO—(CH$_2$CH$_2$O)$_n$CH$_2$CH$_2$—O—C(O)—NH—NH—C(O)—(IL-2)<br>Hydrazone Linkage |
| H$_3$CO—(CH$_2$CH$_2$O)$_n$CH$_2$—C(O)—NH—NH$_2$<br>mPEG-Hydrazine Reagents | H$_3$CO—(CH$_2$CH$_2$O)$_n$CH$_2$—C(O)—NH—NH—C(O)—(IL-2)<br>C(O)NHNHC(O) Linkage |

Thiol groups contained within the IL-2 moiety can serve as effective sites of attachment for the water-soluble polymer. In particular, cysteine residues provide thiol groups when the IL-2 moiety is a protein. The thiol groups in such cysteine residues can then be reacted with an activated PEG that is specific for reaction with thiol groups, e.g., an N-maleimidyl polymer or other derivative as described in U.S. Pat. No. 5,739,208 and in WO 01/62827. In addition, a protected thiol may be incorporated into an oligosaccharide side chain of an activated glycoprotein, followed by deprotection with a thiol-reactive water-soluble polymer.

Specific examples of reagents, along with the corresponding conjugate, are provided in Table 3, below. In the table, the variable (n) represents the number of repeating monomeric units and "—S-(IL-2)" represents the IL-2 moiety residue following conjugation to the water-soluble polymer. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

With respect to SEQ ID NOs: 1 and 2 corresponding to exemplary IL-2 moieties, it can be seen that there is a cysteine residue at position 125. Thus, an exemplary thiol attachment sites is the cysteine located at position 125. Although it is preferred not to disrupt any disulfide bonds, associated with a given IL-2 moiety, it may be possible to attach a polymer within the side chain of one or more of these cysteine residues and retain a degree of activity. In addition, it is possible to add a cysteine residue to the IL-2 moiety using conventional synthetic techniques. See, for example, the procedure described in WO 90/12874 for adding cysteine residues, wherein such procedure can be adapted for an IL-2 moiety. In addition, conventional genetic engineering processes can also be used to introduce a cysteine residue into the IL-2 moiety. In some embodiments, however, it is preferred not to introduce an additional cysteine residue and/or thiol group.

TABLE 3

Thiol-Selective Polymeric Reagents and the IL-2 Moiety Conjugate Formed Therefrom

| Polymeric Reagent | Corresponding Conjugate |
|---|---|
| 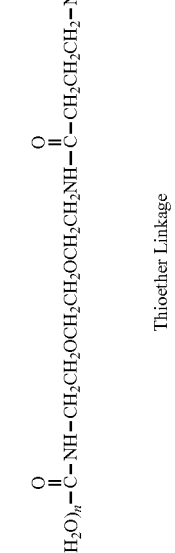 H$_3$C—(OCH$_2$CH$_2$)$_n$—O—CH$_2$CH$_2$— mPEG Maleimide Reagent | 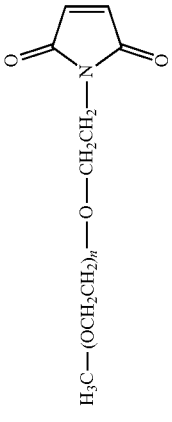 H$_3$C—(OCH$_2$CH$_2$)$_n$—O—CH$_2$CH$_2$— Thioether Linkage |
|  H$_3$CO—(OCH$_2$CH$_2$)$_n$—CH$_2$CH$_2$— mPEG Maleimide Reagent | 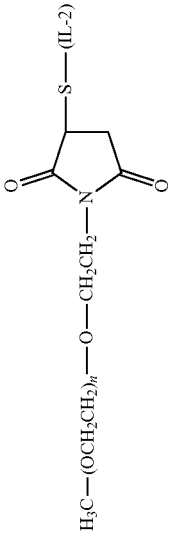 H$_3$CO—(CH$_2$CH$_2$O)$_n$—CH$_2$CH$_2$— Thioether Linkage |
| 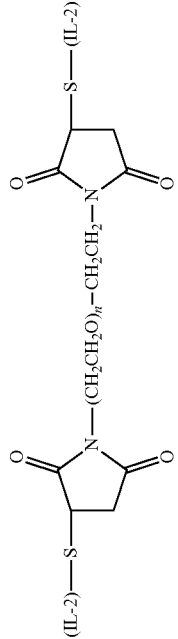 H$_3$CO—(CH$_2$CH$_2$O)$_n$—C(=O)—NH—CH$_2$CH$_2$OCH$_2$CH$_2$OCH$_2$CH$_2$NH—C(=O)—CH$_2$CH$_2$— mPEG Maleimide Reagent | 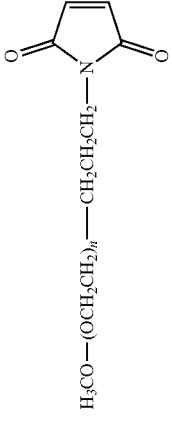 H$_3$CO—(CH$_2$CH$_2$O)$_n$—C(=O)—NH—CH$_2$CH$_2$OCH$_2$CH$_2$OCH$_2$CH$_2$NH—C(=O)—CH$_2$CH$_2$— Thioether Linkage |
| 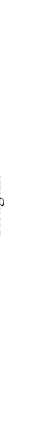 —N—(CH$_2$CH$_2$O)$_n$—CH$_2$CH$_2$— Homobifunctional mPEG Maleimide Reagent | 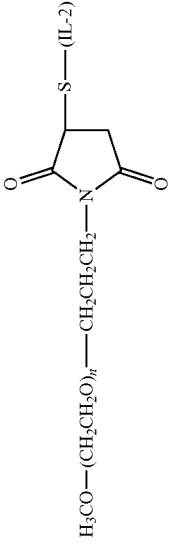 —N—(CH$_2$CH$_2$O)$_n$—CH$_2$CH$_2$— Thioether Linkages |

TABLE 3-continued
Thiol-Selective Polymeric Reagents and the IL-2 Moiety Conjugate Formed Therefrom
| Polymeric Reagent | Corresponding Conjugate |
|---|---|
| 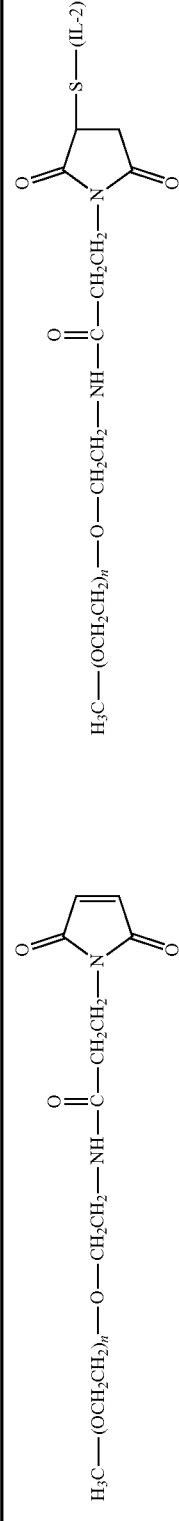 mPEG Maleimide Reagent | 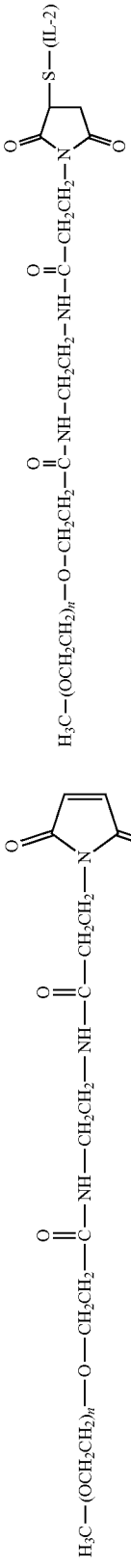 Thioether Linkage |
| 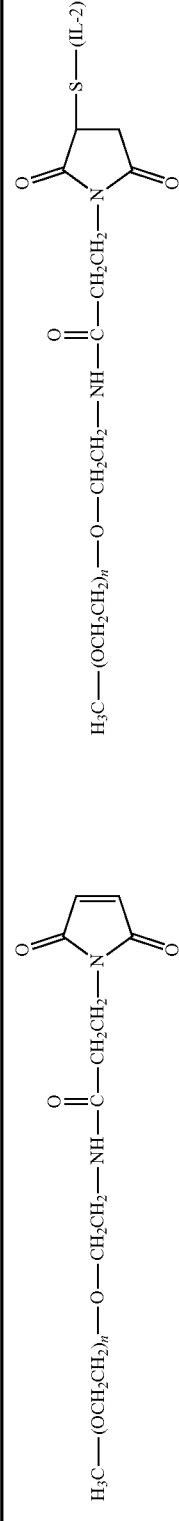 mPEG Maleimide Reagent | 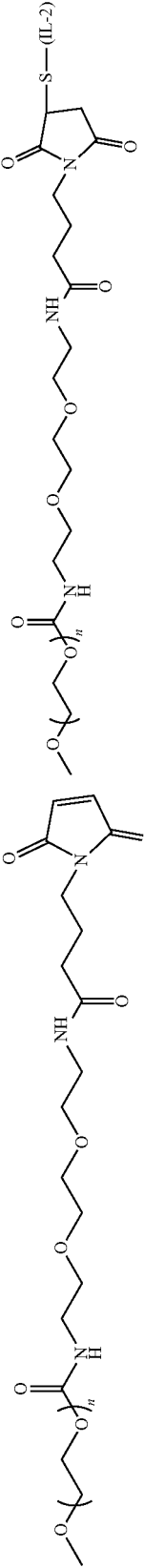 Thioether Linkage |
| 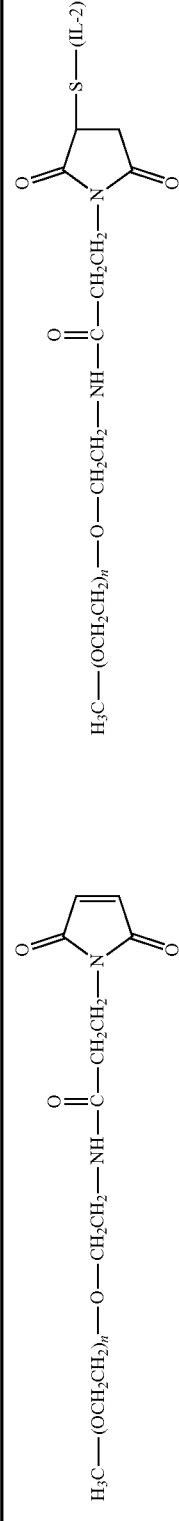 mPEG Maleimide Reagent | 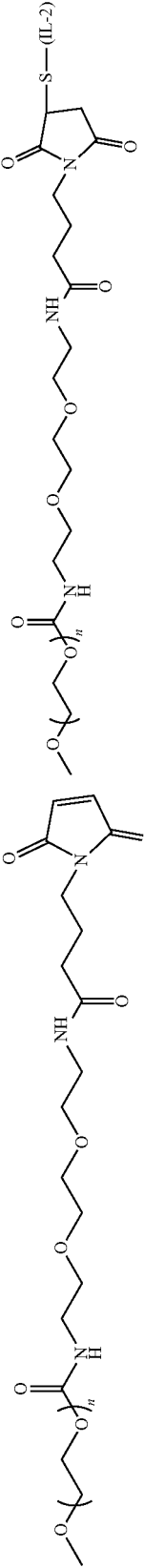 Thioether Linkage |

TABLE 3-continued

Thiol-Selective Polymeric Reagents and the IL-2 Moiety Conjugate Formed Therefrom

| Polymeric Reagent | Corresponding Conjugate |
| --- | --- |
| mPEG Forked Maleimide Reagents | Thioether Linkage |
| branched mPEG2 Maleimide Reagent | Thioether Linkage |

TABLE 3-continued

Thiol-Selective Polymeric Reagents and the IL-2 Moiety Conjugate Formed Therefrom TABLE 3-continued Thiol-Selective Polymeric Reagents and the IL-2 Moiety Conjugate Formed Therefrom

| Polymeric Reagent | Corresponding Conjugate |
|---|---|
| $H_3C-(OCH_2CH_2)_n-O-CH_2CH_2-S(=O)_2-CH=CH_2$<br>mPEG Vinyl Sulfone Reagent | $H_3C-(OCH_2CH_2)_n-O-CH_2CH_2-S(=O)_2-CH_2-CH_2-S-$(IL-2)<br>Thioether Linkage |
| $H_3C-(OCH_2CH_2)_n-O-CH_2CH_2-C(=O)-NH-CH_2-CH_2-SH$<br>mPEG Thiol Reagent | $H_3C-(OCH_2CH_2)_n-O-CH_2CH_2-C(=O)-NH-CH_2-CH_2-S-S-$(IL-2)<br>Disulfide Linkage |
| $HS-CH_2CH_2-NH-C(=O)-CH_2CH_2-(OCH_2CH_2)_n-C(=O)-NH-CH_2-CH_2-SH$<br>Homobifunctional PEG Thiol Reagent | (IL-2)$-S-S-CH_2CH_2-NH-C(=O)-CH_2CH_2-(OCH_2CH_2)_n-C(=O)-NH-CH_2-CH_2-S-S-$(IL-2)<br>Disulfide Linkages |
| $H_3CO-(OCH_2CH_2)_n-CH_2CH_2CH_2CH_2-S-S-$<pyridine><br>mPEG Disulfide Reagent | $H_3CO-(OCH_2CH_2)_n-CH_2CH_2CH_2CH_2-S-S-$(IL-2)<br>Disulfide Linkage |
| <pyridine>$-S-S-CH_2CH_2-(OCH_2CH_2)_n-CH_2CH_2CH_2CH_2-S-S-$<pyridine><br>Homobifunctional Disulfide Reagent | (IL-1)$-S-S-CH_2CH_2-(OCH_2CH_2)_n-CH_2CH_2CH_2CH_2-S-S-$(IL-2)<br>Disulfide Linkages |

With respect to conjugates formed from water-soluble polymers bearing one or more maleimide functional groups (regardless of whether the maleimide reacts with an amine or thiol group on the IL-2 moiety), the corresponding maleamic acid form(s) of the water-soluble polymer can also react with the IL-2 moiety. Under certain conditions (e.g., a pH of about 7-9 and in the presence of water), the maleimide ring will "open" to form the corresponding maleamic acid. The maleamic acid, in turn, can react with an amine or thiol group of an IL-2 moiety. Exemplary maleamic acid-based reactions are schematically shown below. POLY represents the water-soluble polymer, and (IL-2) represents the IL-2 moiety.

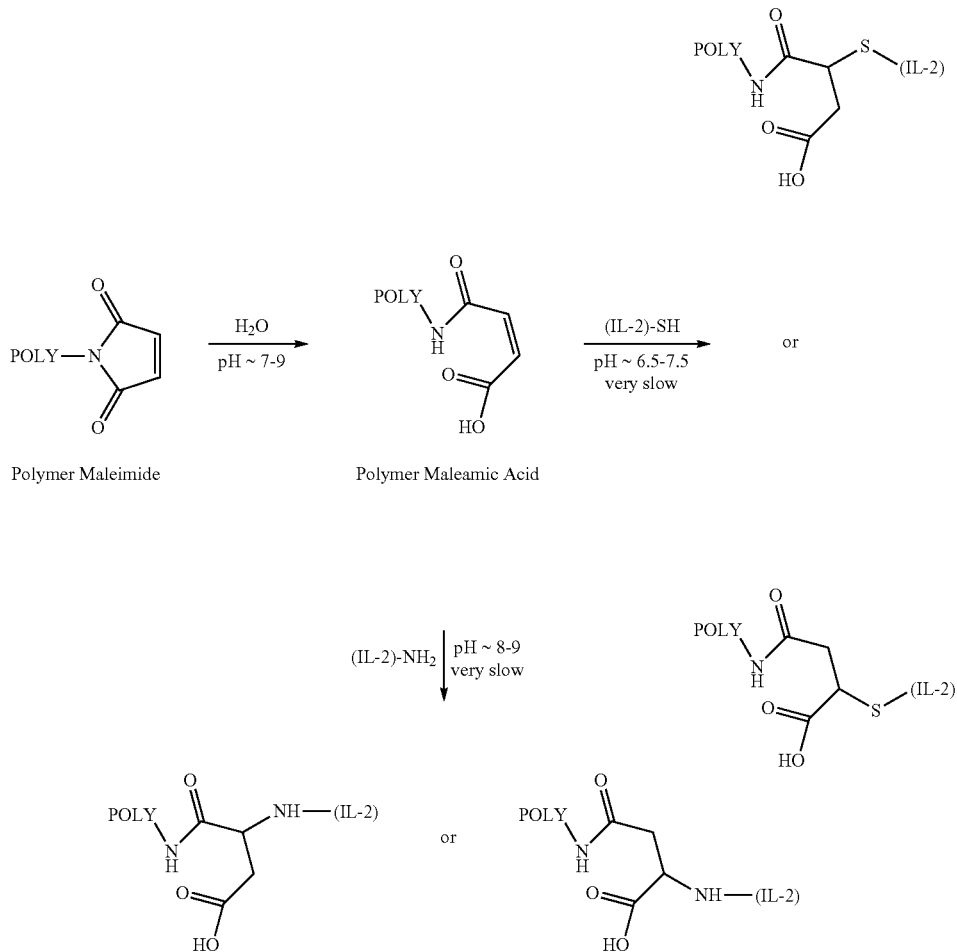

A representative conjugate in accordance with the invention can have the following structure:

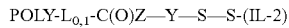

POLY-L$_{0,1}$-C(O)Z—Y—S—S-(IL-2)

wherein POLY is a water-soluble polymer, L is an optional linker, Z is a heteroatom selected from the group consisting of O, NH, and S, and Y is selected from the group consisting of C$_{2-10}$ alkyl, C$_{2-10}$ substituted alkyl, aryl, and substituted aryl, and (IL-2) is an IL-2 moiety. Polymeric reagents that can be reacted with an IL-2 moiety and result in this type of conjugate are described in U.S. Patent Application Publication No. 2005/0014903.

As previously indicated, exemplary conjugates of the invention wherein the water-soluble polymer is in a branched form, will have the branched form of the water-soluble polymer comprise the following structure:

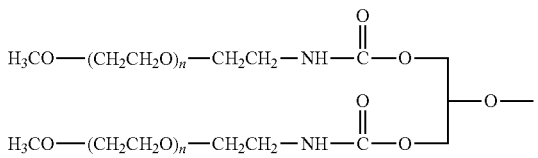

wherein each (n) is independently an integer having a value of from 2 to 4000.

Exemplary conjugates having a water-soluble polymer in branched form are prepared using the following reagent:

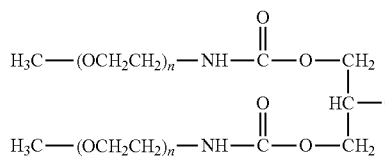
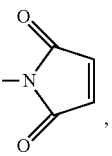

thereby forming a conjugate having the following structure:

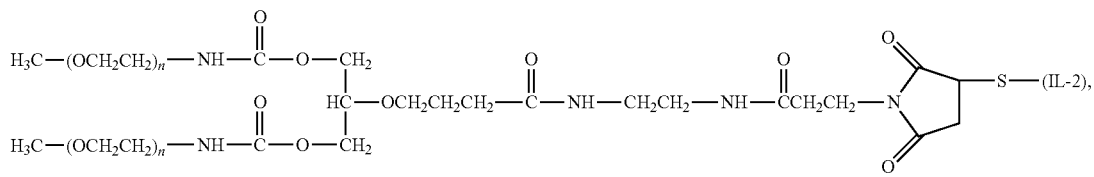

wherein:
(for each structure) each (n) is independently an integer having a value of from 2 to 4000; and
IL-2 is a residue of IL-2 moiety.

An additional exemplary conjugate can be formed using a reagent:

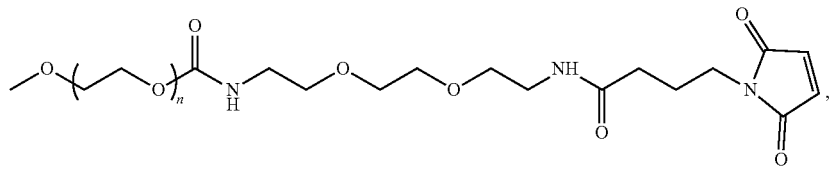

thereby forming a conjugate having the following structure:

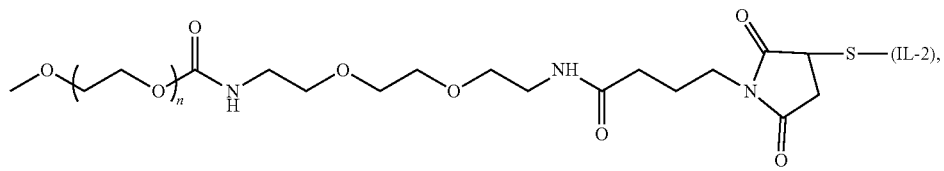

wherein:
(for each structure) (n) is independently an integer having a value of from 2 to 4000; and
IL-2 is a residue of IL-2 moiety.

Conjugates can be formed using thiol-selective polymeric reagents in a number of ways and the invention is not limited in this regard. For example, the IL-2 moiety—optionally in a suitable buffer (including amine-containing buffers, if desired)—is placed in an aqueous media at a pH of about 7-8 and the thiol-selective polymeric reagent is added at a molar excess. The reaction is allowed to proceed for about 0.5 to 2 hours, although reaction times of greater than 2 hours (e.g., 5 hours, 10 hours, 12 hours, and 24 hours) can be useful if PEGylation yields are determined to be relatively low. Exemplary polymeric reagents that can be used in this approach are polymeric reagents bearing a reactive group selected from the group consisting of maleimide, sulfone (e.g., vinyl sulfone), and thiol (e.g., functionalized thiols such as an ortho pyridinyl or "OPSS").

With respect to polymeric reagents, those described here and elsewhere can be purchased from commercial sources or prepared from commercially available starting materials. In addition, methods for preparing the polymeric reagents are described in the literature.

The attachment between the IL-2 moiety and the non-peptidic water-soluble polymer can be direct, wherein no intervening atoms are located between the IL-2 moiety and the polymer, or indirect, wherein one or more atoms are located between the IL-2 moiety and the polymer. With respect to the indirect attachment, a "spacer moiety" serves as a linker between the residue of the IL-2 moiety and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties include those selected from the group consisting of —O—, —S—, —S—S—, —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

Compositions

The conjugates are typically part of a composition. Generally, the composition comprises a plurality of conjugates, preferably although not necessarily, each conjugate is comprised of the same IL-2 moiety (i.e., within the entire composition, only one type of IL-2 moiety is found). In addition, the composition can comprise a plurality of conjugates wherein any given conjugate is comprised of a moiety selected from the group consisting of two or more different IL-2 moieties (i.e., within the entire composition, two or more different IL-2 moieties are found). Optimally, however, substantially all conjugates in the composition (e.g., 85% or more of the plurality of conjugates in the composition) are each comprised of the same IL-2 moiety.

The composition can comprise a single conjugate species (e.g., a monoPEGylated conjugate wherein the single polymer is attached at the same location for substantially all conjugates in the composition) or a mixture of conjugate species (e.g., a mixture of monoPEGylated conjugates where attachment of the polymer occurs at different sites and/or a mixture monPEGylated, diPEGylated and triPEGylated conjugates). The compositions can also comprise other conjugates having four, five, six, seven, eight or more polymers attached to any given moiety having IL-2 activity. In addition, the invention includes instances wherein the composition comprises a plurality of conjugates, each conjugate comprising one water-soluble polymer covalently attached to one IL-2 moiety, as well as compositions comprising two, three, four, five, six, seven, eight, or more water-soluble polymers covalently attached to one IL-2 moiety.

With respect to the conjugates in the composition, the composition will satisfy one or more of the following characteristics at least about 85% of the conjugates in the composition will have from one to four polymers attached to the IL-2 moiety; at least about 85% of the conjugates in the composition will have from one to three polymers attached to the IL-2 moiety; at least about 85% of the conjugates in the composition will have from one to two polymers attached to the IL-2 moiety; at least about 85% of the conjugates in the composition will have one polymer attached to the IL-2 moiety; at least about 95% of the conjugates in the composition will have from one to five polymers attached to the IL-2 moiety; at least about 95% of the conjugates in the composition will have from one to four polymers attached to the IL-2 moiety; at least about 95% of the conjugates in the composition will have from one to three polymers attached to the IL-2 moiety; at least about 95% of the conjugates in the composition will have from one to two polymers attached to the IL-2 moiety; at least about 95% of the conjugates in the composition will have one polymer attached to the IL-2 moiety; at least about 99% of the conjugates in the composition will have from one to five polymers attached to the IL-2 moiety; at least about 99% of the conjugates in the composition will have from one to four polymers attached to the IL-2 moiety; at least about 99% of the conjugates in the composition will have from one to three polymers attached to the IL-2 moiety; at least about 99% of the conjugates in the composition will have from one to two polymers attached to the IL-2 moiety; and at least about 99% of the conjugates in the composition will have one polymer attached to the IL-2 moiety. It is understood that a reference to a range of polymers, e.g., "from x to y polymers," contemplates a number of polymers x to y inclusive (that is, for example, "from one to three polymers" contemplates one polymer, two polymers and three polymers, "from one to two polymers" contemplates one polymer and two polymers, and so forth).

In one or more embodiments, it is preferred that the conjugate-containing composition is free or substantially free of albumin. It is also preferred that the composition is free or substantially free of proteins that do not have IL-2 activity. Thus, it is preferred that the composition is 85%, more preferably 95%, and most preferably 99% free of albumin. Additionally, it is preferred that the composition is 85%, more preferably 95%, and most preferably 99% free of any protein that does not have IL-2 activity. To the extent that albumin is present in the composition, exemplary compositions of the invention are substantially free of conjugates comprising a poly(ethylene glycol) polymer linking a residue of an IL-2 moiety to albumin.

In the PROLEUKIN® brand of aldesleukin (available from Prometheus Laboratories Inc., San Diego CA), IL-2 is provided in combination with sodium dodecyl sulfate ("SDS"). In contrast, the compositions of the present invention advantageously may not require SDS and are therefore free (or substantially) free of SDS as well as detergents generally (e.g., TWEEN® 20 and TWEEN® 80). Consequently, the compositions and conjugates of the present invention can be prepared without performing a step of adding SDS, TWEEN® 20, and TWEEN® 80. In addition, the compositions and conjugates of the present invention can be prepared without performing the step of adding a detergent or other excipient. Furthermore, the compositions of the present invention are free or substantially free (e.g., less than about 20%, more preferably less than about 15%, still more preferably less than about 10%, yet still more preferably less than about 9%, yet still more preferably less than about 8%, yet still more preferably less than about 7%, yet still more preferably less than about 6%, yet still more preferably less than about 5%, yet still more preferably less than about 4%, yet still more preferably less than about 3%, yet still more preferably less than about 2%, yet still more preferably less than about 1%, yet still more preferably less than about 0.5%, with less than 0.001% being most preferred) of detergents such as SDS, TWEEN® 20, and TWEEN® 80. In addition, the compositions and conjugates of the present invention can be prepared without performing the step of removing (by, for example, ultra-filtration) detergents such as SDS, TWEEN® 20, and TWEEN® 80. Furthermore, the compositions and conjugates of the present invention can be prepared without performing the step of removing (by, for example, ultra-filtration) a detergent.

Control of the desired number of polymers for any given moiety can be achieved by selecting the proper polymeric reagent, the ratio of polymeric reagent to the IL-2 moiety, temperature, pH conditions, and other aspects of the conjugation reaction. In addition, reduction or elimination of the undesired conjugates (e.g., those conjugates having four or more attached polymers) can be achieved through purification means.

For example, the polymer-IL-2 moiety conjugates can be purified to obtain/isolate different conjugated species. Specifically, the product mixture can be purified to obtain an average of anywhere from one, two, three, four, five or more PEGs per IL-2 moiety, typically one, two or three PEGs per IL-2 moiety. The strategy for purification of the final conjugate reaction mixture will depend upon a number of factors, including, for example, the molecular weight of the polymeric reagent employed, the particular IL-2 moiety, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-IL-2 moiety ratios (e.g., 1-mer, 2-mer, 3-mer, and so forth, wherein "1-mer" indicates 1 polymer to IL-2 moiety, "2-mer" indicates two polymers to IL-2 moiety, and so on) on the basis of their differing molecular weights (where the difference corresponds essentially to the average molecular weight of the water-soluble polymer portion). For example, in an exemplary reaction where a 35,000 Dalton protein is randomly conjugated to a polymeric reagent having a molecular weight of about 20,000 Daltons, the resulting reaction mixture may contain unmodified protein (having a molecular weight of about 35,000 Daltons), monoPEGylated protein (having a molecular weight of about 55,000 Daltons), diPEGylated protein (having a molecular weight of about 75,000 Daltons), and so forth.

While this approach can be used to separate PEG and other polymer-IL-2 moiety conjugates having different molecular weights, this approach is generally ineffective for separating positional isoforms having different polymer attachment sites within the IL-2 moiety. For example, gel filtration chromatography can be used to separate from each other mixtures of PEG 1-mers, 2-mers, 3-mers, and so forth, although each of the recovered conjugate compositions may contain PEG(s) attached to different reactive groups (e.g., lysine residues) within the IL-2 moiety.

Gel filtration columns suitable for carrying out this type of separation include SUPERDEX™ and SEPHADEX™ columns available from Amersham Biosciences (Piscataway, NJ). Selection of a particular column will depend upon the desired fractionation range desired. Elution is generally carried out using a suitable buffer, such as phosphate, acetate, or the like. The collected fractions may be analyzed by a number of different methods, for example, (i) absorbance at 280 nm for protein content, (ii) dye-based protein analysis using bovine serum albumin (BSA) as a standard, (iii) iodine testing for PEG content, (iv) sodium dodecyl sulfate polyacrylamide gel electrophoresis (SDS PAGE), followed by staining with barium iodide, and (v) high performance liquid chromatography (HPLC).

Separation of positional isoforms is carried out by reverse phase chromatography using a reverse phase-high performance liquid chromatography (RP-HPLC) using a suitable column (e.g., a C18 column or C3 column, available commercially from companies such as Amersham Biosciences or Vydac) or by ion exchange chromatography using an ion exchange column, e.g., a SEPHAROSE® ion exchange column available from Amersham Biosciences. Either approach can be used to separate polymer-active agent isomers having the same molecular weight (i.e., positional isoforms).

The compositions are preferably substantially free of proteins that do not have IL-2 activity. In addition, the compositions preferably are substantially free of all other noncovalently attached water-soluble polymers. In some circumstances, however, the composition can contain a mixture of polymer-IL-2 moiety conjugates and unconjugated IL-2 moiety.

Optionally, the composition of the invention further comprises a pharmaceutically acceptable excipient. If desired, the pharmaceutically acceptable excipient can be added to a conjugate to form a composition.

Exemplary excipients include, without limitation, those selected from the group consisting of carbohydrates, inorganic salts, antimicrobial agents, antioxidants, surfactants, buffers, acids, bases, amino acids, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, cyclodextrins, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as TWEEN® 20 and TWEEN® 80, and PLURONIC® surfactants such as PLURONIC® F-68 and PLURONIC® F-88 (both of which are available from BASF, Mount Olive, New Jersey); sorbitan esters; lipids, such as phospholipids such as lecithin and other phosphatidylcholines, phosphatidylethanolamines (although preferably not in liposomal form), fatty acids and fatty esters; steroids, such as cholesterol; and EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

One or more amino acids can be present as an excipient in the compositions described herein. Exemplary amino acids in this regard include arginine, lysine and glycine.

The amount of the conjugate (i.e., the conjugate formed between the active agent and the polymeric reagent) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, NJ (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

The compositions of one or more embodiments of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, intratumorally, peritumorally, intraperitonally, subcutaneous, intra-arterial, and so forth.

The invention also provides a method for administering a conjugate as provided herein to a patient suffering from a condition that is responsive to treatment with conjugate. The method comprises administering to a patient, generally via injection, a therapeutically effective amount of the conjugate (preferably provided as part of a pharmaceutical composition). As previously described, the conjugates can be injected (e.g., intramuscularly, subcutaneously and parenterally). Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering the conjugate (preferably provides as part of a pharmaceutical composition) can optionally be conducted so as to localize the conjugate to a specific area. For example, the liquid, gel and solid formulations comprising the conjugate could be surgically implanted in a diseased area (such as in a tumor, near a tumor, in an inflamed area, and near an inflamed area). Conveniently, organs and tissue can also be imaged in order to ensure the desired location is better exposed to the conjugate.

The method of administering may be used to treat any condition that can be remedied or prevented by administration of the conjugate. Those of ordinary skill in the art appreciate which conditions a specific conjugate can effectively treat. For example, the conjugates can be used either alone or in combination with other pharmacotherapy to treat patients suffering from a malady selected from the group consisting of renal cell carcinoma, metastatic melanoma, hepatitis C virus (HCV), human immunodeficiency virus (HIV), acute myeloid leukemia, non-Hodgkin's lymphoma, cutaneous T-cell lymphoma, juvenile rheumatoid arthritis, atopic dermatitis, breast cancer and bladder cancer. Advantageously, the conjugate can be administered to the patient prior to, simultaneously with, or after administration of another active agent.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, symptoms of organophosphate poisoning lessen and/or are eliminated entirely.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis, biochemistry, protein purification and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be taken into account. Unless indicated otherwise, temperature is in degrees C. and pressure is at or near atmospheric pressure at sea level. Each of the following examples is considered to be instructive to one of ordinary skill in the art for carrying out one or more of the embodiments described herein.

An aqueous solution ("stock solution") comprising recombinant IL-2 ("rIL-2") corresponding to the amino acid sequence of SEQ ID NO:3, the mature protein sequence was obtained from Myoderm (Norristown PA) for use in the examples or was prepared in accordance with Example 1. The concentration of the stock solution varied between 1 and 100 mg/mL.

SDS-PAGE Analysis

Samples were analyzed by sodium dodecyl sulfate-polyacrylamide gel electrophoresis (SDS-PAGE) using the Invitrogen NuUPAGE® system and Novex 4-10% Bis-Tris pre-cast gels (Invitrogen, Carlsbad, CA). Samples were prepared, loaded on the gel and electrophoresis performed as described by the manufacturer.

Cation Exchange Chromatography

A SP-HP SEPHAROSE® (GE Healthcare) cation exchange column with a bed volume of approximately 100 ml was prepared using standard methods. The column was connected to a GE Healthcare (Chalfont St. Giles, UK) AKTA Explorer 100 to purify the prepared PEG-rIL-2 conjugates. Details for the purification process are described below.

RP-HPLC Analysis

Reversed-phase chromatography (RP-HPLC) analysis was performed on an Agilent (Santa Clara, CA) 1100 HPLC system. Samples were analyzed using a Silverton (Japan) Intrada WP-RP column (3 um particle size, 2.1×150 mm). The flow rate of the column was 0.5 ml/min. The mobile phases were 0.09% TFA in water (solvent A) and 0.04% TFA in acetonitrile (solvent B).

Example 1

Cloning of the IL-2 Gene and Expression of rIL-2

The human IL-2 cDNA sequence may not be optimally expressed in prokaryotes like *E. coli* due to significant differences in the codon usage of the different organisms. Instead of doing many point mutations to the existing human-derived cDNA sequence to maximize *E. coli* codon usage, a PCR technique was employed to fully synthesize the gene.

The method for synthesizing the gene from overlapping primers was essentially a combination of two methods with minor modifications. A basic discussion of each individual method is provided in Young et al. (2004) *Nucleic Acids Research* 32(7):e59 and Devlin et al. (1988) *Gene* 65:13-22. Briefly, the DNA sequence was divided into forward and reverse oligonucleotides of less than 35 bp with a few exceptions and there were no gaps between the oligonucleotides. Each oligonucleotide overlapped the two adjacent ones on the opposite strand by at least 10 nucleotides at the 3' ends and at least 15 nucleotides at the 5' ends. Dual asymmetric PCR was used to assemble sub-fragments of the gene and these were combined to assemble the entire gene using overlap extension PCR. A T7 endonuclease I selection step was then used to remove mismatched duplexes as described by Young et. al. See Young et al. (2004) *Nucleic Acids Research* 32(7):e59. Restriction enzyme sites were included at the gene termini and the final gene fragment was cloned into a commercially available expression vector for *E. coli*. DNA sequence analysis was used to confirm the sequence obtained as shown in FIG. 1 and SEQ ID NO:5.

Using this approach, the amino acid sequence excludes amino acid position #1 (alanine) as compared to the native mature human sequence and includes a C→S amino acid mutation at amino acid position #125 for the sequence as shown. The first amino acid in this sequence is a methionine for direct bacterial expression (no signal peptide encoded). Upon expression, however, the initial methionine is removed by host methionine amino peptidase.

The gene was cloned into one of the pET (T7) expression vectors. The protein was expressed in the *E. coli* strain BL21(DE3), one of the strains typically used for the T7 expression system. This expression system is available commercially and the methods for expression are available from EMD Biosciences, Merck KGaA, Darmstadt, Germany. The use of this system was done under a research license from the Brookhaven National Laboratory. The vector resulted in the protein being expressed as inclusion bodies in *E. coli*. Typical recipes used for expression can be found in the literature and in Protein Production by Auto-Induction in High-Density Shaking Cultures, by F. William Studier, Biology Department, Brookhaven National Laboratory, Upton, NY 11973 (Dec. 20, 2007).

Following fermentation, the cells were harvested by centrifugation. The cell mass pellet was stored at −80° C. for future homogenization. The frozen cell mass pellet was re-suspended in cell wash buffer (50 mM Tris, 5 mM EDTA, pH 8.0) to a concentration of 10% (W/V) and centrifuged at 13860×g for 30 minutes. The supernatant was discarded. The washed pellet was re-suspended in homogenization buffer (50 mM Tris, 5 mM EDTA, 1 mM PMSF, pH 8.0) and homogenized by a Microfluidizer (M-110P from Microfluidics, Newton, Massachusetts, USA) at 4-15° C. for one pass. The homogenate was diluted 2-fold using cell wash buffer (50 mM Tris, 5 mM EDTA, pH 8.0) and centrifuged at 13860×g for 60 minutes. The supernatant was discarded. The inclusion body pellet was washed in three steps using buffers sequentially of 50 mM Tris, 5 mM EDTA, 2% TRITON™ X-100, pH 8.0; 50 mM Tris, 5 mM EDTA, 1% sodium deoxycholate, pH 8.0; and 50 mM Tris, 5 mM EDTA, 1M NaCl, pH 8.0. After washing, the crude IL-2 inclusion bodies were obtained.

The crude IL-2 inclusion bodies were dissolved into 6M guanidine, 100 mM Tris, pH 8 buffer. EDTA was added to final concentration 2 mM. Dithiothreitol (DTT) was then added to final concentration 50 mM. The mixture was incubated at 50° C. for 30 minutes. After reduction, water was added to the mixture to reduce guanidine concentration to 4.8. After one hour of centrifuging at 13860×g, the resulting gel-like pellet was discarded. The guanidine concentration in the supernatant was further reduced to 3.5M by adding water. The pH was adjusted to 5 with titration of 100% acetic acid. The mixture was incubated at room temperature for 60 minutes and centrifuged at 13860×g for one hour. The resulting pellet was suspended into 3.5M guanidine, 20 mM acetate, 5 mM DTT, pH 5 buffer and centrifuged at 13860×g for one hour. This washing step was repeated one more time.

The clean and reduced IL-2 inclusion bodies were dissolved into 6M guanidine, 100 mM Tris pH 8 buffer. 100 mM $CuCl_2$ stock was added to reach a final $Cu^{2+}$ concentration 0.1 mM. The mixture was incubated at 4° C. overnight.

Another embodiment of the invention is directed to an improved method of allowing proteins to obtain tertiary structure. In this regard, previous methods often relied upon step dilution, which is often harsh to proteins. Thus, in an improved approach to allow for the folding of proteins under more gentle conditions, a method is provided wherein the method comprises the step of placing an expressed protein (e.g., an IL-2 moiety, such as IL-2 prepared in accordance with this example) within a dialysis bag having a pore size less than the size of the expressed protein, and adding (preferably over several hours, e.g., over 6 hours, more preferably over 10 hours, and still more preferably over 15 hours) a protein denaturant-free solution (e.g., water). Exemplary protein denaturant-free solutions are recognized to those of ordinary skill in the art and include, for example, solutions (e.g., buffers and water) that lack (or substantially lack) guanidine, urea, lithium perchlorate, 2-mercaptoethanol, dithiothreitol and detergents. Thus, in accordance with this method, the expressed IL-2 solution was put into dialysis bags (having a molecular weight pore size of 3.5 kiloDaltons). The dialysis bags were put into a reservoir containing 4.8M guanidine, 0.1M Tris, pH 8 buffer. After three hours equilibration, the guanidine concentration in the reservoir was slowly reduced to 2M by pumping water into the reservoir over a period of 15 hours. The entire refolding process was completed at 4° C. The refolded IL-2 was checked with SEC-HPLC.

The refolded IL-2 was centrifuged at 13860×g for 60 minutes to remove precipitates. The supernatant was concentrated with PELLICON® XL TFF membrane system (Millipore Corporation, USA).

The refolded and concentrated IL-2 was loaded on a BPG column (GE Healthcare Bio-Sciences AB, Uppsala Sweden) packed with SEPHACRYL® S-100 HR resin. The running buffer was 2M guanidine, 20 mM Tris pH 8 and flow rate was 25 mL/min. The fractions under the IL-2 monomer peak were pooled. It should be noted that other suitable purification methods may also be employed, such as ion exchange chromatography and hydrophobic interaction chromatography (HIC chromatography).

The IL-2 monomer fraction pool was concentrated to about 1-2 mg/mL using PELLICON® XL TFF membrane system (Millipore Corporation, USA) at 4° C. and 30-40 psi operation pressure. The concentrated IL-2 monomer solution was dialyzed into final formulation buffer (10 mM acetate-Na, 5% trehalose, pH 4.5) to bring down the guanidine concentration lower than 0.1 mM by changing the formulation buffer several times (4-5 times in normal). The formulated IL-2 solution was rendered sterile by passing a 0.22 um filter and stored in −80° C. for further use.

Example 2

PEGylation of rIL-2 with mPEG2-C2-fmoc-20K-NHS

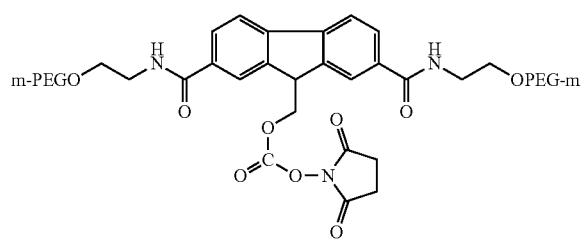

mPEG$_2$-C2-fomc-20K-N-Hydroxysuccinimide Derivative, 20 kDa, ("mPEG2-C2-fmoc-20K-NHS")

mPEG2-C2-fmoc-20K-NHS, stored at −80° C. under argon, was warmed to ambient temperature under nitrogen purging. A stock solution (200 mG/mL) of mPEG2-C2- fmoc-20K-NHS was prepared in 2 mM HCl, and mPEG2-C2-fmoc-20K-NHS was added to the rIL-2 in an amount sufficient to reach a molar ratio of mPEG2-C2-fmoc-20K-NHS to rIL-2 of 100:1. The final concentration of rIL-2 in the mixture was 0.5 mG/mL (0.035 mM). Sodium bicarbonate buffer (1 M, pH 9.0) was added to the mixture to reach a final concentration of 20 mM, and conjugation was allowed to proceed for thirty minutes to provide [mPEG2-C2-fmoc-20K]-[rIL-2] conjugates. After thirty minutes, quenching was achieved by adding 1 M glycine (pH 6.0) to the reaction mixture to achieve a final concentration of 100 mM. The quenched reaction mixture was then diluted with $H_2O$ to provide a conductivity below 0.5 mS/cm (25° C.). The pH was adjusted to 4.0 using glacial acetic acid prior to column chromatography purification.

A typical cation exchange chromatography purification profile of [mPEG2-C2-fmoc-20K]-[rIL-2] is provided in FIG. 2.1. The [mPEG2-C2-fmoc-20K]-[rIL-2] and unreacted PEG are indicated and the lines correspond to absorbance at various wavelengths (e.g., 280 nm and 225 nm). Purity analysis of [mPEG2-C2-fmoc-20K]-[rIL-2] by reverse phase HPLC analysis detected purity of the purified conjugate of 100% at 280 nm. See FIG. 2.2. Purity was not less than 95% as determined by 4-12% NUPAGE® Bis-Tris SDS-PAGE gel with Coomassie Blue Staining (gel not shown) with 20 μg of the purified [mPEG2-C2-fmoc-20K]-[rIL-2]. The apparent large molecular weight of the conjugate, higher than 200 kDa, was believed to be the result of the slow mobility of the conjugate through the gel due to a high degree of PEG hydration and resulting relatively large hydrodynamic radius. Through these tests, it was confirmed that three conjugates were produced: a 4-mer, 3-mer, 2-mer and 1-mer, i.e., a [mPEG2-C2-fmoc-20K]-[rIL-2] in which four "[mPEG2-C2-fmoc-20K]" are attached to a single "[rIL-2]" for a 4-mer, three "[mPEG2-C2-fmoc-20K]" are attached to a single "[rIL-2]" for a 3-mer, two "[mPEG2-C2-fmoc-20K]" are attached to a single [rIL-2] for a 2-mer, and one "[mPEG2-C2-fmoc-20K]" attached to a single [rIL-2] for a 1-mer.

The releasable nature of [mPEG2-C2-fmoc-20K]-[rIL-2] to liberate rIL-2 was shown by detecting the change of species with reverse phase HPLC. Briefly, purified [mPEG2-C2-fmoc-20K]-[rIL-2] was incubated in 100 mM $NaHCO_3$ solution, at pH 9.0, 37° C., for several hours. Periodically, aliquots of the system were obtained and tested to detect the disappearance of [mPEG2-C2-fmoc-20K]-[rIL-2] conjugate and the presence of liberated rIL-2. The appearance of rIL-2 plateaued around ten hours after incubation, with a gradual decrease possibly due to precipitation. Data is provided in FIG. 2.3.

Example 3

PEGylation of rIL-2 with mPEG2-CAC-fmoc-20K-NHS

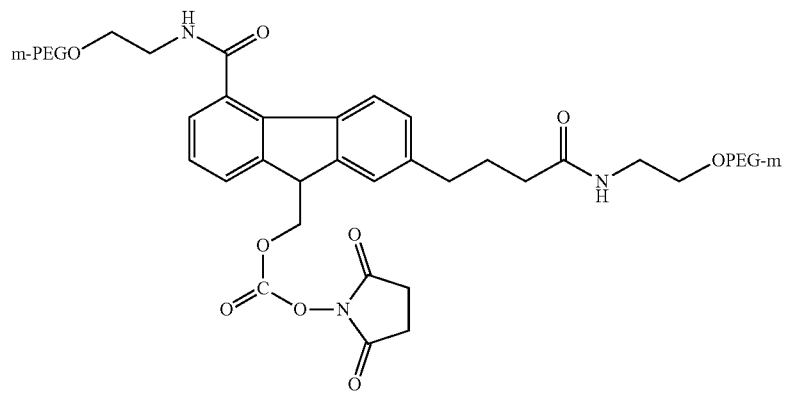

mPEG2-CAC-fmoc-20K-N-Hydroxysuccinimide Derivative, 20 kDa, ("mPEG2-CAC-fmoc-20K-NHS")

mPEG2-CAC-fmoc-20K-NHS, stored at −80° C. under argon, was warmed to ambient temperature under nitrogen purging. A stock solution (200 mG/mL) of mPEG2-CAC-fmoc-20K-NHS was prepared in 2 mM HCl, and mPEG2-CAC-fmoc-20K-NHS was added to the rIL-2 in an amount sufficient to reach a molar ratio of mPEG2-CAC-fmoc-20K-NHS to rIL-2 of 100:1. The final concentration of rIL-2 in the mixture was 0.5 mG/mL (0.035 mM). Sodium bicarbonate buffer (1 M, pH 9.0) was added to the mixture to reach a final concentration of 20 mM, and conjugation was allowed to proceed for thirty minutes to provide [mPEG2-CAC-fmoc-20K]-[rIL-2] conjugates. After thirty minutes, quenching was achieved by adding 1 M glycine (pH 6.0) to the reaction mixture to achieve a final concentration of 100 mM. The quenched reaction mixture was then diluted with H₂O to provide a conductivity below 0.5 mS/cm (25° C.). The pH was adjusted to 4.0 using glacial acetic acid prior to column chromatography purification.

A typical cation exchange chromatography purification profile of [mPEG2-CAC-fmoc-20K]-[rIL-2] is provided in FIG. 3.1. The [mPEG2-CAC-fmoc-20K]-[rIL-2] is indicated and the lines correspond to absorbance at various wavelengths. Purity analysis of [mPEG2-CAC-fmoc-20K]-[rIL-2] by reverse phase HPLC analysis detected purity of the purified conjugate of 98.5% at 280 nm. The peak at 19.6 minutes represents unreacted mPEG2-CAC-fmoc-20K-NHS (which constituted <0.1%). See FIG. 3.2. Purity was not less than 95% as determined by 4-12% NUPAGE® Bis-Tris SDS-PAGE gel with Coomassie Blue Staining (gel not shown) with 20 μg of the purified [mPEG2-CAC-fmoc-20K]-[rIL-2]. The apparent large molecular weight of the conjugate, higher than 200 kDa, was believed to be the result of the slow mobility of the conjugate through the gel due to a high degree of PEG hydration. The molecular weight of purified [mPEG2-CAC-fmoc-20K]-[rIL-2] conjugates was also determined by MALDI-TOF spectrophotometry. As seen in FIG. 3.3, the major peak at 79.6 kDa is within the expected range for the molecular weight of the 3-mer [mPEG2-CAC-fmoc-20K]-[rIL-2] conjugate. The peak at 100.8 kDa is within the expected range for the molecular weight of the 4-mer [mPEG2-CAC-fmoc-20K]-[rIL-2]. The peaks with MW 40 kDa and 58.7 kDa may represent doubly charged 3-mer IL-2 conjugate and 4-mer IL-2 conjugates.

Example 4

PEGylation of rIL-2 with Branched mPEG-N-Hydroxysuccinimidyl Derivative, 20 kDa

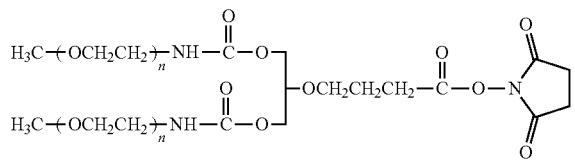

mPEG2-ru-20K-N-Hydroxylsuccinimidyl Derivative, 20 kDa, ("mPEG2-ru-20K-NHS")

mPEG2-ru-20K-NHS, stored at −80° C. under argon, was warmed to ambient temperature under nitrogen purging. A stock solution (200 mG/mL) of mPEG2-ru-20K-NHS was prepared in 2 mM HCl, and mPEG2-ru-20K-NHS was added to the rIL-2 in an amount sufficient to reach a molar ratio of mPEG2-ru-20K-NHS to rIL-2 of 100:1. The final concentration of rIL-2 in the mixture was 0.5 mG/mL (0.035 mM). Sodium bicarbonate buffer (1 M, pH 9.0) was added to the mixture to reach a final concentration of 20 mM, and conjugation was allowed to proceed for thirty to provide [mPEG2-ru-20K]-[rIL-2] conjugates. After thirty minutes, quenching was achieved by adding 1 M glycine (pH 6.0) to the reaction mixture to achieve a final concentration of 100 mM. The quenched reaction mixture was then diluted with H₂O to provide a conductivity below 0.5 mS/cm (25° C.). The pH was adjusted to 4.0 using glacial acetic acid prior to column chromatography purification.

A typical cation exchange chromatography purification profile of [mPEG2-ru-20K]-[rIL-2] is provided in FIG. 4.1. The [mPEG2-ru-20K]-[rIL-2] and unreacted mPEG2-ru-20K-NHS are indicated and the lines correspond to absorbance at various wavelengths (e.g., 280 nm and 225 nm). Purity analysis of [mPEG2-ru-20K]-[rIL-2] by reverse phase HPLC analysis detected purity of the purified conjugate of 100% at 280 nm. See FIG. 4.2. Purity was not less than 95% as determined by 4-12% NUPAGE® Bis-Tris SDS-PAGE gel with Coomassie Blue Staining (gel not shown) with 20 μg of purified [mPEG2-ru-20K]-[rIL-2]. The apparent large molecular weight of the conjugate, higher than 200 kDa, was a result of the slow mobility of the conjugate through the gel due to a high degree of PEG hydration.

Example 5

PEGylation of rIL-2 with Branched mPEG-N-Hydroxysuccinimidyl Derivative, 40 kDa

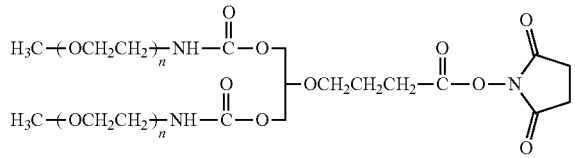

mPEG2-ru-40K-N-Hydroxylsuccinimidyl Derivative, 40 kDa, ("mPEG2-ru-40K-NHS")

mPEG2-ru-40K-NHS, stored at −80° C. under argon, was warmed to ambient temperature under nitrogen purging. A stock solution (200 mG/mL) of mPEG2-ru-40K-NHS was prepared in 2 mM HCl, and mPEG2-ru-40K-NHS was added to the rIL-2 in an amount sufficient to reach a molar ratio of mPEG2-ru-40K-NHS to rIL-2 of 100:1. The final concentration of rIL-2 in the mixture was 0.5 mG/mL (0.035 mM). Sodium bicarbonate buffer (1 M, pH 9.0) was added to the mixture to reach a final concentration of 20 mM, and conjugation was allowed to proceed for thirty minutes to provide [mPEG2-ru-40K]-[rIL-2] conjugates. After thirty minutes, quenching was achieved by adding 1 M glycine (pH 4.0) to the reaction mixture to achieve a final concentration of 100 mM. The quenched reaction mixture was then diluted with H₂O to provide a conductivity below 0.5 mS/cm (25° C.). The pH was adjusted to 4.0 using glacial acetic acid prior to column chromatography purification.

A typical cation exchange chromatography purification profile of [mPEG2-ru-40K]-[rIL-2] is provided in FIG. 5. The [mPEG2-ru-40K]-[rIL-2] and unreacted PEG are indicated and the lines correspond to absorbance at 280 nm. Purity analysis of [mPEG2-ru-40K]-[rIL-2] by reverse phase HPLC analysis detected purity of the purified conjugate of 100% at 280 nm. Purity was not less than 95% as determined by 4-12% NUPAGE® Bis-Tris SDS-PAGE gel with Coomassie Blue Staining (gel not shown) with 20 μg of purified [mPEG2-ru-40K]-[rIL-2]. The apparent large molecular weight of the conjugate (likely a 3-mer version of [mPEG2-ru-40K]-[rIL-2]), higher than 200 kDa, was a result of the slow mobility of the conjugate through the gel due to a high degree of PEG hydration. Un-reacted mPEG2-ru-40K-NHS initially eluted through the column followed by [mPEG2-ru-40K]-[rIL-2] conjugates.

Example 6

PEGylation of rIL-2 with Branched mPEG-N-Hydroxysuccinimidyl Derivative, 4k Da

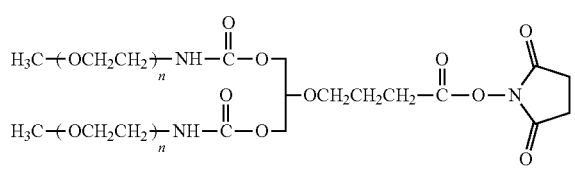

mPEG2-ru-20K-N-Hydroxylsuccinimidyl Derivative, 4 kDa, ("mPEG2-ru-4K-NHS")

mPEG2-ru-4K-NHS, stored at −80° C. under argon, was warmed to ambient temperature under nitrogen purging. A stock solution (200 mG/mL) of mPEG2-ru-4K-NHS was prepared in 2 mM HCl, and mPEG2-ru-4K-NHS was added to the rIL-2 in an amount sufficient to reach a molar ratio of mPEG2-ru-4K-NHS to rIL-2 of 100:1. The final concentration of rIL-2 in the mixture was 0.5 mG/mL (0.035 mM) solubilized with 0.015% SDS. Sodium bicarbonate buffer (1 M, pH 9.0) was added to the mixture to reach a final concentration of 100 mM, and conjugation was allowed to proceed for thirty minutes to provide [mPEG2-ru-4K]-[rIL-2] conjugates. After thirty minutes, quenching was achieved by adding 1 M glycine (pH 4.0) to the reaction mixture to achieve a final concentration of 100 mM. The quenched reaction mixture was then diluted with $H_2O$ to provide a conductivity below 0.5 mS/cm (25° C.). The pH was adjusted to 4.0 using glacial acetic acid prior to column chromatography purification.

Figure 6:
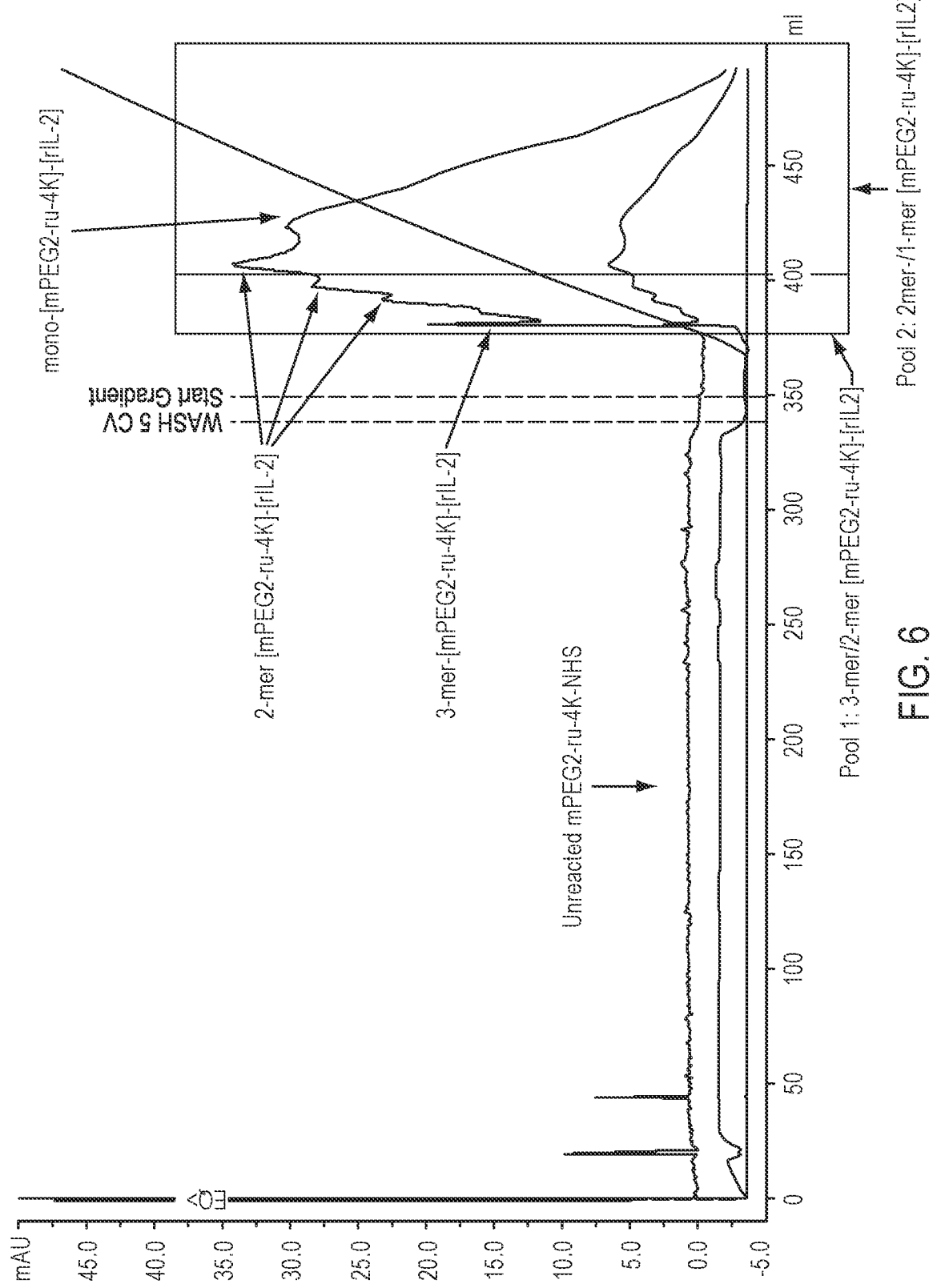
FIG. 6 is a representation of a chromatogram following cation exchange chromatography of [mPEG2-ru-4K]-[rIL-2], as further described in Example 6.

A typical cation exchange chromatography purification profile of [mPEG2-ru-4K]-[rIL-2] is provided in FIG. 6. The eluted [mPEG2-ru-4K]-[rIL-2] conjugates showed a mixture of 3-mer, 2-mer and 1-mer [mPEG2-ru-4K]-[rIL-2] conjugates in the elution fractions. Fractions containing mixture of 3-/2-mer [mPEG2-ru-4K]-[rIL2], as well as fractions containing mixture of 2-/1-mer [mPEG2-ru-4K]-[rIL2] were pooled separately, as shown in FIG. 6.

Example 7

PEGylation of rIL-2 with Linear mPEG-Butyraldehyde Derivative, 30 kDa

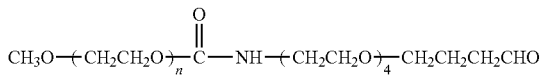

Linear mPEG-Butyraldehyde Derivative, 30 kDa ("mPEG-ButyrALD")

PEGylation reactions are designed such that after addition of all the reaction components and buffers, the final rIL-2 concentration is 2.5 mg/ml. mPEG-ButyrALD, 30 kDa, stored at −20° C. under argon, is warmed to ambient temperature. A quantity of the PEG reagent equal to 10-50 mol equivalents of the rIL-2 to be PEGylated is weighed out and dissolved in 20 mM sodium phosphate buffer (pH 7.5) and 1 mM EDTA to form a 12% reagent solution. The 12% PEG reagent solution is added to the aliquot of stock rIL-2 solution and stirred for 15-30 minutes. A reducing agent, sodium cyanoborohydride ($NaCNBH_3$), is then added at 10-100 molar excess relative to the PEG reagent and the reaction stirred for 5-18 hours at room temperature to ensure coupling via a secondary amine linkage to thereby form a conjugate solution.

The aldehyde group of mPEG-ButyrALD is found to react with the primary amines associated with rIL-2 and covalently bond to them via secondary amine upon reduction by a reducing reagent such as sodium cyanoborohydride. Selectivity for which amine(s) become attached with the polymer can be modulated by adjusting the pH of the conjugation conditions. Relatively low pH conditions (e.g., around a pH of 5.5) will direct conjugation toward the N-terminus. At relatively neutral pH conditions (e.g., around 7.5 and slightly above), covalent attachment becomes more frequent at other locations (i.e., at the amine side chains of lysine residues contained within the protein). Adjusting the pH of the conjugation conditions will allow some degree of control as to which locations conjugation occurs, thereby having a better ability to arrive at the desired positional isomers.

Using this same approach, other conjugates are prepared using mPEG-BuryrALD having other weight average molecular weights.

Example 8

PEGylation of rIL-2 with Branched mPEG-Butyraldehyde Derivative, 40 kDa

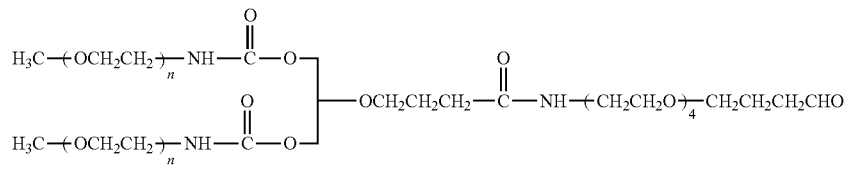

Branched mPEG-Butyraldehyde Derivative, 40 kDa ("mPEG2-ButyrALD")

PEGylation reactions are designed such that after addition of all the reaction components and buffers, the final rIL-2 concentration is 2.5 mg/ml. mPEG2-ButyrALD, 40 kDa, stored at −20° C. under argon, is warmed to ambient temperature. A quantity of the PEG reagent equal to 10-50 mol equivalents of the rIL-2 to be PEGylated is weighed out and dissolved in 20 mM sodium phosphate buffer (pH 7.5) and 1 mM EDTA to form a 12% reagent solution. The 12% PEG reagent solution is added to the aliquot of stock rIL-2 solution and stirred for 15-30 minutes. A reducing agent, sodium cyanoborohydride ($NaCNBH_3$), is then added at 10-100 molar excess relative to the PEG reagent and the reaction stirred for 5-18 hours at room temperature to ensure coupling via a secondary amine linkage to thereby form a conjugate solution.

The aldehyde group of mPEG2-ButyrALD is found to react with the primary amines associated with rIL-2 and covalently bond to them via secondary amine upon reduction by a reducing reagent such as sodium cyanoborohydride.

Using this same approach, other conjugates are prepared using mPEG2-BuryrALD having other weight average molecular weights.

Example 9

PEGylation of rIL-2 with

Linear mPEG-Succinimidyl α-Methylbutanoate Derivative, 30 kDa

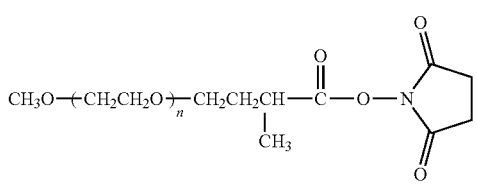

Linear mPEG-Succinimidyl α-Methylbutanoate Derivative, 30 kDa ("mPEG-SMB")

PEGylation reactions are designed such that after addition of all the reaction components and buffers, the final rIL-2 concentration is 2.5 mg/ml. mPEG-SMB, 30 kDa, stored at −20° C. under argon, is warmed to ambient temperature. A quantity of the PEG reagent equal to 10-50 mol equivalents of the rIL-2 to be PEGylated is weighed out and dissolved in 20 mM sodium phosphate buffer (pH 7.5) and 1 mM EDTA to form a 12% reagent solution. The 12% PEG reagent solution is added to the aliquot of stock rIL-2 solution and stirred for 5-18 hours at room temperature thereby resulting in a conjugate solution. The conjugate solution is quenched with a lysine solution (pH 7.5) such that the final lysine molar concentration is 10-100 times the PEG reagent molar concentration.

The mPEG-SMB derivative is found to provide a sterically hindered active NHS ester, which selectively reacts with lysine and terminal amines.

Using this same approach, other conjugates are prepared using mPEG-SMB having other weight average molecular weights.

Example 10

PEGylation of rIL-2 with mPEG-PIP, 20 kDa

The basic structure of the polymeric reagent is provided below:

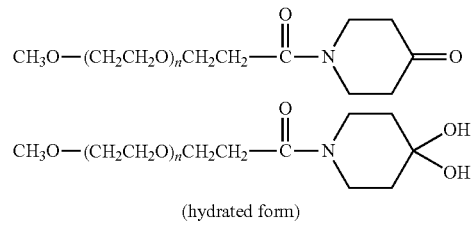

(hydrated form)

PEGylation reactions are designed such that after addition of all the reaction components and buffers, the final rIL-2 concentration is 2.5 mg/ml. mPEG-PIP, 20 kDa, stored at −20° C. under argon, is warmed to ambient temperature. A quantity of the PEG reagent equal to 10-50 mol equivalents of the rIL-2 to be PEGylated is weighed out and dissolved in 20 mM sodium phosphate buffer (pH 7.5) and 1 mM EDTA to form a 12% reagent solution. The 12% PEG reagent solution is added to the aliquot of stock rIL-2 solution and stirred for 15-30 minutes. A reducing agent, sodium cyanoborohydride ($NaCNBH_3$), is then added at 10-100 molar excess relative to the PEG reagent and the reaction stirred for 5-18 hours at room temperature to ensure coupling via a secondary amine linkage (to a secondary carbon) to thereby form a conjugate solution. The conjugate solution is quenched with a lysine solution (pH 7.5) such that the final lysine molar concentration is 10-100 times the PEG reagent molar concentration.

The ketone group of mPEG-PIP is found to react with the primary amines associated with rIL-2 and covalently bond to them via a secondary amine upon reduction by a reducing reagent such as sodium cyanoborohydride.

Using this same approach, other conjugates are prepared using mPEG-PIP having other weight average molecular weights.

Example 11

Activity of Exemplary (rIL-2)-PEG Conjugates

The activity of aldesleukin (control), [mPEG2-C2-fmoc-20K]-[rIL-2] from Example 2, [mPEG2-CAC-fmoc-20K]-[rIL-2] from Example 3, and [mPEG2-ru-20K]-[rIL-2] from Example 4 were evaluated in a cell proliferation assay using CTLL-2 cells.

CTLL-2 cells (mouse cytotoxic T lymphocyte cell line) were maintained in complete RPMI 1640 medium supplemented with 2 mM L-glutamine, 1 mM sodium pyruvate, 10% fetal bovine serum, and 10% IL-2 culture supplement (T-STIM™ with ConA (concanavalin-A)) at 37° C. under a 5% $CO_2$ atmosphere. The cells were cultured in suspension until they reached a cell density of $2-3 \times 10^5$ cells/mL before splitting.

For the activity assay, 3-4 days after the last split, the cells were washed three times in Dulbecco's phosphate buffered saline. The cells were then re-suspended in supplemented media without T-STIM™ at a cell density of ~2×10⁵ cells/mL and plated in 96-well white walled clear bottom microplates at 90 μl/well. Experiments were also conducted using supplemented media (without T-STIM™) adjusted to pH 6.7-7, in order to minimize the release of conjugates during the course of incubation. Then, 10 μl of 10× concentrations of test compound, diluted in supplemented media without T-STIM™, was added. The cells were incubated at 37° C. in a 5% $CO_2$ atmosphere for 24 hours. Following the 24 hour incubation, 100 μL of Promega's CELLTITER-GLO® reagent was added to each well. The plates were mixed for two minutes on an orbital shaker then incubated at room temperature for ten minutes. Luminescence was then recorded using Perkin Elmer's TOPCOUNT® instrument at an integration time of one second/well.

For the [mPEG2-C2-fmoc-20K]-[rIL-2] releasable conjugates from Example 2 and the [mPEG2-CAC-fmoc-20K]-[rIL-2] releasable conjugates from Example 3, the activity of both released IL-2 and unreleased conjugates were tested. The test compounds were stored under acidic condition (10 mM sodium acetate buffer, pH 4) to stabilize conjugation. To test the activity of conjugates, the sample was diluted from the storage buffer into supplemented media~one hour prior to the assay. To test the activity of released IL-2, the releasable conjugates {i.e., [mPEG2-C2-fmoc-20K]-[rIL-2] conjugates from Example 2 and [mPEG2-CAC-fmoc-20K]-[rIL-2] conjugates from Example 3} were diluted ten-fold in 100 mM (final concentration) sodium bicarbonate buffer, pH 9 and pre-incubated at 37° C. for eight hours prior to start of the assay.

The $EC_{50}$ values (concentration of test compound required to exhibit 50% of maximal response) for cell proliferation were obtained from non-linear regression analysis of dose-response curves, using GraphPad's Prism 5.01 software.

Figure 7:
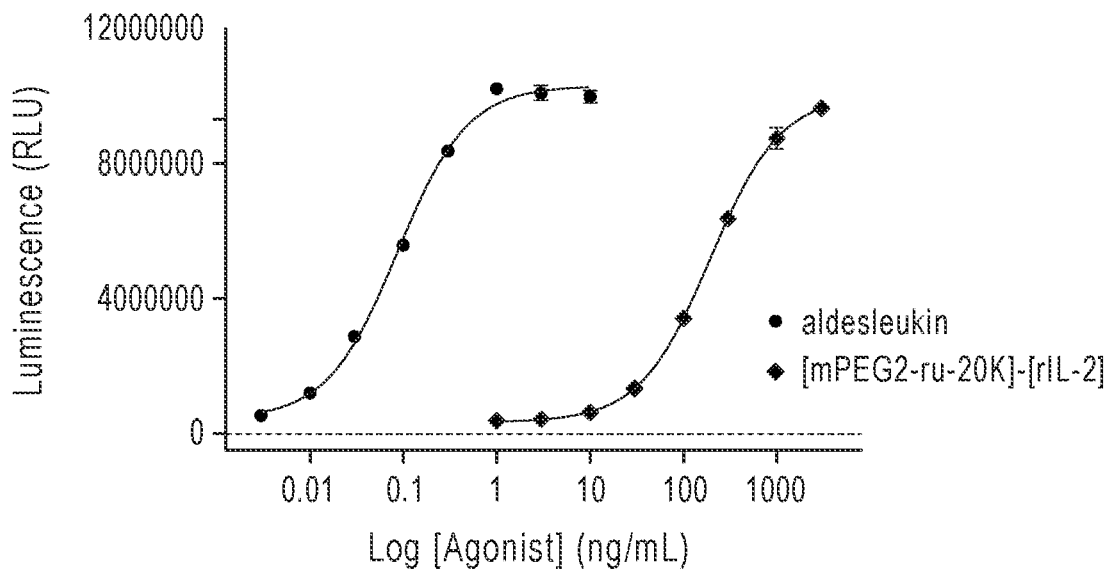
FIG. 7 shows a plot of the proliferation of CTLL-2 cells in response to aldesleukin and stable [mPEG2-ru-20K]-[rIL-2], as further described in Example 11. Data points are means of one experiment in triplicate determinations. Error bars represent standard error of the mean.
Figure 8:
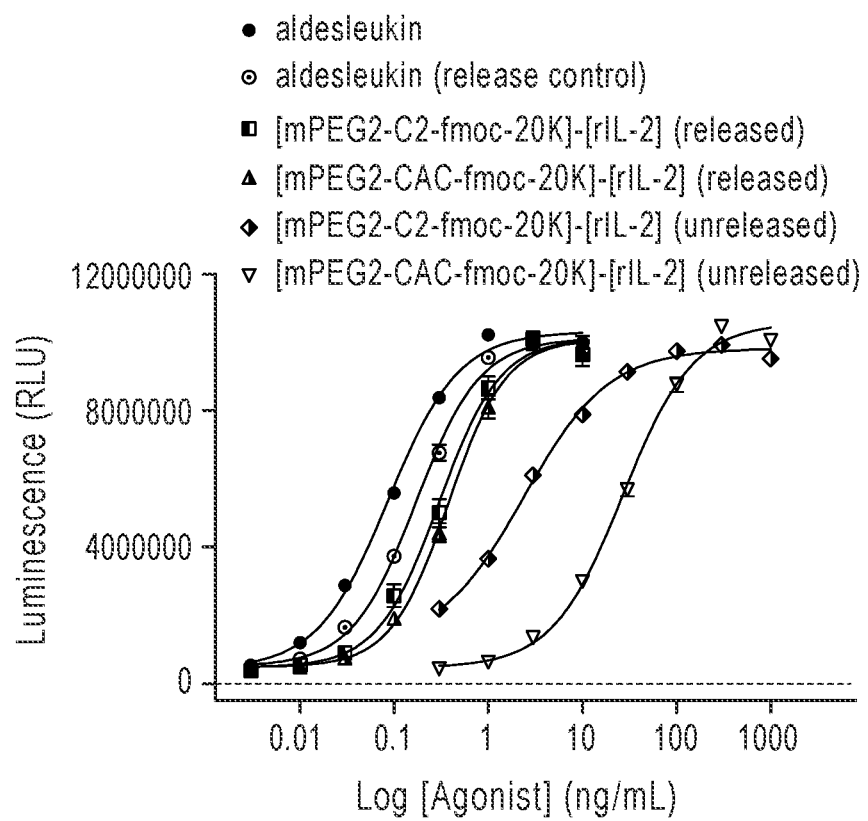
FIG. 8 shows a plot of the proliferation of CTLL-2 cells in response to aldesleukin, released and unreleased [mPEG2-C2-fmoc-20K]-[rIL-2] and [mPEG2-CAC-fmoc-20K]-[rIL-2], as further described in Example 11. Data points are means of one experiment in triplicate determinations. Error bars represent standard error of the mean.

The activities of aldesleukin and the conjugates were measured using a cell proliferation assay, and a summary of the results are shown in Table 4. All test articles induced growth of CTLL-2 cells in a dose-dependent manner. Since the releasable conjugates were pre-incubated under conditions to force release the protein, aldesleukin was also pre-incubated as a control to test for stability of the protein itself under the forced release treatment conditions. As shown in Table 4, aldesleukin remained stable following pre-incubation under the release conditions (8 hours at 37° C., pH 9) and exhibited relative potency to aldesleukin stored under recommended conditions. Following pre-incubation of [mPEG2-C2-fmoc-20K]-[rIL-2] from Example 2 and [mPEG2-CAC-fmoc-20K]-[rIL-2] from Example 3 under conditions to induce release of IL-2, activity was regained as shown in FIG. 8; IL-2 released from these conjugates displayed relative potency to the control aldesleukin, whereas some of the unreleased conjugates were less potent relative to aldesleukin. The stable 3-mer [mPEG2-ru-20K]-[rIL-2] conjugates displayed the least potency (FIG. 7) and was 0.04% relative to aldesleukin, but 1-mer [mPEG2-ru-20K]-[rIL-2] showed equivalent potency to aldesleukin in view the known standard deviation of the assay.

TABLE 4

Summary of CTLL-2 Cell Proliferation in Response to Aldesleukin and PEG-IL-2 conjugates.

| Test compound | EC50 (ng/mL) | Potency Relative to Aldesleukin (%) |
|---|---|---|
| aldesleukin | 0.111 | 102 |
| aldesleukin (release control) | 0.113 | 100 |
| 3-mer [mPEG2-C2-fmoc-20K]-[rIL-2] (released) | 0.076 | 149 |
| 1-mer [mPEG2-C2-fmoc-20K]-[rIL-2] (released) | 0.105 | 108 |
| 3-mer [mPEG2-CAC-fmoc-20K]-[rIL-2] (released) | 0.246 | 46 |
| 1-mer [mPEG2-CAC-fmoc-20K]-[rIL-2] (released) | 0.056 | 202 |
| 3-mer [mPEG2-C2-fmoc-20K]-[rIL-2] (unreleased) | 0.497 | 23 |
| 1-mer [mPEG2-C2-fmoc-20K]-[rIL-2] (unreleased) | 0.074 | 153 |
| 3-mer [mPEG2-CAC-fmoc-20K]-[rIL-2] (unreleased) | 5.163 | 2 |
| 1-mer [mPEG2-CAC-fmoc-20K]-[rIL-2] (unreleased) | 0.143 | 79 |
| 3-mer [mPEG2-ru-20k]-[rIL-2] | 194.400 | 0.04 |
| 1-mer [mPEG2-ru-20k]-[rIL-2] | 0.168 | 67 |

Example 12

Pharmacokinetics of Exemplary (rIL-2)-PEG Conjugates

The pharmacokinetic profiles of aldesleukin (control), [mPEG2-C2-fmoc-20K]-[rIL-2] from Example 2, [mPEG2-CAC-fmoc-20K]-[rIL-2] from Example 3, and [mPEG2-ru-20K]-[rIL-2] from Example 4 were evaluated in an ELISA following a single injection in mice.

Aldesleukin concentrations were measured by a heterogeneous, sandwich ELISA. Briefly, 96-well microtiter plates were coated with mouse monoclonal antibody to IL-2 and blocked. Samples and standard were prepared in neat plasma and were subsequently diluted to 10% plasma with buffer containing biotinylated rabbit polyclonal antibodies to IL-2 before being incubated on the assay plates. Streptavidin-Horseradish Peroxidase followed by the colorimetric substrate, 3,3',5,5'-tetramethylbenzidine (TMB) was used to detect IL-2. Stop solution was added and the absorbance was read at 450 nm with background subtraction at 650 nm. The standard curve was generated by a weighted, 4-parameter algorithm, and the sample concentrations determined by interpolation to the standard curve. The lower limit of quantitation was 0.05 ng/mL.

Pooled 1-mer/2-mer [mPEG2-ru-20K]-[rIL-2] concentrations were measured by a homogeneous HTRF® assay (Cisbio US, Bedford MA). Reaction mixture (15 uL, europium chromate conjugated mouse monoclonal antibody to IL-2, Streptavidin-d2, and biotinylated rabbit monoclonal antibody to PEG) was added to white, low-volume, 384-well microtiter plates. Samples and standards (5 uL) diluted in neat plasma were added and the plates incubated. The plates were read on a fluorescence reader at 615 and 665 nm, and Delta F calculated. The standard curve was generated by a weighted, 5-parameter algorithm and the sample concentrations determined by interpolation to the standard curve. The lower limit of quatitation was 0.5 ng/mL.

3-mer [mPEG2-C2-fmoc-20K]-[rIL-2] and 3-mer [mPEG2-CAC-fmoc-20K]-[rIL-2] were measured in a total IL-2 assay. Since the [mPEG2-C2-fmoc-20K]-[rIL-2] and [mPEG2-CAC-fmoc-20K]-[rIL-2] conjugates are releasable conjugates, different species of the molecule will be present in a sample making individual quantitation difficult; therefore, total IL-2 levels were measured. The polymer-containing component of the conjugates was forced released from the conjugates by diluting the samples and standard stock, prepared in neat plasma, 1:1 with releasing buffer (100 mM HEPES/100 mM Tris-HCL, pH 9) and incubating at 37° C. for 30 to 36 hours. After the incubations, a 25% volume of 0.1M acetic acid was added to neutralize the high pH. The released IL-2 was measured by the ELISA described above.

Figure 9:
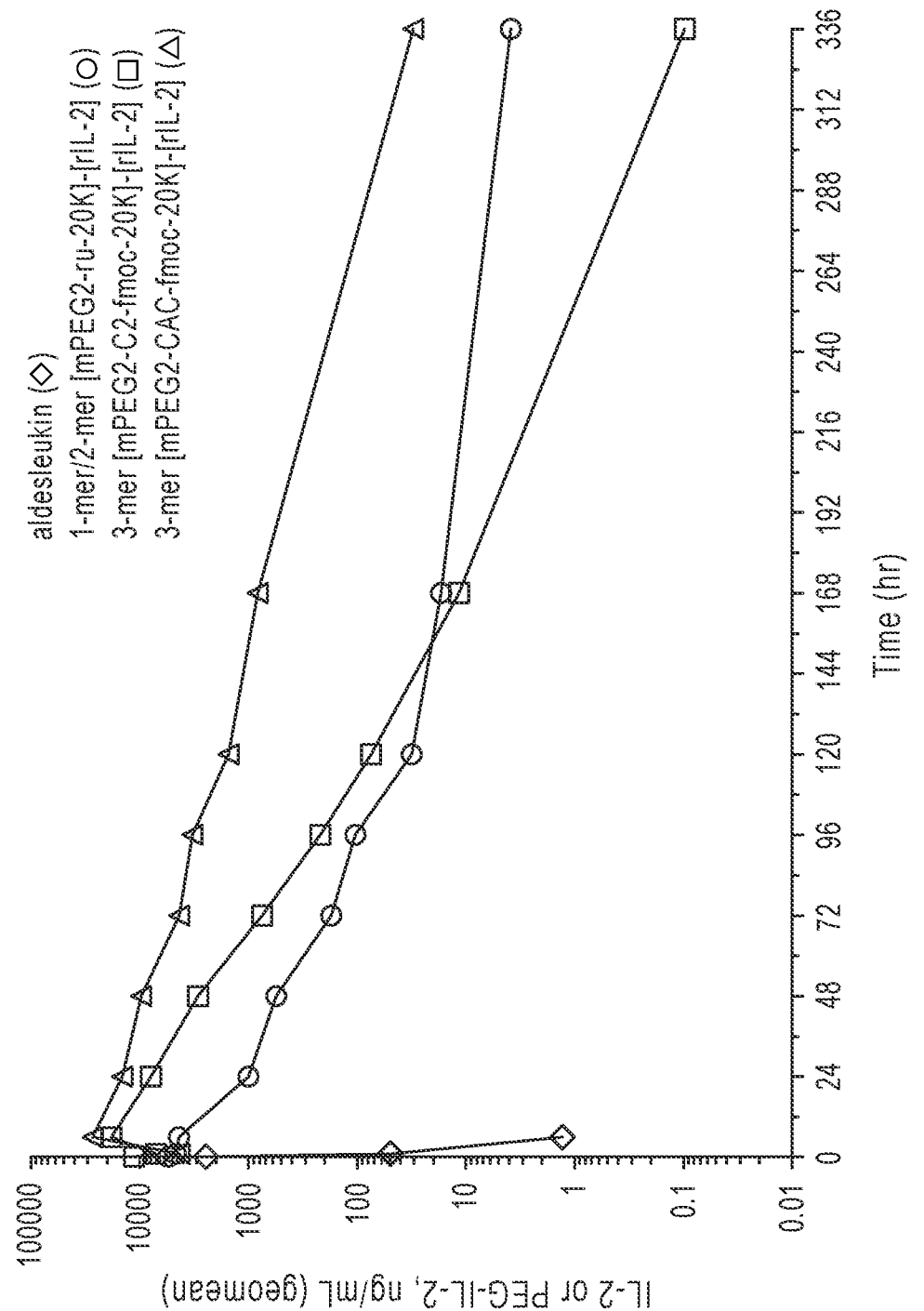
FIG. 9 shows a plot of the concentration-time curves following a single injection in mice, as further described in Example 12.

FIG. 9 shows a concentration-time plot of the tested articles in C57BL/6 mice after a single, intra-muscular injection (1 mg/kg). Sodium heparanized plasma samples were collected at ten minutes, and at 1, 6, 24, 48, 72, 96, 120, 168 and 336 hours. The geomean concentrations were calculated from 3 mice per time point. As shown in FIG. 9, aldesleukin had a short ½-life and could not be detected after 6 hours (<0.05 ng/mL) while the conjugates had an extended ½-life and were still detected at 336 hours.

Example 13

Lung Metastatic Melanoma Efficacy Studies

To evaluate the efficacy of compounds having purported IL-2 activity, the metastatic melanoma lung model has been widely used and is developed in C57BL/6 mice. In this model, mice are first intravenously administered B16F10 melanoma cells, which causes the development of lung nodules of different numbers and sizes. The lung nodule numbers as well as total surface area of these lesions varies depending on cell concentrations implanted. A test compound of interest is then administered to a treatment group of mice and another group of mice is left untreated to serve as a control. The efficacy of the test compound can be determined, as a percent reduction in the number and size of the lung nodules and the total lesion area for each lung between the treated and untreated groups.

In this study, 100,000 B16F10 cells (passage not exceeding P8) were implanted by tail vein injections. On the third day from the date of cell implantation, test compounds of interest (or vehicle) were administered as indicated in the Table 5 following either IP (intraperitoneal) or IV (intravenous) routes of administration.

TABLE 5

Groups Assignments for Example 13

| Group no. | Test Article | B16F10 cells | Route of administration | Animal No. | Dose |
|---|---|---|---|---|---|
| A | aldesleukin (Prometheus Laboratories Inc.) | 100,000 | IP | 1-12 | b.i.d × 5 |
| B | IL-2 moiety of Example 1 | 100,000 | IP | 1-12 | b.i.d × 5 |
| C | vehicle | 100,000 | IP | 1-12 | b.i.d × 5 |
| D | NKT-11135-A-001 | 100,000 | IV | 1-12 | q2d × 3 |
| E | Pooled 3-mer/4-mer [mPEG2-CAC-fmoc-20K]-[rIL-2] | 100,000 | IV | 1-12 | q2d × 3 |
| F | Pooled 1-mer/2-mer [mPEG2-ru-20K]-[rIL-2] | 100,000 | IV | 1-12 | q2d × 3 |
| G | Pooled 3-mer/4-mer [mPEG2-ru-20K]-[rIL-2] | 100,000 | IV | 1-12 | q2d × 3 |

Note:

"b.i.d × 5" means twice a day for five days;

"q2d × 3" means every second day for 3 doses

On day 14 from day of cell implantation, mice were sacrificed while isolating and fixing lungs in the Bowen's solution containing formaldehyde for a day or two. The lungs (which were fixed in the Bowen's solution) were examined under stereomicroscope and the number and size of lesions for each lung were determined.

Figure 10:
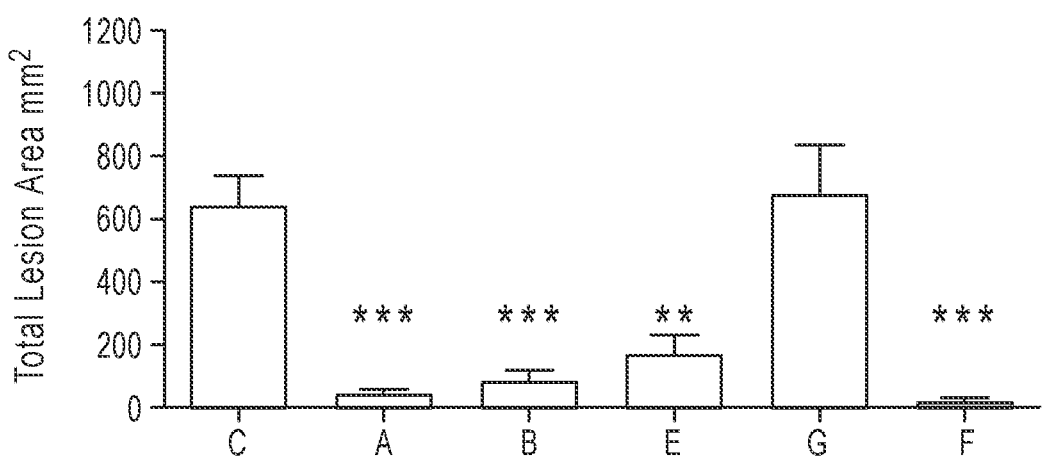
FIG. 10 shows a plot of total lesion area ($mm^2$) for several test compounds as further described in Example 13.

As shown in FIG. 10, on day 14 from the day of cell implantation mice were sacrificed and their isolated lungs were fixed in Bowen's solution. The tumor nodules and their sizes were counted for each of aldesleukin (Prometheus Laboratories Inc., San Diego CA), IL-2 moiety of Example 1, pooled 3-mer/4-mer [mPEG2-CAC-fmoc-20K]-[rIL-2], pooled 3-mer/4-mer [mPEG2-ru-20K]-[rIL-2], and pooled 1-mer/2-mer [mPEG2-ru-20K]-[rIL-2].

Example 14

Subcutaneous B16F10 Melanoma Efficacy Studies

To evaluate the efficacy of compounds having purported IL-2 activity, the highly robust subcutaneous melanoma model in syngenic mice, i.e., C57BL/6 mice, has been used. Briefly, one million B16F10 cells were implanted subcutaneously for each 5-6 week old C57BL/6 mouse at mid-dorsal region. Tumors were allowed to grow to palpable size, i.e., 70-120 cu mm before randomization and assigning groups as shown in the Table 6. The mice were administered test compounds i.e., aldesleukin (Prometheus Laboratories Inc., San Diego CA), rIL-2-polymer conjugates or vehicle at different dose concentrations and dose regimes. The body weights and tumor volumes were measured every alternative day. The end point for this study is the time to reach median tumor volume of 1500 cu mm for a given group or 45 days whichever is earlier.

TABLE 6

Groups Assignments for Example 14

| Test Compound | Subgroup (n = 9) | Dose concentration (mg/kg) | Route of administration | Dose |
|---|---|---|---|---|
| Pooled 3-mer/4-mer [mPEG2-CAC-fmoc-20K]-[rIL-2] | A1 | 2 | IV | q1d |
|  | A2 | 4 |  |  |
| Pooled 1-mer/2mer [mPEG2-C2-fmoc-20K]-[rIL-2] | E1 | 6 | IV | q1d |
|  | E2 | 8 |  |  |
| aldesleukin (Prometheus Laboratories Inc.) | C H (n = 6) | 3 | IP | b.i.d × 5 |
| Pooled 3-mer/4-mer [mPEG2-C2-fmoc-20K]-[rIL-2] | B1 | 2 | IV | q1d |
|  | B2 | 4 |  |  |
| Pooled 1-mer/2-mer [mPEG2-ru-20K]-[rIL-2] | F1 | 6 | IV | q1d |
|  | F2 | 9 |  |  |
| Pooled 1-mer/2-mer [mPEG2-CAC-fmoc-20K]-[rIL-2] | G1 | 2 | IV | q1d |
|  | G2 | 4 |  |  |
| Vehicle: 10 mM Sodium acetate; 150 mM NaCl, pH 4.5; 2% Sucrose | D I | As per body weight | IV | q1d |

Figure 11A:
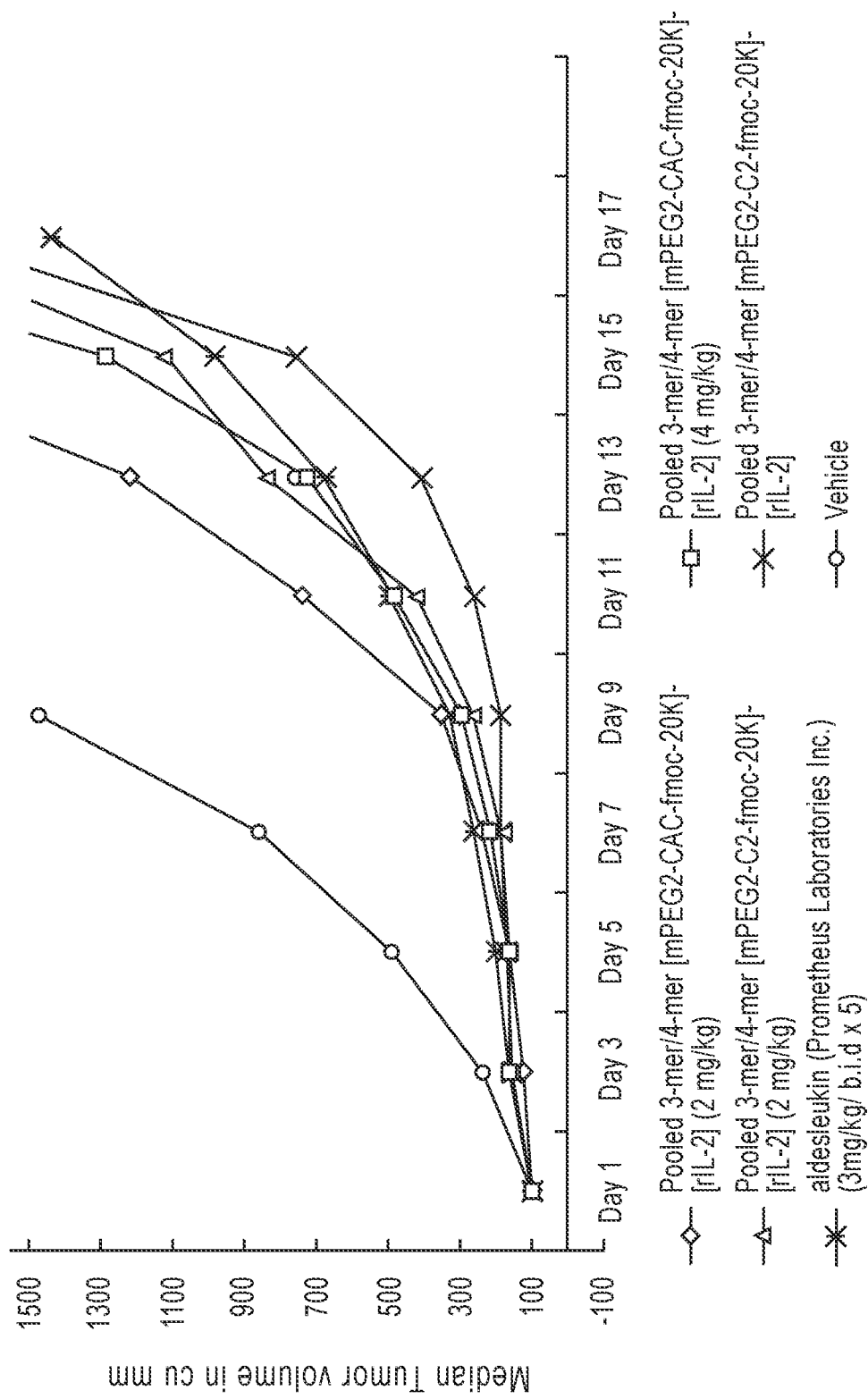
FIG. 11A and FIG. 11B are plots showing time to tumor progression curves for tested articles at various administration schemes, as further described in Example 14.
Figure 11B:
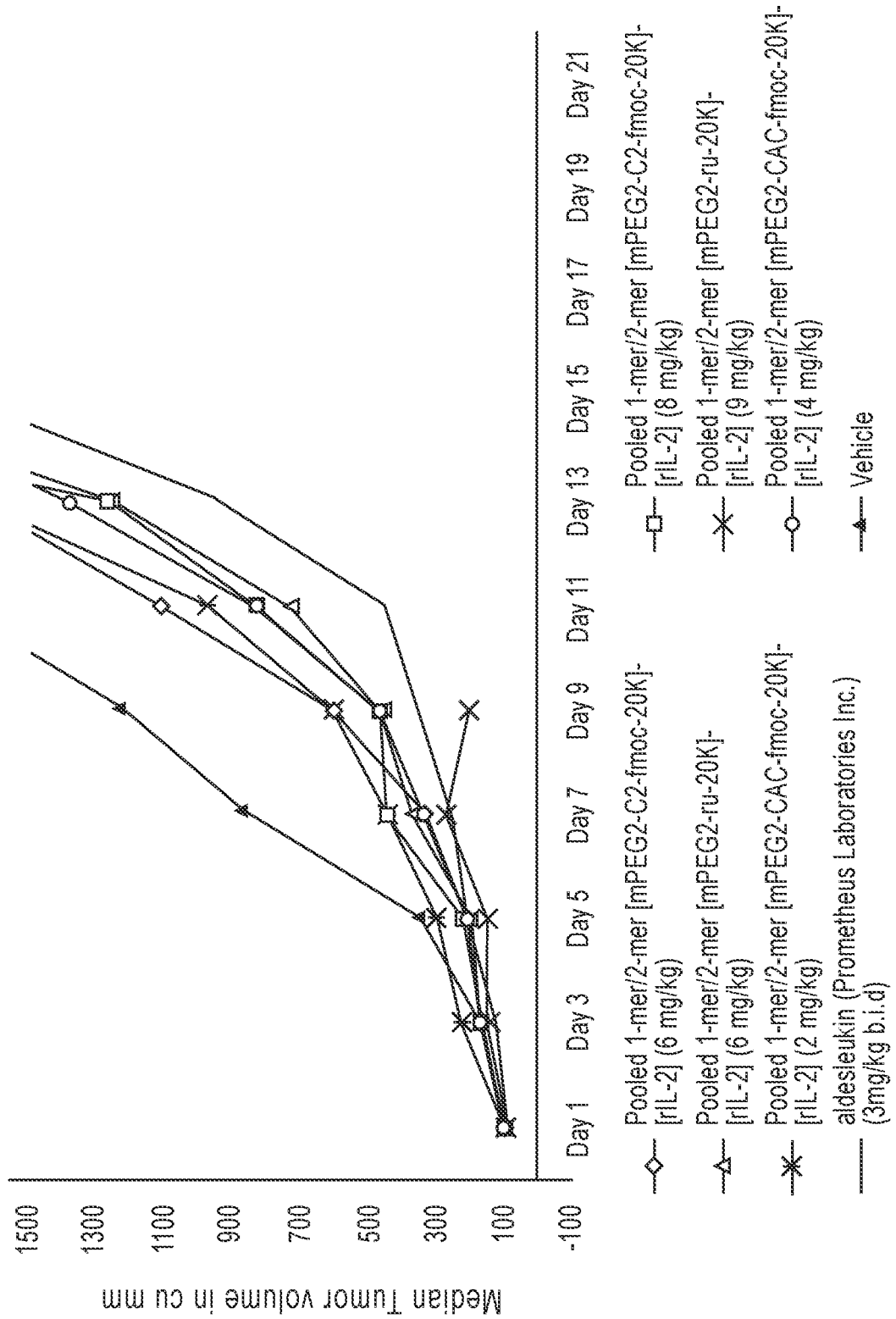

Dose-response curves for tumor growth inhibition following the administration of aldesleukin (Prometheus Laboratories Inc.) and rIL-2-polymer conjugates at different administration schemes are provided in FIG. 11A and FIG. 11B. These results indicate that the tested rIL-2-polymer conjugates evidenced better efficacy at a single dose over aldesleukin (Prometheus Laboratories Inc.), which was dosed at 3 mg/kg twice a day for five days.

FIG. 11A shows time to tumor progression after a single dose administration of rIL-2-polymer conjugates to reach a median tumor volume of 1500 mm$^3$. The tumor growth delay (TGD) from the tumor progression curves was found to be 4.6 and 6.2 days, respectively, for pooled 3-mer/4-mer [mPEG2-CAC-fmoc-20K]-[rIL-2] at 2 mg/kg and 4 mg/kg dose concentrations. For pooled 3-mer/4-mer [mPEG2-C2-fmoc-20K]-[rIL-2], TGD was found to be 6.4 and 7.6 days, respectively, at 2 mg/kg and 4 mg/kg dose concentrations.

FIG. 11B shows time to tumor progression after single dose administration rIL-2-polymer conjugates to reach a median tumor volume of 1500 mm$^3$. The TGD from the tumor progression curves was found to be 3.6 and 4.6 days, respectively, for pooled 1-mer/2-mer [mPEG2-C2-fmoc-20K]-[rIL-2] at 6 mg/kg and 8 mg/kg dose concentrations. For pooled 1-mer/2-mer [mPEG2-ru-20K]-[rIL-2], the TGD was found to be 3.8 at 2 mg/kg while a 4 mg/kg dose concentration was found to be toxic in nature. TGD from the tumor progression curves was found to be 2.2 and 3.6 days, respectively, for pooled 1-mer/2-mer [mPEG2-CAC-fmoc-20K]-[rIL-2] at 2 mg/kg and 4 mg/kg dose concentrations.

In short, the efficacy in both a lung lesion metastasis model (Example 13) and in a subcutaneous mouse melanoma model (Example 14) was achieved with rIL-2 polymer conjugates at substantially lower frequency of dosing and lower overall protein amount as compared to aldesleukin (Prometheus Laboratories Inc.).

```
                                           SEQ ID NO: 1
MYRMQLLSCI ALSLALVTNS APTSSSTKKT QLQLEHLLLD
-20        -10        1          11

LQMILNGINN YKNPKLTRML TFKFYMPKKA TELKHLQCLE
21         31         41         51

EELKPLEEVL NLAQSKNFHL RPRDLISNIN VIVLELKGSE
61         71         81         91

TTFMCEYADE TATIVEFLNR WITFCQSIIS TLT
101        111        121

SEQ ID NO: 2
                      APTSSSTKKT QLQLEHLLLD

LQMILNGINN YKNPKLTRML TFKFYMPKKA TELKHLQCLE

EELKPLEEVL NLAQSKNFHL RPRDLISNIN VIVLELKGSE

TTFMCEYADE TATIVEFLNR WITFCQSIIS TLT

SEQ ID NO: 3
                      PTSSSTKKT  QLQLEHLLLD

LQMILNGINN YKNPKLTRML TFKFYMPKKA TELKHLQCLE
```

```
                                           SEQ ID NO: 4
EELKPLEEVL NLAQSKNFHL RPRDLISNIN VIVLELKGSE

TTFMCEYADE TATIVEFLNR WITFSQSIIS TLT

SEQ ID NO: 4
                      APTSSSTKKT QLQLEHLLLD

LQMILNGINN YKNPKLTRML TFKFYMPKKA TELKHLQCLE

EELKPLEEVL NLAQSKNFHL RPRDLISRIN VIVLELKGSE

TTFMCEYADE TATIVEFLNR WITFCQSIIS TLT

SEQ ID NO: 5
  1   CATATGCCGACCAGCAGCAGCACCAAAAAAACCCAGCTGC

AGCTGGAACATCTGCTGCTG

61   GATCTGCAGATGATCCTGAACGGTATCAACAACTACAAA

ACCCGAAACTGACCCGTATG

121   CTGACCTTCAAATTCTACATGCCGAAAAAAGCAACCGAAC

TGAAACATCTGCAGTGCCTG

181   GAAGAAGAACTGAAACCGCTGGAAGAAGTGCTGAACCTGG

CACAGAGCAAAAACTTCCAT

241   CTGCGTCCGCGTGATCTGATCAGCAACATCAACGTGATCG

TGCTGGAACTGAAAGGTAGC

301   GAAACCACCTTCATGTGCGAATACGCAGATGAAACCGCAA

CCATCGTGGAATTTCTGAAC

361   CGTTGGATCACCTTCAGCCAGAGCATCATCAGCACCCTGA

CCTAAGAATTC
```

---

What is claimed is:

1. A composition comprising a conjugate of an interleukin-2 (IL-2) moiety, the conjugate comprising from three to seven branched poly(ethylene glycol) polymers, each covalently attached via a releasable linkage to an amino group of the IL-2 moiety, wherein the IL-2 moiety is aldesleukin, each branched poly(ethylene glycol) has a weight average molecular weight from about 20,000 daltons to about 85,000 daltons, and the composition possesses no IL-2 activity prior to in vivo release of the branched poly(ethylene glycol) polymer(s) from the conjugate.

2. The composition of claim 1, wherein each branched poly(ethylene glycol) polymer is terminally capped with an alkoxy end-capping moiety.

3. The composition of claim 1, wherein each branched poly(ethylene glycol) polymer is covalently attached at an amino group of a lysine of the IL-2 moiety.

4. The composition of claim 1, wherein three or four branched poly(ethylene glycol) polymers are attached to the IL-2 moiety.

5. The composition of claim 1, wherein each branched poly(ethylene glycol) polymer has a weight average molecular weight of about 20,000 daltons.

6. The composition of claim 5, wherein each branched poly(ethylene glycol) polymer comprises two poly(ethylene glycol) chains.

7. The composition of claim 1, wherein the composition comprises a plurality of the conjugates comprising from three to seven branched poly(ethylene glycol) polymers covalently attached to the IL-2 moiety, and the composition possesses no IL-2 activity prior to in vivo release of the branched poly(ethylene glycol) polymer(s) from the conjugates comprised in the composition.

8. The composition of claim 6, wherein the composition comprises a plurality of the conjugates comprising from three to seven branched poly(ethylene glycol) polymers covalently attached to the IL-2 moiety, and the composition possesses no IL-2 activity prior to in vivo release of the branched poly(ethylene glycol) polymer(s) from the conjugates comprised in the composition.

9. The composition of claim 8, wherein the plurality of conjugates is a mixture of conjugates selected from the group of conjugates having four, five, six and seven branched poly(ethylene glycol) polymers covalently attached to the IL-2 moiety.

10. The composition of claim 9, wherein the plurality of conjugates is a mixture of conjugates having an average of six branched poly(ethylene glycol) polymers per interleukin-2 moiety.

11. A pharmaceutical composition comprising the composition of claim 1 and a pharmaceutically acceptable excipient.

12. The composition of claim 11, in a form suitable for injection.

13. The composition of claim 11, in the form of a lyophilate for reconstitution with a pharmaceutically acceptable diluent.

14. The composition of claim 11, wherein the pharmaceutically acceptable excipient is selected from the group consisting of carbohydrates, inorganic salts, buffers, acids, bases, and combinations thereof.

15. A method of treating a patient with cancer, the method comprising administering to the patient a pharmaceutical composition of claim 11.

\* \* \* \* \*